(12) United States Patent
Shudo et al.

(10) Patent No.: US 9,579,054 B2
(45) Date of Patent: Feb. 28, 2017

(54) DIAGNOSIS SUPPORTING DEVICE AND DIAGNOSIS SUPPORTING METHOD

(71) Applicant: JVC KENWOOD Corporation, Yokohama-shi, Kanagawa (JP)

(72) Inventors: Katsuyuki Shudo, Yokohama (JP); Masaru Ninomiya, Yokohama (JP); Shuji Hakoshima, Yokohama (JP)

(73) Assignee: JVC KENWOOD CORPORATION, Kanagawa (JP)

( * ) Notice: Subject to any disclaimer, the term of this patent is extended or adjusted under 35 U.S.C. 154(b) by 0 days.

(21) Appl. No.: 14/980,077

(22) Filed: Dec. 28, 2015

(65) Prior Publication Data

US 2016/0106354 A1   Apr. 21, 2016

Related U.S. Application Data

(63) Continuation of application No. PCT/JP2014/067289, filed on Jun. 27, 2014.

(30) Foreign Application Priority Data

Jun. 28, 2013 (JP) .................................. 2013-136124
Jul. 29, 2013 (JP) .................................. 2013-157030
(Continued)

(51) Int. Cl.
*A61B 3/14* (2006.01)
*A61B 5/16* (2006.01)
(Continued)

(52) U.S. Cl.
CPC ............ *A61B 5/168* (2013.01); *A61B 3/0058* (2013.01); *A61B 3/0091* (2013.01); *A61B 3/032* (2013.01);
(Continued)

(58) Field of Classification Search
CPC ... A61B 3/0008; A61B 3/0025; A61B 3/0058; A61B 3/0091; A61B 3/032;
(Continued)

(56) References Cited

U.S. PATENT DOCUMENTS 6,652,458 B2   11/2003   Blazey et al.
7,533,989 B2    5/2009   Ebisawa
(Continued)

FOREIGN PATENT DOCUMENTS

JP   07-035967    2/1995
JP   2002-360518  12/2002
(Continued)

OTHER PUBLICATIONS

Pierce K et al., Preference for Geometric Patterns Early in Life as a Risk Factor for Autism, Arch Gen Psychiatry, Jan. 2011; 68 (1): 101-109.
(Continued)

*Primary Examiner* — Huy K Mai
(74) *Attorney, Agent, or Firm* — Amin, Turocy & Watson LLP

(57) ABSTRACT

A diagnosis supporting device includes a display, an imaging unit configured to capture a subject, an eye gaze detector configured to detect an eye gaze direction of the subject from a captured image captured by the imaging unit, a gaze point detector configured to detect a gaze point of the subject in a display region of the display, based on the eye gaze direction, an output controller configured to display, on the display, a diagnosis image that includes a person image and a geometric pattern image, and in which at least one of contrast, color density, and a degree of transmittance of the person image or the geometric pattern image is changed over time, and an evaluator configured to calculate an evaluation
(Continued)

value of the subject, based on the gaze point detected by the gaze point detector when the diagnosis image is displayed.

8 Claims, 54 Drawing Sheets

(30) Foreign Application Priority Data

| | | |
|---|---|---|
| Jul. 30, 2013 | (JP) | 2013-157756 |
| Jul. 31, 2013 | (JP) | 2013-159682 |
| Feb. 21, 2014 | (JP) | 2014-032220 |
| Feb. 26, 2014 | (JP) | 2014-035948 |
| Feb. 26, 2014 | (JP) | 2014-035949 |
| Feb. 28, 2014 | (JP) | 2014-039246 |
| Feb. 28, 2014 | (JP) | 2014-039247 |
| Jun. 27, 2014 | (JP) | 2014-133219 |

(51) Int. Cl.
*A61B 3/113* (2006.01)
*A61B 3/00* (2006.01)
*A61B 5/00* (2006.01)
*A61B 3/06* (2006.01)
*A61B 3/032* (2006.01)

(52) U.S. Cl.
CPC ............... *A61B 3/06* (2013.01); *A61B 3/113* (2013.01); *A61B 5/7282* (2013.01)

(58) Field of Classification Search
CPC .......... A61B 3/06; A61B 3/063; A61B 3/066; A61B 3/11; A61B 3/111; A61B 3/113
USPC .................... 351/206, 209, 221, 237, 239
See application file for complete search history.

(56) References Cited

U.S. PATENT DOCUMENTS

| | | | |
|---|---|---|---|
| 8,371,693 | B2 | 2/2013 | Ebisawa |
| 9,135,708 | B2* | 9/2015 | Ebisawa ............ G06K 9/00604 |
| 2010/0016754 | A1 | 1/2010 | Whillock et al. |
| 2014/0247208 | A1* | 9/2014 | Henderek ............ G06F 3/0481 |
| | | | 345/156 |

FOREIGN PATENT DOCUMENTS

| | | |
|---|---|---|
| JP | 2005-185431 | 7/2005 |
| JP | 2005-198743 | 7/2005 |
| JP | 2008-125619 | 6/2008 |
| JP | 2011-206542 | 10/2011 |
| WO | 2011/049558 A1 | 4/2011 |

OTHER PUBLICATIONS

International Search Report for International Patent Application No. PCT/JP2014/067289 dated Sep. 2, 2014, 4 pages.
Written Opinion for International Patent Application No. PCT/JP2014/067289 dated Sep. 2, 2014, 3 pages.
Extended European Search Report for European Patent Application No. 14818648.9 mailed on Dec. 8, 2016.

* cited by examiner

HUE, CHROMA, AND CONTRAST OF GEOMETRIC PATTERN IS HIGH, AND CHANGE OF PICTURE IS LARGE

HUE, CHROMA, AND CONTRAST OF GEOMETRIC PATTERN IS LOW, AND CHANGE OF PICTURE IS SMALL

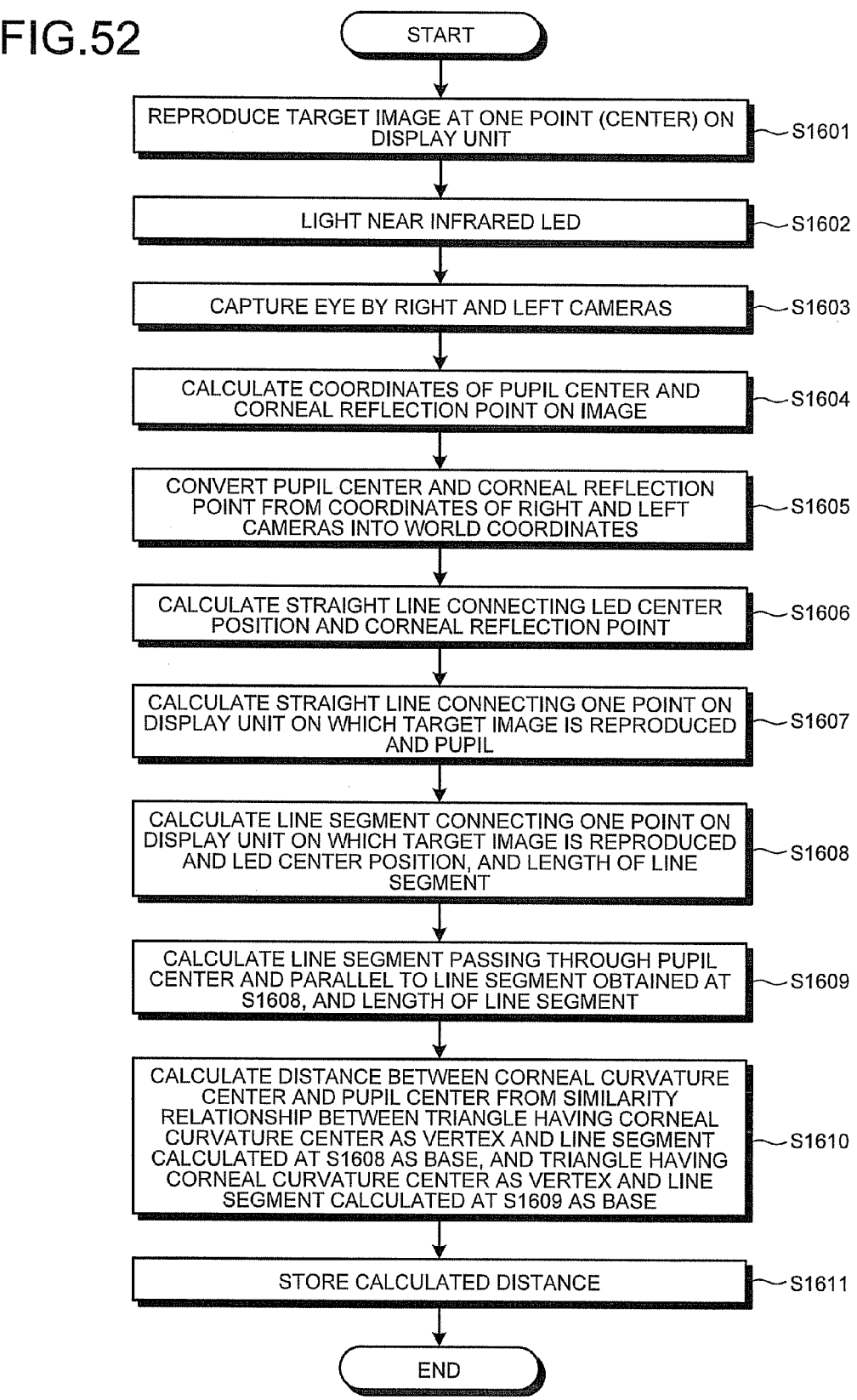

DIAGNOSIS SUPPORTING DEVICE AND DIAGNOSIS SUPPORTING METHOD

CROSS-REFERENCE TO RELATED APPLICATIONS

This application is a continuation of PCT international application Ser. No. PCT/JP2014/067289 filed on Jun. 27, 2014 which designates the United States, incorporated herein by reference, and which claims the benefit of priority from Japanese Patent Application No. 2014-035949, filed on Feb. 26, 2014, Japanese Patent Application No. 2013-159682, filed on Jul. 31, 2013, Japanese Patent Application No. 2014-035948, filed on Feb. 26, 2014, Japanese Patent Application No. 2013-157030, filed on Jul. 29, 2013, Japanese Patent Application No. 2014-032220, filed on Feb. 21, 2014, Japanese Patent Application No. 2013-136124, filed on Jun. 28, 2013, Japanese Patent Application No. 2014-039247, filed on Feb. 28, 2014, Japanese Patent Application No. 2014-039246, filed on Feb. 28, 2014, Japanese Patent Application No. 2014-133219, filed on Jun. 27, 2014, and Japanese Patent Application No. 2013-157756, filed on Jul. 30, 2013 incorporated herein by reference.

BACKGROUND OF THE INVENTION

1. Field of the Invention

The present invention relates to a technology of supporting diagnosis.

2. Description of the Related Art

In recent years, it is said that the number of developmentally disabled persons is increasing. The developmental disorder is known that symptoms can be relieved by early discovery and start of rehabilitation, and an effect to adapt to society can become high. Our country has been striving to early discovery by a medical interview at the time of one-and-a-half-year-old medical examination, and the like. However, there are problem such as psychiatrist shortage, and taking time for the medical interview, and an effect thereof cannot be said to be sufficient. Therefore, an objective and efficient diagnosis supporting device of the developmental disorder has been sought.

For the early discovery of the developmental disorder, it is ideal to have diagnosis at the time of the one-and-a-half-year-old medical examination, for example. As the developmental disorder, attention deficit/hyperactivity disorder (ADHD), autistic spectrum disorder (ASD), and the like are known. Examples of characteristics of disabled children of ADHD include difficulty in concentration on one thing, and instability for a gaze object, and easy movement of a gaze point. Further, an example of a characteristic of a disabled child of ASD includes not looking at a facing person (looking away of eye gaze). Further, the disabled child of ASD is known to have a preference for geometric pattern pictures to person pictures. Further, methods of supporting diagnosis of developmental disorder by application of methods of capturing a face of a human with a camera and detecting a gaze point by calculation of positions of corneal reflection and a pupil have been proposed.

However, the conventional methods of detecting a gaze point may not be able to appropriately support diagnosis, depending on a diagnosis image presented to a subject, and a higher accurate detection method has been sought.

SUMMARY OF THE INVENTION

It is an object of the present invention to at least partially solve the problems in the conventional technology.

A diagnosis supporting device according to an aspect of the present invention includes a display, an imaging unit configured to capture a subject, an eye gaze detector configured to detect an eye gaze direction of the subject from a captured image captured by the imaging unit, a gaze point detector configured to detect a gaze point of the subject in a display region of the display, based on the eye gaze direction, an output controller configured to display, on the display, a diagnosis image that includes a person image and a geometric pattern image, and in which at least one of contrast, color density, and a degree of transmittance of the person image or the geometric pattern image is changed over time, and an evaluator configured to calculate an evaluation value of the subject, based on the gaze point detected by the gaze point detector when the diagnosis image is displayed.

A diagnosis supporting method according to another aspect of the present invention includes an eye gaze detection step of detecting, from a captured image captured by an imaging unit that captures a subject, an eye gaze direction of the subject, a gaze point detection step of detecting a gaze point of the subject in a display region on a display, based on the eye gaze direction, an output control step of displaying, on the display, a diagnosis image including a person image and a geometric pattern image, and in which at least one of contrast, color density, a degree of transmittance of the person image or the geometric pattern image is changed over time, and an evaluation step of calculating an evaluation value of the subject, based on the gaze point detected in the gaze point detection step when the diagnosis image is displayed.

The above and other objects, features, advantages and technical and industrial significance of this invention will be better understood by reading the following detailed description of presently preferred embodiments of the invention, when considered in connection with the accompanying drawings.

BRIEF DESCRIPTION OF THE DRAWINGS

FIG. 52 is a flowchart illustrating an example of calculation processing of the modification.

DETAILED DESCRIPTION OF THE PREFERRED EMBODIMENTS

Hereinafter, a diagnosis supporting device and a diagnosis supporting method of the present invention will be described with reference to the appended drawings.

First Embodiment

Figure 1:
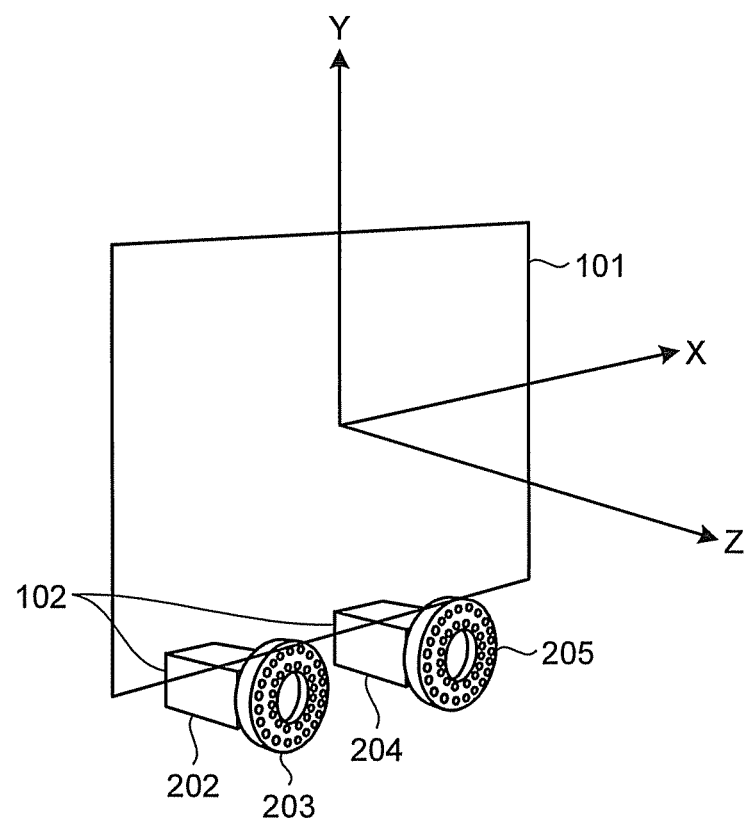
FIG. 1 is a diagram illustrating an example of arrangement of a display, stereo cameras, and a light source used in a first embodiment.

FIG. 1 is a diagram illustrating an example of arrangement of a display, stereo cameras, and a light source used in a first embodiment. As illustrated in FIG. 1, in the present embodiment, a pair of stereo cameras 102 is arranged at a lower side of a display screen 101. The stereo cameras 102 are imaging units that can perform stereo capturing with infrared rays, and includes a right camera 202 and a left camera 204.

Infrared light emitting diode (LED) light sources 203 and 205 are respectively arranged immediately before respective lenses of the right camera 202 and the left camera 204 in a circumferential direction. The infrared LED light sources 203 and 205 include an inner circumferential LED and an outer circumferential LED having mutually different wavelengths to be emitted. A pupil of a subject is detected with the infrared LED light sources 203 and 205. As a method of detecting a pupil, a method described in Patent Literature 2 or the like can be used.

In detecting an eye gaze, a space is expressed in coordinates, and a position is identified. In the present embodiment, a coordinate in an up and down direction is a Y coordinate (the up direction is +), a coordinate in a transverse direction is an X coordinate (the right direction is +), and a coordinate in a depth direction is a Z coordinate (the front side is +), where a middle position on the display screen 101 is the origin.

Figure 2:
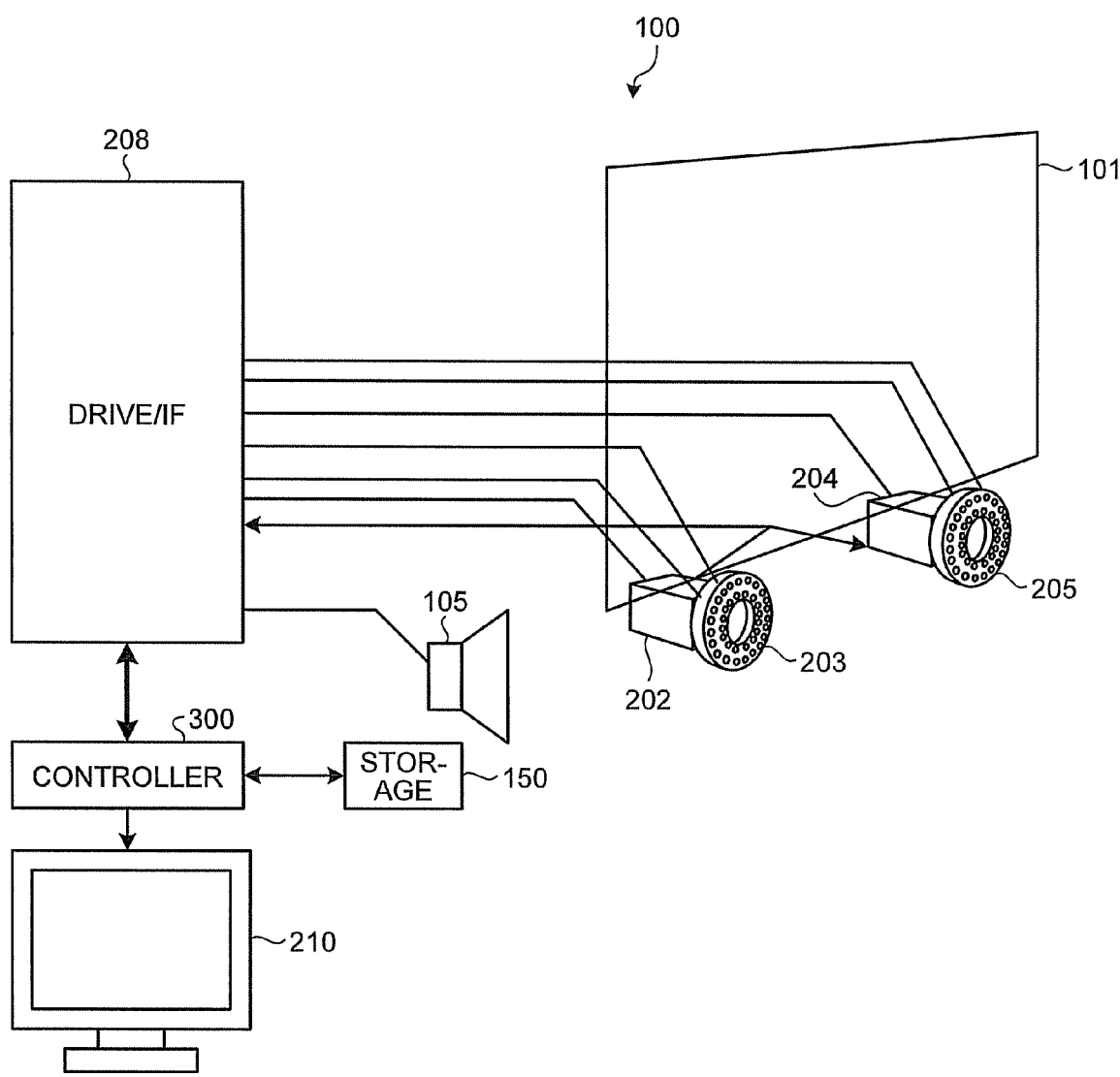
FIG. 2 is a diagram illustrating an outline of functions of a diagnosis supporting device of the first embodiment.

FIG. 2 is a diagram illustrating an outline of functions of a diagnosis supporting device 100. FIG. 2 illustrates the configuration illustrated in FIG. 1, and another configuration used for driving of the aforementioned configuration. As illustrated in FIG. 2, the diagnosis supporting device 100 includes the right camera 202, the left camera 204, the infrared LED light sources 203 and 205, a speaker 105, a drive/interface (IF) unit 208, a controller 300, a storage 150, a display 210. In FIG. 2, a positional relationship of the display screen 101 with the right camera 202 and the left camera 204 is illustrated in an easy-to-understand manner. However, the display screen 101 is a screen displayed on the display 210. Note that the driver and the IF unit may be an integrated body or separate bodies.

The speaker 105 functions as an audio output unit that outputs an audio and the like for prompting the subject to pay attention, at the time of calibration and the like.

The drive/IF 208 drives units included in the stereo cameras 102. Further, the drive/IF 208 serves as an interface between the units included in the stereo cameras 102, and the controller 300.

The storage 150 stores various types of information such as a control program, a measurement result, and a diagnosis support result. The storage 150 stores an image to be displayed on the display 210, and the like. The display 210 displays various types of information such as an object image for diagnosis, and the like.

Figure 3:
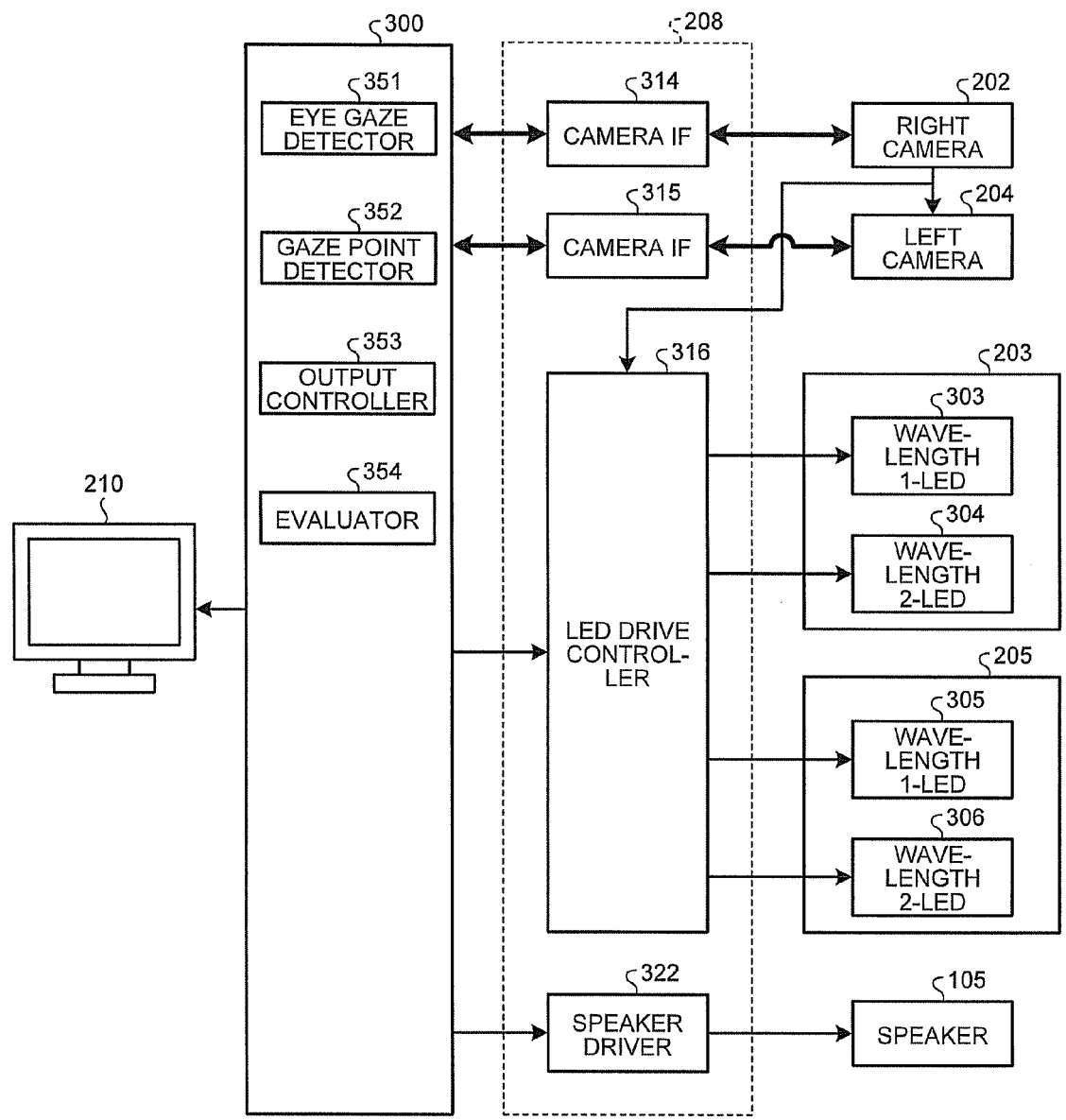
FIG. 3 is a block diagram illustrating an example of detailed functions of respective units illustrated in FIG. 2.

FIG. 3 is a block diagram illustrating an example of detailed functions of the respective units illustrated in FIG. 2. As illustrated in FIG. 3, the display 210 and the drive/IF 208 are connected to the controller 300 (control device). The drive/IF 208 includes camera IFs 314 and 315, an LED drive controller 316, and a speaker driver 322.

The right camera 202 and the left camera 204 are connected to the drive/IF 208 respectively through the camera IFs 314 and 315. The drive/IF 208 drives these cameras to capture the subject.

Figure 4:
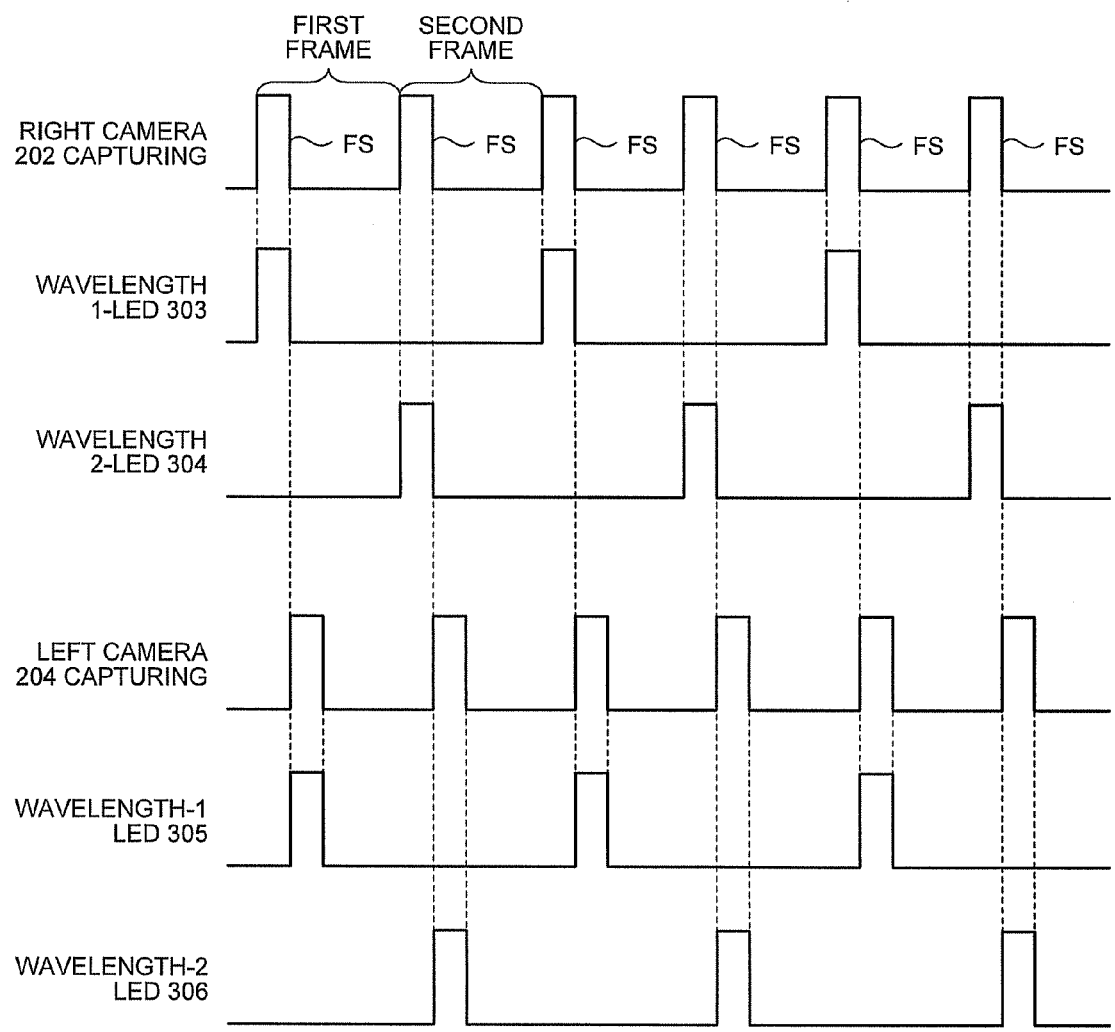
FIG. 4 is a diagram illustrating an example of a relationship between light emission timing of an infrared light source and capturing timing of right and left cameras.

FIG. 4 is a diagram illustrating an example of a relationship between light emission timing of the infrared light source and capturing timing of the right and left cameras. A frame synchronization signal FS is output from the right camera 202. The frame synchronization signal FS is output to the left camera 204 and the LED drive controller 316. Accordingly, in a first frame, right and left infrared light sources with a wavelength 1 (a wavelength 1-LED 303 and a wavelength 1-LED 305) are caused to emit light at shifted timing, and images by the right and left cameras (right camera 202 and left camera 204) are taken in, corresponding to the light emission. At a second frame, right and left infrared light sources with a wavelength 2 (a wavelength 2-LED 304 and a wavelength 2-LED 306) are caused to emit light at shifted timing, and images by the right and left cameras are taken in, corresponding to the light emission. Hereinafter, processing of the first frame and the second frame is repeated according to the frame synchronization signal FS.

Referring back to FIG. 3, the infrared LED light source 203 includes the wavelength 1-LED 303 and the wavelength 2-LED 304. The infrared LED light source 205 includes the wavelength 1-LED 305 and the wavelength 2-LED 306.

The wavelength 1-LEDs 303 and 305 perform irradiation with infrared rays of the wavelength 1. The wavelength 2-LEDs 304 and 306 perform irradiation with infrared rays of the wavelength 2.

The wavelength 1 and the wavelength 2 are a wavelength of less than 900 nm and a wavelength of 900 nm or more, respectively. When the pupil is irradiated with the infrared rays of the wavelength of less than 900 nm, and reflection light reflected at the pupil is captured, a brighter pupil image can be obtained, compared with a case where the pupil is irradiated with the infrared rays of the wavelength of 900 nm or more, and reflection light reflected at the pupil is captured. Note that wavelengths of the infrared rays to be irradiated are not limited to the above wavelengths, and any wavelengths may be used as long as a difference can be obtained between a result of a case where the pupil is irradiated with the infrared rays of the wavelength 1 and the reflection light reflected at the pupil is captured, and a result of a case where the pupil is irradiated with the infrared rays of the wavelength 2 and the reflection light reflected at the pupil is captured.

The speaker driver 322 drives the speaker 105. Note that the diagnosis supporting device 100 may include an interface (printer IF) for being connected with a printer as a print unit. Further, the printer may be included inside the diagnosis supporting device 100.

The controller 300 controls the entire diagnosis supporting device 100. The controller 300 includes an eye gaze detector 351, a gaze point detector 352, an output controller 353, and an evaluator 354. The controller 300 may be a control device such as a personal computer (PC).

The eye gaze detector 351 detects an eye gaze (eye gaze direction) of the subject, from the captured images captured by the imaging units (stereo cameras 102). Processing of detecting an eye gaze includes processing of detecting a position of an eye of the subject. The gaze point detector 352 detects a gaze point of the subject, using the detected eye gaze direction. The gaze point detector 352 detects a gaze point that is a point that the subject gazes at, of an object image displayed on the display screen 101. As an eye gaze detection method by the eye gaze detector 351, and a gaze point detection method by the gaze point detector 352, any conventionally used methods can be applied. Hereinafter, a case of detecting the eye gaze direction and the gaze point of the subject, using stereo cameras, similarly to Patent Literature 3, will be exemplarily described.

In this case, first, the eye gaze detector 351 detects the eye gaze direction of the subject, from the images captured by the stereo cameras 102. The eye gaze detector 351 detects the eye gaze direction of the subject, using the methods described in Patent Literatures 1 and 2, and the like, for example. To be specific, the eye gaze detector 351 obtains a difference between an image obtained such that the pupil is irradiated with the infrared rays of the wavelength 1 and captured, and an image obtained such that the pupil is irradiated with the infrared rays of the wavelength 2 and captured, and generates an image with a clarified pupil image. The eye gaze detector 351 calculates a position of the pupil of the subject (a position of the eye) by a stereoscopic technique, using two images generated as described above from the images captured by the right and left cameras (the right camera 202 and the left camera 204), respectively. Further, the eye gaze detector 351 calculates a position of a corneal reflection of the subject, using the images captured by the right and left cameras. The eye gaze detector 351 then calculates an eye gaze vector that indicates the eye gaze direction of the subject, from the position of the pupil of the subject and the corneal reflection position.

Note that a method of detecting the position of the eye of the subject and eye gaze is not limited to the above method. For example, the position of the eye of the subject and the eye gaze may be detected, by an analysis of an image captured using visible light, instead of the infrared rays.

The gaze point detector 352 detects an intersection point of the eye gaze vector expressed in a coordinate system like FIG. 1, and an XY plane, as the gaze point of the subject, for example. When the gaze point detector 352 can obtain eye gaze directions of both eyes, the gaze point detector 352 may measure the gaze point by obtaining an intersection point of the right and left eye gazes of the subject.

Figure 5:
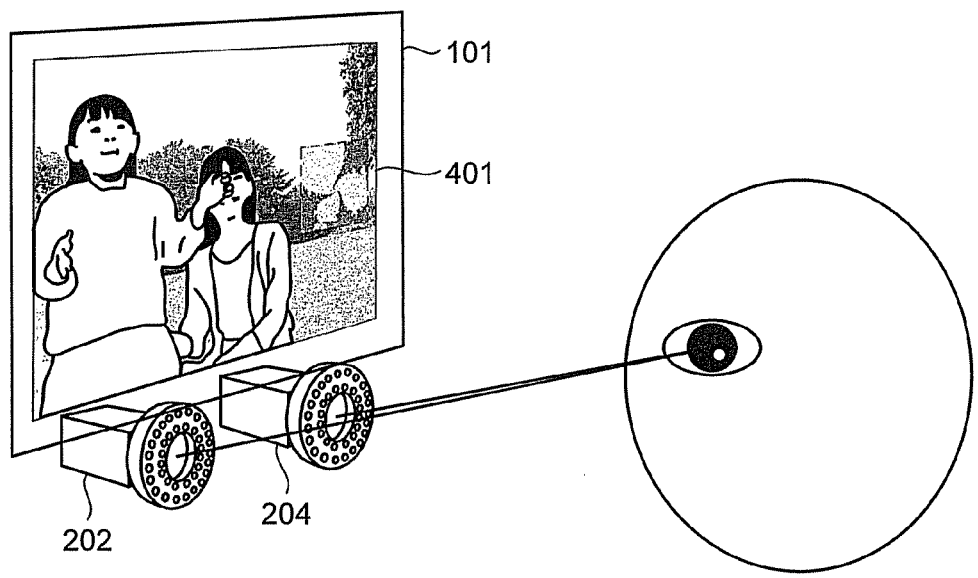
FIG. 5 is a diagram illustrating an example of detection of an eye and a distance of when two cameras are used.

FIG. 5 is a diagram illustrating an example of detection of an eye and a distance of when using the two cameras (the right camera 202 and the left camera 204). A camera calibration theory by a stereo calibration method is applied to the two cameras, and a camera parameter is obtained in advance. As the stereo calibration method, any conventionally used method such as a method using a camera calibration theory of Tsai can be applied. Three-dimensional coordinates of the eye in a world coordinate system can be obtained using the position of the eye detected from the image captured by the right camera 202, the position of the eye detected from the image captured by the left camera 204, and the camera parameter. Accordingly, the distance between the eye and the stereo cameras 102, and pupil coordinates can be estimated. The pupil coordinates are coordinate values that indicate the position of the eye (pupil) of the subject on the XY plane. The pupil coordinates can be coordinate values of projection of the position of the eye expressed in the world coordinate system into the XY plane, for example. Usually, the pupil coordinates of both the right and left eyes are obtained. A diagnosis image 401 is displayed on the display screen 101. As described below, the diagnosis image 401 includes a nature image displayed in a display region of the display screen 101, and a pattern image including a pattern similar to the nature image, displayed in a partial region included in the display region.

The pattern image is an image (geometric image) including one or more geometric patterns, for example. The nature image may just be an image of a natural object or an image that is associated with a natural object, other than the geometric image. For example, an image (a still image or a moving image) obtained by capturing of a person, an animal, a plant, a landscape of nature, or the like, with a camera, may be used as the nature image. Further, an image (a still image or a moving image) of a character that mimics a person or an animal may be used as the nature image.

Referring back to FIG. 3, the output controller 353 controls various types of information for the display 210 and the speaker 105. For example, the output controller 353 controls outputs of evaluation results by the diagnosis image 401 and the evaluator 354, and the like to the display 210. The output controller 353 displays a plurality of diagnosis images. For example, the output controller 353 may display a second diagnosis image on the display 210, after displaying a first diagnosis image on the display 210, the second diagnosis image being different from the first diagnosis image in a position of a pattern image, luminance, hue, chroma, and the like. In this case, the gaze point detector 352 detects respective gaze points of the subject of when the first diagnosis image and the second diagnosis image are displayed. By use of a plurality of diagnosis images, detection of a more accurate gaze point and diagnosis support become possible.

The evaluator 354 calculates an evaluation value, as an index related to the degree of developmental disorder, based on the diagnosis images and the gaze points detected by the gaze point detector 352. For example, the evaluator 354 calculates a ratio of a time to look at the nature image to a time to look at the pattern image, as the evaluation value, based on positions of the gaze points of the subject of when the diagnosis images of FIGS. 6 to 10 described below are displayed, and calculates the evaluation value that indicates that a possibility of developmental disorder is higher as the evaluation value is lower. The evaluator 354 may just calculate the evaluation value, based on the diagnosis images and the gaze points, and a calculation method thereof is not limited to the embodiment.

FIGS. 6 to 10 are explanatory diagrams illustrating examples of the diagnosis image 401 (401a to 401e) in the first embodiment. Note that, hereinafter, an example of using a moving image as the diagnosis image will be described. The diagnosis image is not limited to the moving image, and for example, a plurality of still images may be used as the diagnosis images. In the present embodiment, a picture in which a large part of a display region is occupied with a picture of persons (person picture) is used as the diagnosis image. A neurotypical subject has a strong tendency to look at such a picture by preference. A picture of a geometric pattern (geometric pattern picture) is displayed in a region F (partial region) that is a part of the person picture. A subject with developmental disorder has a strong tendency to look at a geometric pattern by preference. As a result of experiments, it has been confirmed that the subject with developmental disorder looks at a fractal picture by a Julia set, a Mandelbrot set, or the like, by preference. The subject with developmental disorder has a strong tendency to look at the geometric pattern image by preference. However, when the person image and the geometric image are similar, the subject with developmental disorder may not notice the geometric pattern image. Therefore, the present embodiment employs a configuration to cause the geometric pattern image to stand out in the diagnosis image in a diagnosis start period, so as to cause the subject with developmental disorder to notice the geometric pattern image. Note that an example of the portion of the natural image (including the person image) and the geometric pattern image being similar include a color, luminance, chroma, or the like being similar as described below.

An important thing here is that the picture of the region F substantially stands out in a period immediately after start of diagnosis (hereinafter, the period may be referred to as diagnosis period A) against the surrounding person picture. A subject with normal development has a strong tendency to look at the surrounding person picture by preference. Therefore, even if attention is drawn to the geometric pattern image first, the subject with normal development tends to look at the surrounding person picture in a diagnosis period after some time has passed from the start of diagnosis (the diagnosis period is a period after the diagnosis period A is terminated, hereinafter, may be called diagnosis period B). In the diagnosis period B, the geometric pattern image is caused not to stand out, compared with the period immediately after the start of diagnosis, so that the subject with normal development further tends to look at the surrounding person picture. Meanwhile, the subject with developmental disorder has a strong tendency to prefer the geometric pattern image. Therefore, to inform existence of the geometric pattern image, the geometric pattern image is caused to stand out in the period immediately after the start of diagnosis. Once the subject with developmental disorder notices the geometric pattern, the subject with developmental disorder has a strong tendency to continuously look at the geometric pattern image even when the geometric pattern picture does not stand out compared with the surrounding person picture by an increase in the degree of similarity between the natural image and the geometric pattern image in the diagnosis period B. Therefore, in the diagnosis period B, a difference between a ratio of looking at the geometric pattern image of the subject with normal development and a ratio of looking at the geometric pattern image of the subject with developmental disorder becomes large.

Figure 6:
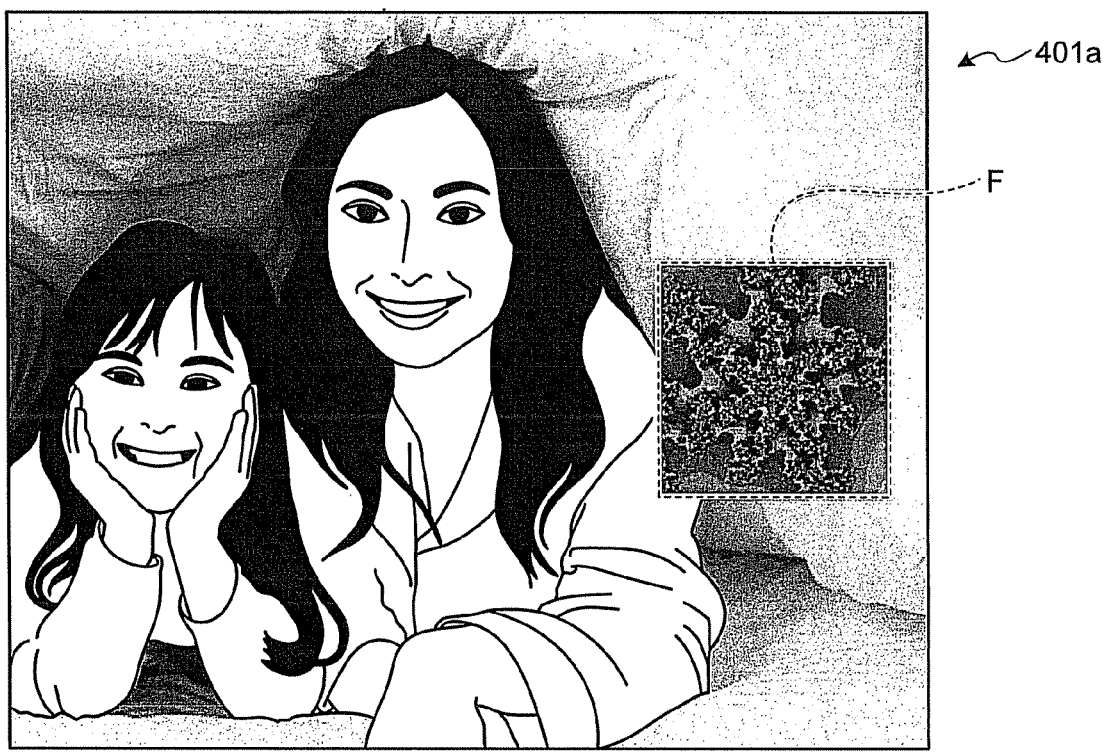
FIG. 6 is a diagram illustrating an example of a diagnosis image in the first embodiment.
Figure 7:
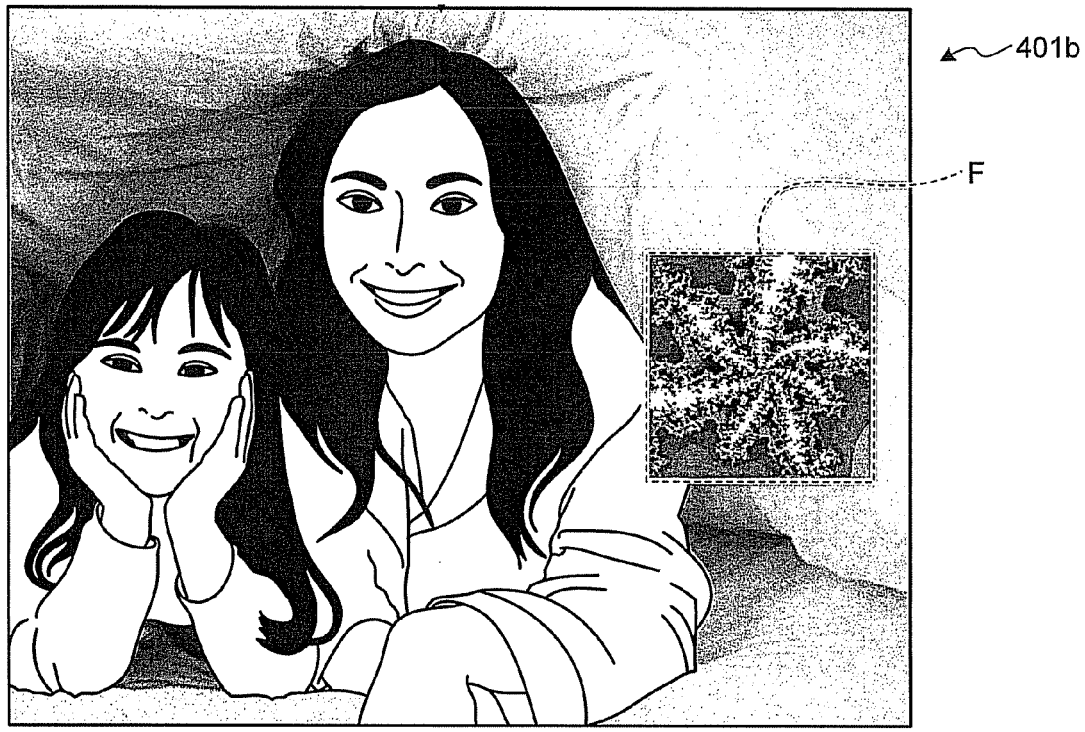
FIG. 7 is a diagram illustrating an example of a diagnosis image in the first embodiment.
Figure 8:
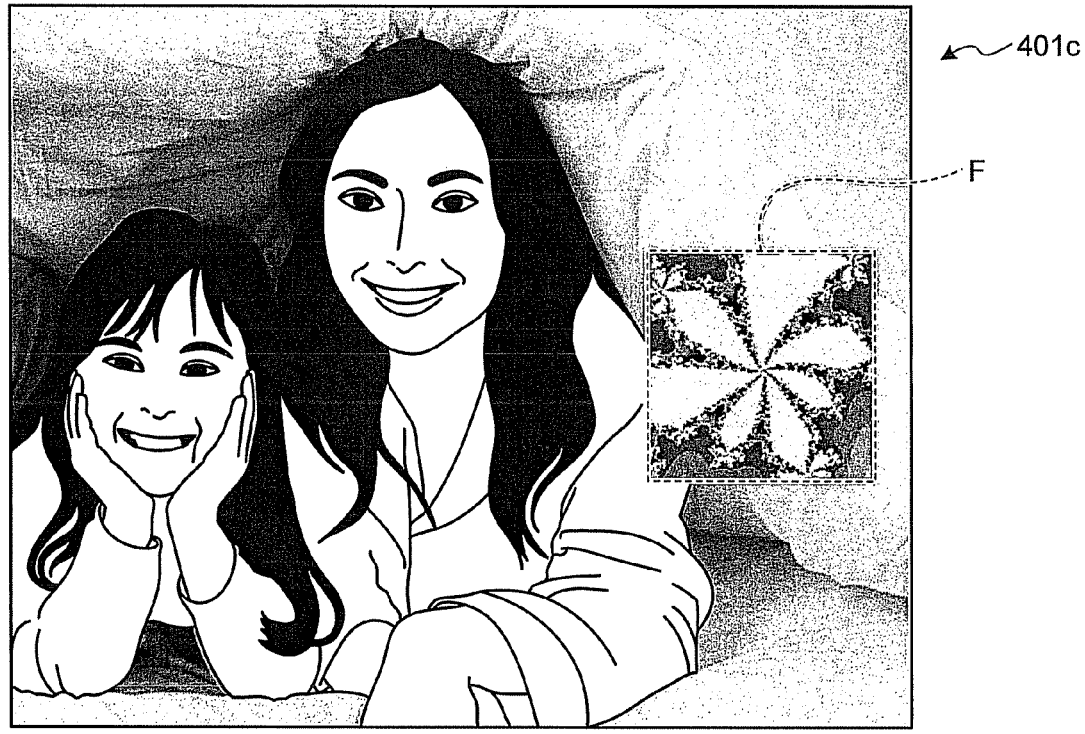
FIG. 8 is a diagram illustrating an example of a diagnosis image in the first embodiment.
Figure 9:
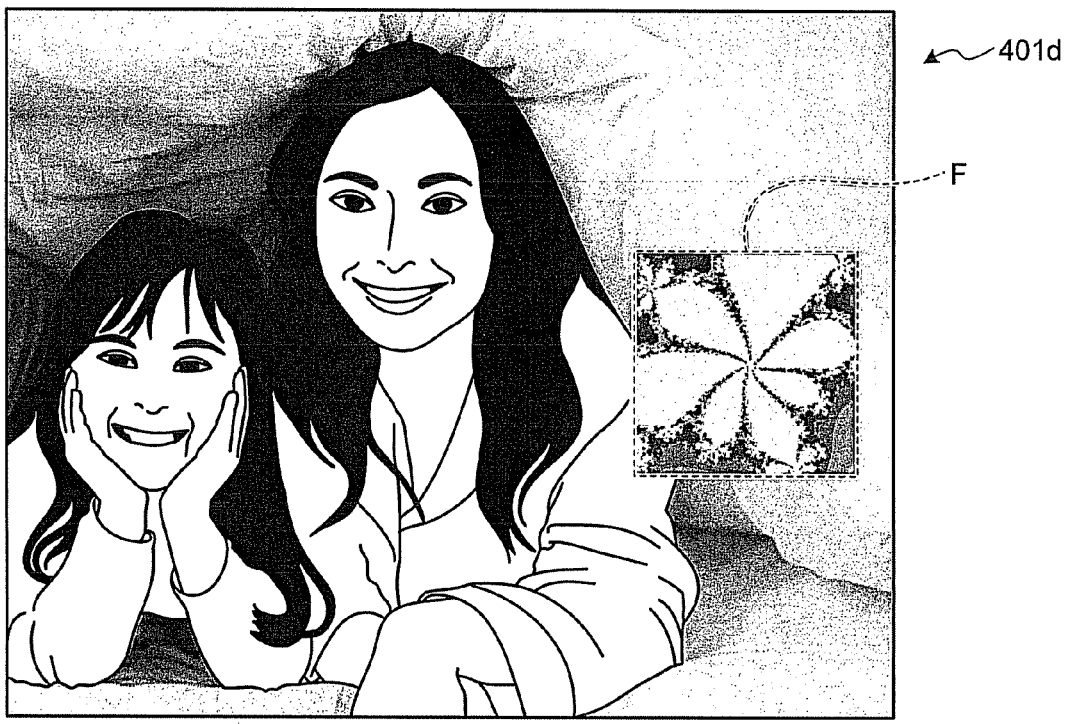
FIG. 9 is a diagram illustrating an example of a diagnosis image in the first embodiment.
Figure 10:
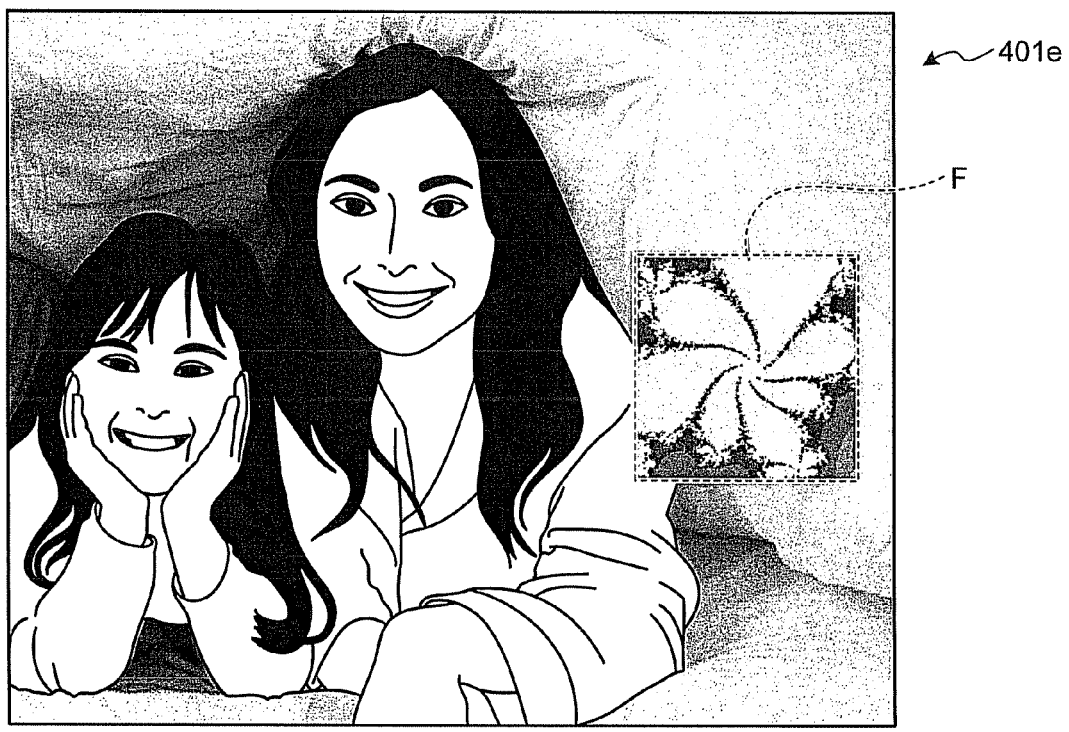
FIG. 10 is a diagram illustrating an example of a diagnosis image in the first embodiment.
Figure 11:
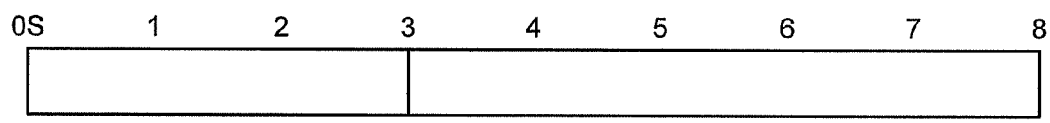
FIG. 11 is a diagram illustrating an example of a time chart of when a diagnosis picture in the first embodiment is displayed.

FIGS. 6 to 10 are continuously changed diagnosis images in the time chart of FIG. 11. FIG. 6 illustrates a picture of at the time of start of display (0 seconds), FIG. 7 illustrates the picture of after 2 seconds, FIG. 8 illustrates the picture of after 3 seconds, FIG. 9 illustrates the picture of after 6 seconds, and FIG. 10 illustrates the picture of after 8 seconds. Note that these times are examples. In the time chart of FIG. 11, the picture as a whole is an 8-second picture. 3 seconds immediately after the start of diagnosis (the diagnosis period A, FIGS. 6 to 8) are a period in which the difference between the natural image and the geometric pattern image in the diagnosis image is large (the degree of similarity is low), and later 3 to 8 seconds (the diagnosis period B, FIGS. 8 to 10) are a period in which the difference between the natural image and the geometric pattern image in the diagnosis image is small (the degree of similarity is high). An example of the difference between the natural image and the geometric pattern image in the diagnosis image being large (the degree of similarity being low) include a case where a difference in a color, luminance, or chroma between the natural image and the geometric pattern image is large. For the difference between the natural image and the geometric pattern image, a part of the natural image and the geometric pattern image may be compared. Further, a change amount of a plurality of geometric pattern images included in the diagnosis period A is compared with a change amount of a plurality of geometric pattern images included in the diagnosis period B, and the difference between change amounts may be caused to become large. As an example, the geometric pattern image is compared with an immediately previous geometric pattern image, and the color, luminance, or chroma is largely changed over time, or when the geometric pattern image is provided as a moving image, the change amount of the picture (rotation or the like) may be caused to become large. As described above, in the display period (diagnosis period A) immediately after the start of diagnosis, the geometric pattern image is caused to stand out so that the subject can notice the geometric pattern image, by making the difference in a color, luminance, or chroma between the natural image and the geometric pattern image large, or making the change amount of the geometric pattern image large. On the other hand, in the diagnosis period B that is the period after the diagnosis period A, the geometric pattern image in the diagnosis image is caused not to stand out, by making the difference in a color, luminance, or chroma between the natural image and the geometric pattern smaller than the diagnosis period A (making the degree of similarity higher), or making the change amount smaller than the diagnosis period A. In the diagnosis period B, it is favorable that the difference between the natural image and the geometric pattern image to fall within a following range. In a Munsell color system, in a case of hue, the range is within adjacent three colors of an appropriate color in a case of 20 colors of the Munsell hue circle. For example, a range of similarity of red covers reddish purple, red purple, purplish red, yellowish red, yellow red, and reddish yellow. In the Munsell color system, as for luminance (value), the range is within three in a difference of value. As for chroma, the range is within six in a difference of chroma.

Note that, in the time chart of FIG. 11, the change amount of the diagnosis image is largely changed on 3 seconds. However, the change amount may be gradually changed over time.

Figure 12:
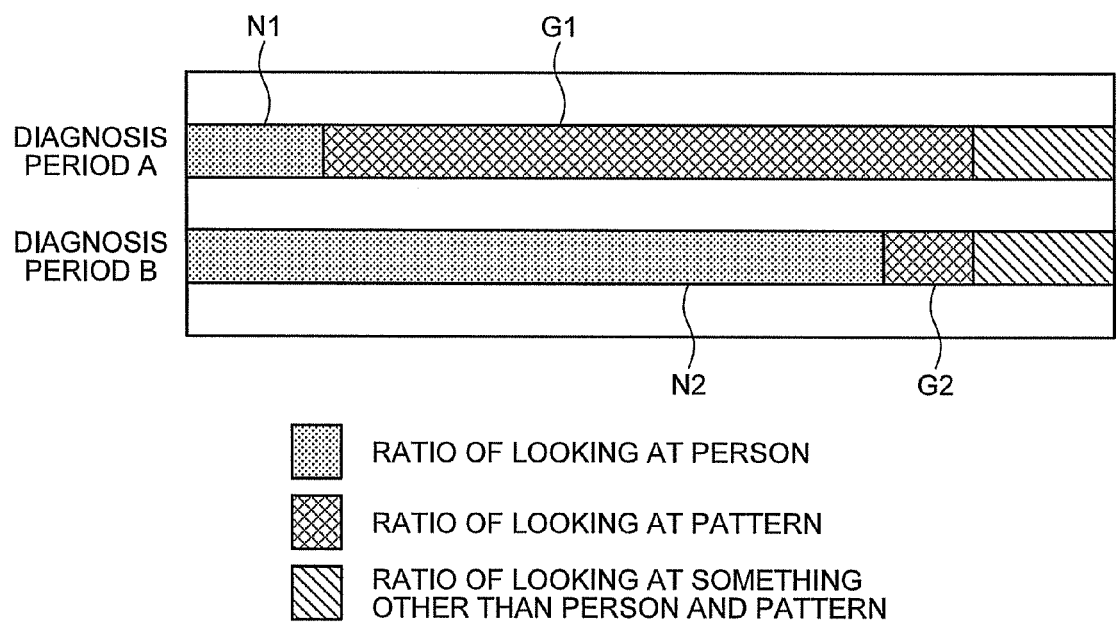
FIG. 12 is a diagram illustrating ratios of gaze point positions of a neurotypical subject in the first embodiment.

FIG. 12 is a diagram illustrating an example of a ratio of a gaze point position of when the neurotypical subject views the diagnosis image with the present device. The upper part of FIG. 12 illustrates a ratio of a gaze point position of the subject from the start of diagnosis to the elapse of 3 seconds in the diagnosis period A. The lower part of FIG. 12 illustrates a ratio of a gaze point position of the subject from the elapse of 3 seconds to the elapse of 8 seconds in the diagnosis period B. The neurotypical subject has a larger ratio (G1) of gazing at the geometric pattern than a ratio (N1) of gazing at the persons (nature image) in the diagnosis period A, and has a larger ratio (N2) of gazing at the persons (nature image) than a ratio (G2) to look at the geometric pattern in the diagnosis period B.

Figure 13:
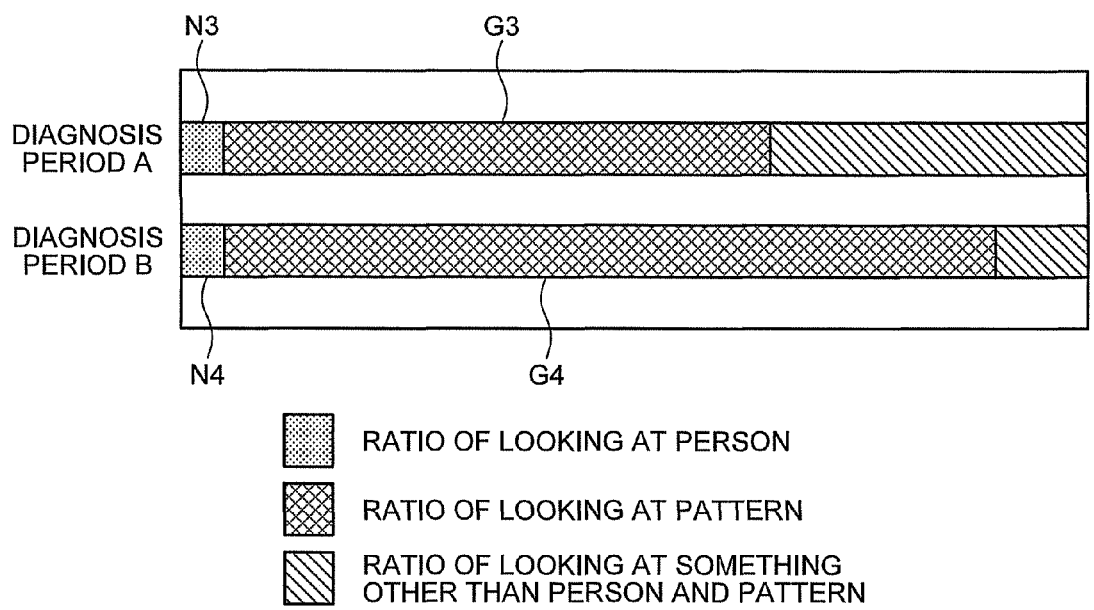
FIG. 13 is a diagram illustrating ratios of gaze point positions of a subject having developmental disorder in the first embodiment.

FIG. 13 illustrates an example of a ratio of a gaze point position of when the subject with developmental disorder views the diagnosis image with the present device. The upper part of FIG. 13 illustrates a ratio of a gaze point position of the subject from the start of diagnosis to the elapse of 3 seconds in the diagnosis period A. The lower part of FIG. 13 illustrates a ratio of a gaze point position of the subject from the elapse of 3 seconds to the elapse of 8 seconds in the diagnosis period B. The subject with developmental disorder has a large ratio (G3) of gazing at the geometric pattern in the diagnosis period A, and has a larger ratio (G4) of gazing at the geometric pattern image in the diagnosis period B. Further, the subject with developmental disorder has a small ratio (N3) of gazing at the persons (nature image) in the diagnosis period A and has a small ratio (N4) of gazing at the persons (nature image) in the diagnosis period B.

Comparing the neurotypical subject and the subject with developmental disorder, a difference in the ratio of gazing at the geometric pattern in the diagnosis period B (a difference between G2 of FIG. 12 and G4 of FIG. 13) is large. Therefore, check of the ratio of gazing at the geometric pattern in the diagnosis period B is one of guidelines of discrimination of the neurotypical subject and the subject with developmental disorder.

Figure 14:
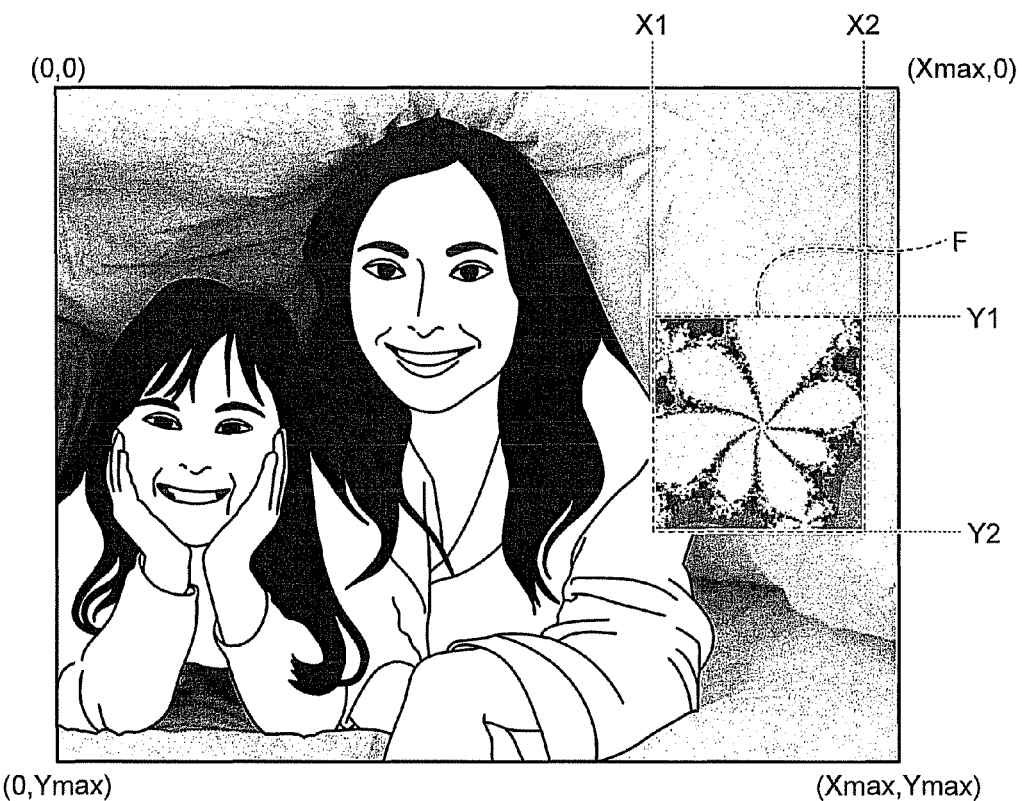
FIG. 14 is an example of a diagnosis image in the first embodiment.

FIG. 14 is an explanatory diagram about coordinates of an image displayed on the display 210. For description, in the coordinate system on the display 210, an upper left position is the origin, a coordinate in an up and down direction is a Y coordinate (the down direction is +), and a coordinate in a transverse direction is an X coordinate (the right direction is +). For convenience of description, these coordinates are different from the above-described world coordinates (space coordinates) for gaze point detection.

In the example of FIG. 14, the number of pixels of the display 210 is Xmax×Ymax. The X coordinate of a left side of the region F is X1, the X coordinate of a right side is X2, the Y coordinate of an upper side is Y1, and the Y coordinate of a lower side is Y2. Details of diagnosis processing using these pictures and coordinates will be described using flowcharts of FIGS. 16 to 18 (below).

Figure 15:
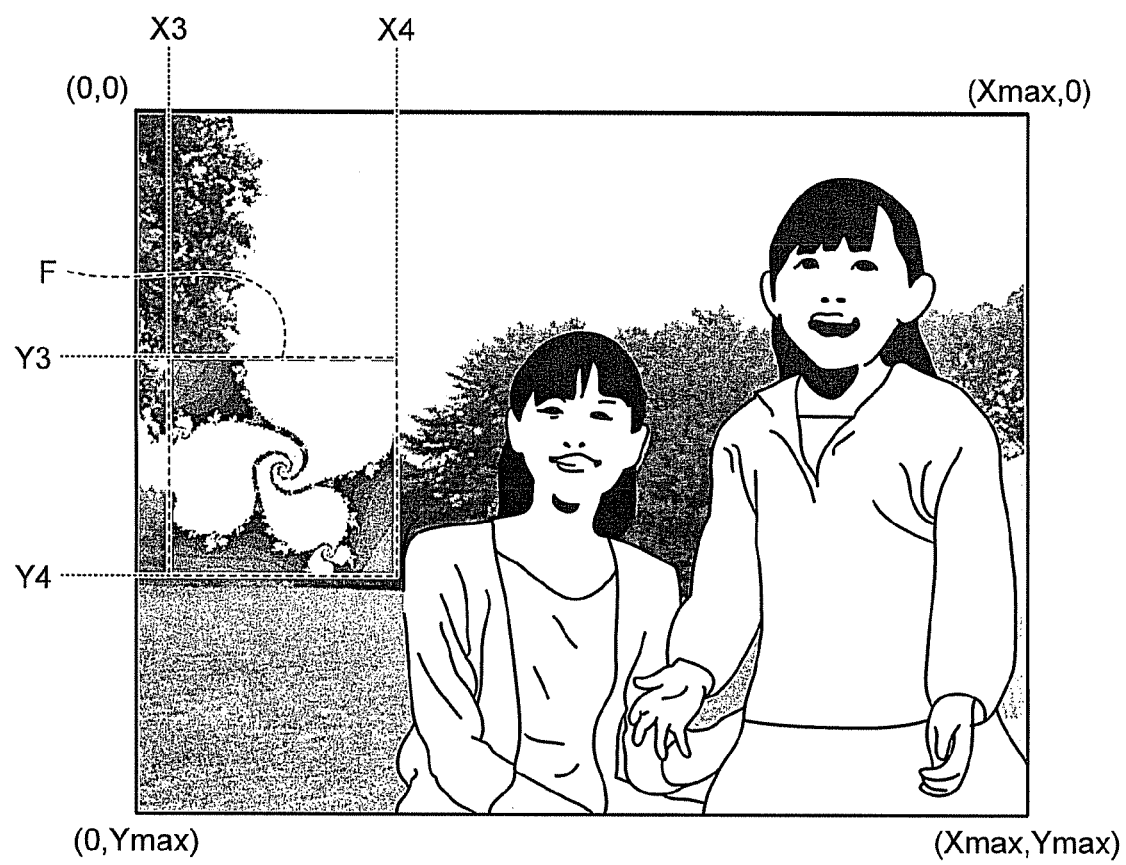
FIG. 15 is an example of a diagnosis image in the first embodiment.

FIG. 15 is a diagram illustrating an example of a picture (diagnosis picture) different from the pictures (FIGS. 6 to 11, and 14) used in the description so far. In the diagnosis picture of FIG. 15, contents of the picture and the image region of the geometric pattern are different from the images of FIGS. 6 to 10, and 14. Note that, between FIG. 15, and FIGS. 6 to 10, and 14, at least the position of the region of the geometric pattern image may just be different.

In FIG. 15, the X coordinate of the left side of the region F is X3, the X coordinate of the right side is X4, the Y coordinate of the upper side is Y3, and the Y coordinate of the lower side is Y4. Details of diagnosis processing using these picture and coordinates will be described using flowcharts of FIGS. 16 to 18 (below).

Note that, between FIG. 14 and FIG. 15, the positions of the regions F of the respective diagnosis images are different. To be specific, the positions are point symmetry having a center of the display region of the display screen 101 as a point of symmetry. With such display, diagnosis of a tendency of viewing of the subject, such as from which direction the subject views the screen, becomes possible, and diagnosis can be performed excluding such a tendency of the viewer.

Figure 16:
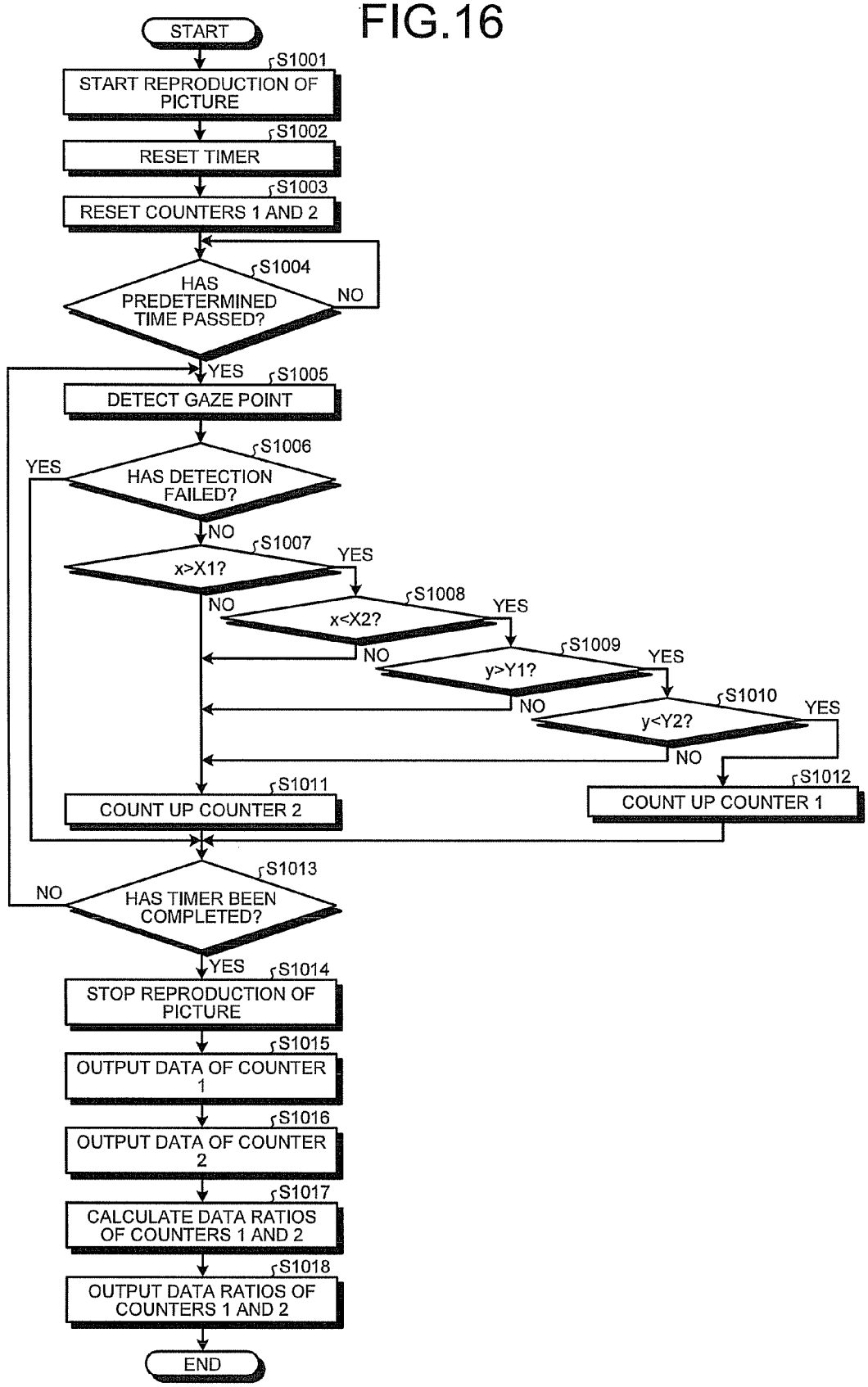
FIG. 16 is a flowchart illustrating an example of diagnosis supporting processing in the first embodiment.
Figure 17:
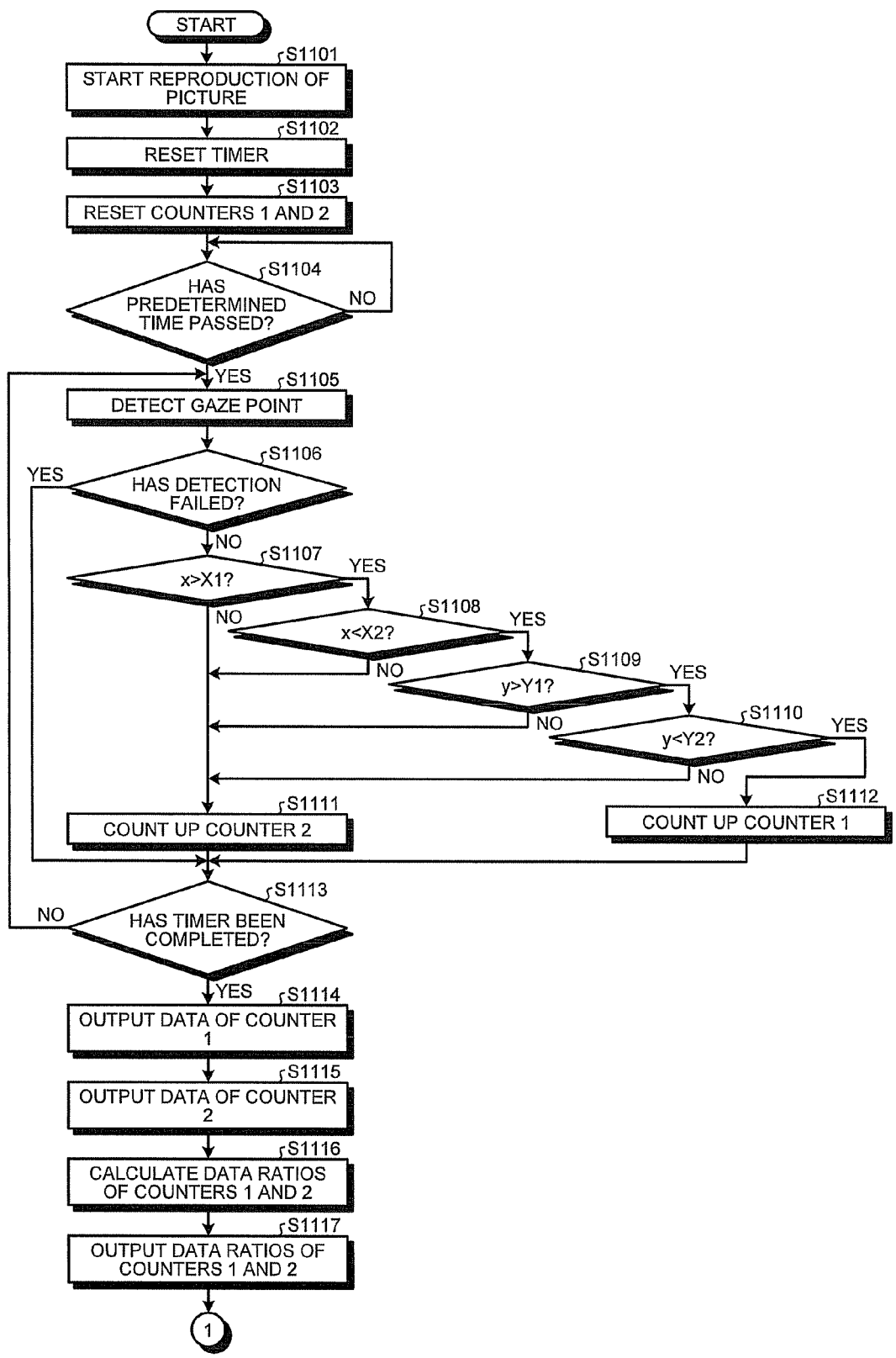
FIG. 17 is a flowchart illustrating an example of the diagnosis supporting processing in the first embodiment.
Figure 18:
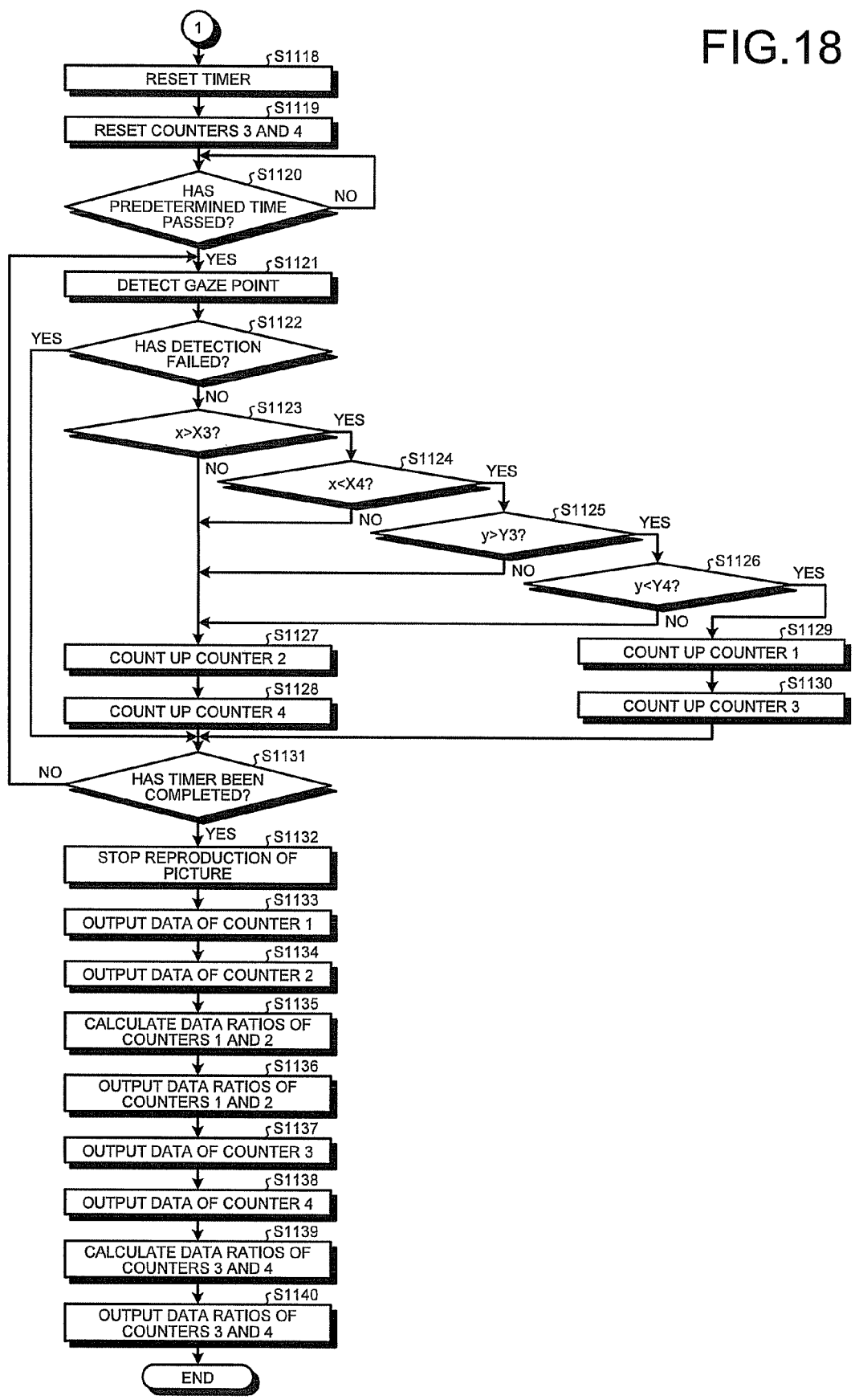
FIG. 18 is a flowchart illustrating an example of the diagnosis supporting processing in the first embodiment.

Next, diagnosis supporting processing by the diagnosis supporting device 100 according to the first embodiment configured as described above will be described using FIGS. 16 to 18. FIGS. 16 to 18 are flowcharts illustrating an example of diagnosis supporting processing in the present embodiment.

First, a flowchart of performing diagnosis support with one picture will be described using FIG. 16. One picture is, for example, the continuously changed diagnosis images displayed in the time chart of FIG. 11, which is configured from a plurality of diagnosis images as illustrated in FIGS. 6 to 10, for example. FIG. 6 illustrates the picture of at the time of start of display, FIG. 7 illustrates the picture of after 2 seconds, FIG. 8 illustrates the picture of after 3 seconds, FIG. 9 illustrates the picture of after 6 seconds, and FIG. 10 illustrates the picture of after 8 seconds. Here, FIGS. 6 and 7 illustrate the picture (first diagnosis image) displayed in the period immediately after the start of diagnosis (diagnosis period A), and FIGS. 9 and 10 illustrate the picture (second diagnosis image) displayed in the period after a predetermined period has passed from the start of diagnosis (diagnosis period B). The diagnosis image (second diagnosis image) displayed in the diagnosis period B has a characteristic that the portion of the natural image and the geometric pattern image are similar, compared with the diagnosis image (first diagnosis image) displayed in the diagnosis period A. Hereinafter, the nature image (including the person picture) and the geometric pattern picture are composited in advance.

First, the controller 300 starts reproduction of the picture (step S1001). Next, the controller 300 resets a timer that measures a slightly shorter time than a reproduction time of the picture (step S1002). Next, the controller 300 resets a counter 1 that is counted up when the subject gazes at an inside of the region F, and a counter 2 that is counted up when the subject gazes at an outside of the region F (step S1003). Next, the controller 300 confirms whether a predetermined time (3 seconds) has passed (step S1004). When the predetermined time has passed, the processing proceeds to the next step. The period from the start of reproduction of the picture to the elapse of the predetermined time corresponds to the above-described diagnosis period A.

Note that gaze point measurement described below is performed in each one frame of the stereo cameras 102 that perform capturing in synchronization with each other. That is, the gaze point is measured in every predetermined time interval. Therefore, count values of the counter 1 and the counter 2 respectively correspond to the gaze times of inside and outside the region F.

Next, the eye gaze detector 351 and the gaze point detector 352 detect the gaze point (step S1005). Next, the controller 300 determines whether the gaze point detection has failed (step S1006). For example, when the images of the pupil and the corneal reflection cannot be obtained due to a blink or the like, the gaze point detection fails. Further, when the gaze point does not exist in the screen of the display 210 (or when the subject looks at something other than the screen of the display 210), the gaze point detection fails.

When the gaze point detection has failed (Yes in step S1006), the controller 300 skips processing from step S1007 to step S1012 so as not to influence the counters 1 and 2, and moves onto step S1013.

When the gaze point detection has succeeded (No in step S1006), the controller 300 checks whether an X coordinate "x" of the gaze point on the display 210 is larger than X1 (step S1007). When "x" is larger than X1 (Yes in step S1007), the controller 300 checks whether "x" is smaller than X2 (step S1008). When "x" is smaller than X2 (Yes in step S1008), the controller 300 checks whether a Y coordinate "y" of the gaze point on the display 210 is larger than Y1 (step S1009). When "y" is larger than Y1 (Yes in step S1009), the controller 300 checks whether "y" is smaller than Y2 (step S1010). When "y" is smaller than Y2 (Yes in step S1010), the gaze point exists in the region F. Therefore, the controller 300 counts up the counter 1 (step S1012). When "y" is not smaller than Y2 (No in step S1010), the subject has looked at the person picture or the like outside the region F. Therefore, the controller 300 counts up the counter 2 (step S1011). Similarly, when "x" is not larger than X1 (No in step S1007), when "x" is not smaller than X2 (No in step S1008), and when "y" is not larger than Y1 (No in step S1009), the controller 300 counts up the counter 2 (step S1011).

Next, to confirm end of the picture, the controller 300 checks completion of the timer (step S1013). For example, the controller 300 determines that the timer has been completed when the value of the timer has reached a predetermined value corresponding to a termination time of the picture. When the timer has not been completed (No in step S1013), the controller 300 returns to step S1005, and repeats the processing.

When the timer has been completed (Yes in step S1013), the controller 300 stops the reproduction of the picture (step S1014). A period after the elapse of a predetermined time in step S1004 to completion of the timer in step S1013 corresponds to the diagnosis period B. Next, the controller 300 outputs data (a value) of the counter 1 (step S1015). The data of the counter 1 corresponds to the gaze time of the inside of the region F. Next, the controller 300 outputs data (a value) of the counter 2 (step S1016). The data of the counter 2 corresponds to the gaze time of the outside of the region F. Next, the evaluator 354 calculates ratios of the counter 1 and the counter 2 (step S1017). The evaluator 354 outputs a calculated evaluation value (step S1018). For example, the evaluator 354 calculates the evaluation value that indicates a ratio of the value of the counter 1 to the value of the counter 2. Such an evaluation value serves as a guideline of a possibility of developmental disorder. Note that a method of calculating the evaluation value is not limited to the above method. Any evaluation value may be used as long as the value can be used to determine whether the subject gazes at either the nature image or the pattern image. As the ratio of gazing at the region F is higher, the possibility that the subject has developmental disorder becomes higher.

FIGS. 17 and 18 illustrate flowcharts of when diagnosis support is performed with two pictures. The two pictures illustrated in FIGS. 17 and 18 are diagnosis pictures displayed in the time chart of FIG. 11, respectively. The first picture of the two pictures is a picture 1. Here, the picture 1 is the continuously changed diagnosis images displayed in the time chart of FIG. 11. In the time chart of FIG. 11, FIG. 6 illustrates the picture of at the time of start of display, FIG. 7 illustrates the picture of after 2 seconds, FIG. 8 illustrates the picture of after 3 seconds, FIG. 9 illustrates the picture of after 6 seconds, and FIG. 10 illustrates the picture of after 8 seconds. Here, FIGS. 6 and 7 illustrate the picture (first diagnosis image) displayed in the period immediately after the start of diagnosis (diagnosis period A), and FIGS. 9 and 10 illustrate the picture (second diagnosis image) displayed in the period after the elapse of a predetermined period from the start of diagnosis (diagnosis period B). The diagnosis image (second diagnosis image) displayed in the diagnosis period B has a characteristic that the portion of the natural image and the geometric pattern image are similar, compared with the diagnosis image (first diagnosis image) displayed in the diagnosis period A.

Next, the second picture of the two pictures is a picture 2. Here, the picture 2 is the continuously changed diagnosis images displayed in the time chart of FIG. 11. The picture 2 is different in at least the position of the region of the geometric pattern, as illustrated in FIGS. 14 and 15. For example, the diagnosis image is different from FIG. 6 in the position of the region of the geometric pattern at the time of start of display, the diagnosis image is different from FIG. 7 in the position of the region of the geometric pattern after 2 seconds, the diagnosis image is different from FIG. 8 in the position of the region of the geometric pattern after 3 seconds, the diagnosis image is different from FIG. 9 in the position of the region of the geometric pattern after 6 seconds, and the diagnosis image is different from FIG. 10 in the position of the region of the geometric pattern after 9 seconds. As an example, these diagnosis images are similar to FIGS. 6 to 10, respectively, other than the position of the region of the geometric pattern image. The diagnosis image provided in a period corresponding to the diagnosis period A is a third diagnosis image, and the diagnosis image provided in a period corresponding to the diagnosis period B is a fourth diagnosis image. The diagnosis image (fourth diagnosis image) displayed in the diagnosis period B has a characteristic that the portion of the natural image and the geometric pattern image are similar, compared with the diagnosis image (third diagnosis image) displayed in the diagnosis period A. Similarly to FIG. 16, the nature image (including the person picture) and the geometric pattern picture are composited in advance. The picture 1 (the first diagnosis image and the second diagnosis image) and the picture 2 (the third diagnosis image and the fourth diagnosis image) may be connected and one continuous picture. The picture 1 and the picture 2 are respectively configured from predetermined times corresponding to the diagnosis period A and the diagnosis period B.

FIG. 17 corresponds to processing of displaying the first picture (picture 1) of the two pictures. Steps S1101 to S1113 are similar to steps S1001 to S1013 of FIG. 16. In FIG. 17, reproduction of the picture is not stopped, and thus the processing corresponding to step S1014 of FIG. 16 is deleted. From steps S1114 to S1117 are similar to steps S1015 to S1018 of FIG. 16. Note that roles of the counter 1 and the counter 2 in this example are different from FIG. 16.

In FIGS. 17 and 18, the counter 1 and the counter 2 are counters that are counted through a time of reproduction of the picture 1 (first diagnosis picture) and the picture 2 (second diagnosis picture) that are the two pictures. That is, the counter 1 and the counter 2 perform counting of the two pictures as a whole. However, at the time of termination of the picture 1, a count result and a ratio of the picture 1 are output (steps S1114 to S1117). Following that, the counting is continuously performed in the picture 2, and a total value is output (steps S1133 to S1136).

FIG. 18 will be described. FIG. 18 corresponds to processing of displaying the second picture (picture 2) of the two pictures. Immediately before step S1118, reproduction of the picture 2 is started.

The controller 300 resets a timer that measures a slightly shorter time than a reproduction time of the picture 2 (step S1118). Next, the controller 300 resets a counter 3 that is counted up when the subject gazes at the inside of the region F in the picture 2, and a counter 4 that is counted up when the subject gazes at outside the region F (step S1119). Next, the controller 300 confirms whether a predetermined time (3 seconds) has passed (step S1120). When the predetermined time has passed, the controller 300 moves onto the next step.

Next, the eye gaze detector 351 and the gaze point detector 352 perform gaze point detection (step S1121). Next, the controller 300 determines whether the gaze point detection has failed (step S1122).

When the gaze point detection has failed (Yes in step S1122), the controller 300 skips processing of steps S1123 to S1130 so as not to influence the counters 3 and 4, and moves onto step S1131.

When the gaze point detection has succeeded (No in step S1122), the controller 300 checks whether an X coordinate "x" of the gaze point on the display 210 is larger than X3 (step S1123). When "x" is larger than X3 (Yes in step S1123), the controller 300 checks whether "x" is smaller than X4 (step S1124). When "x" is smaller than X4 (Yes in step S1124), the controller 300 checks whether a Y coordinate "y" of the gaze point on the display 210 is larger than Y3 (step S1125). When "y" is larger than Y3 (Yes in step S1125), the controller 300 checks whether "y" is smaller than Y4 (step S1126). When "y" is smaller than Y4 (Yes in step S1126), the gaze point exists inside the region F. Therefore, the controller 300 counts up the counter 1 (step S1129, and counts up the counter 3 (step S1130). When "y" is not smaller than Y4 (No in step S1126), the subject has looked at the person picture or the like other than the region F. Therefore, the controller 300 counts up the counter 2 (step S1127), and counts up the counter 4 (step S1128).

Next, to confirm end of the picture, the controller 300 checks completion of the timer (step S1131). When the timer has not been completed (No in step S1131), the controller 300 returns to step S1121, and repeats the processing.

When the timer has been completed (Yes in step S1131), the controller 300 stops the reproduction of the picture (step S1132). Next, the controller 300 outputs data of the counter 1 (step S1133). The data of the counter 1 corresponds to the gaze time of the inside of the region F of when the picture 1 and the picture 2 are reproduced. Next, the controller 300 outputs data of the counter 2 (step S1134). The data of the counter 2 corresponds to the gaze time of the outside of the region F of when the picture 1 and the picture 2 are reproduced. Next, the evaluator 354 calculates an evaluation value that indicates ratios of the counter 1 and the counter 2 (step S1135). The evaluator 354 outputs the evaluation value (step S1136).

Further, the evaluator 354 outputs data of the counter 3 (step S1137). The data of the counter 3 corresponds to the gaze time of the inside of the region F in the picture 2. Next, the evaluator 354 outputs data of the counter 4 (step S1138). The data of the counter 4 corresponds to the gaze time of the outside of the region F in the picture 2. Next, the evaluator 354 calculates an evaluation value that indicates ratios of the counter 3 and the counter 4 (step S1139). The evaluator 354 outputs the evaluation value (step S1140).

By comparison of the count result and the ratio of the picture 1 (steps S1114 to S1117), and the count result and the ratio of the picture 2 (steps S1137 to S1140), the tendency of the subject can be obtained. For example, when the subject has a tendency to look at the picture from the right side of the screen, there is a tendency that the count value in the region F is increased in the picture 1, and the count value in the region F is decreased in the picture 2. When the subject looks at the picture in a right and left balanced manner, it can be considered that the subject gazes at the picture according to his/her liking after starting to look at a central portion.

In the first embodiment, use of the tendency of the subject to gaze at the screen, for the evaluation using the picture 1 and the picture 2, has been described. As for the evaluation value that indicates the ratio of gazing at the region F, a larger value or a smaller value may be employed as a final evaluation value, using the picture 1 and the picture 2. Alternatively, the final evaluation value may be obtained by taking an average of two evaluation values.

As described above, according to the first embodiment, effects as follows can be obtained, for example:

(1) A geometric pattern image is arranged in a person picture, a portion of the geometric pattern and a picture portion other than the region having a close display form of the luminance, hue, and chroma are combined, and the shape of the portion of the geometric pattern is caused to be gradually changed. Accordingly, while the neurotypical subject becomes hard to notice the region, the subject with developmental disorder can adequately find out the region. Therefore, the difference in the gaze points becomes larger than a conventional case, and detection accuracy is improved.

(2) A geometric pattern region around the center of the screen is measured several times while being point-symmetrically changed. Accordingly, a tendency of a subject to look at a specific direction can be offset.

The diagnosis images and the diagnosis processing are not limited to the above embodiment. In the following first to third modifications, other examples of diagnosis images, and examples of diagnosis processing using the diagnosis images will be described.

(First Modification)

In the first modification, an output controller 353 displays at least two of a person image, a geometric image, and a character image in mutually different divided regions, of a plurality of divided regions, as diagnosis images, respectively. The divided regions indicate divided display regions (divided display screens 101) of a display 210. A specific example of the divided regions will be described below.

An evaluator 354 calculates an evaluation value based on at least one of a moved distance of a gaze point in a predetermined period, a moving speed of the gaze point in a predetermined period, the number of the gaze points detected in a divided region in a predetermined period, and the number of times of movement of the gaze point among a plurality of divided regions in a predetermined period, based on a position of the gaze point of a subject of when a diagnosis image like FIG. 5 described below is displayed, for example.

Figure 19:
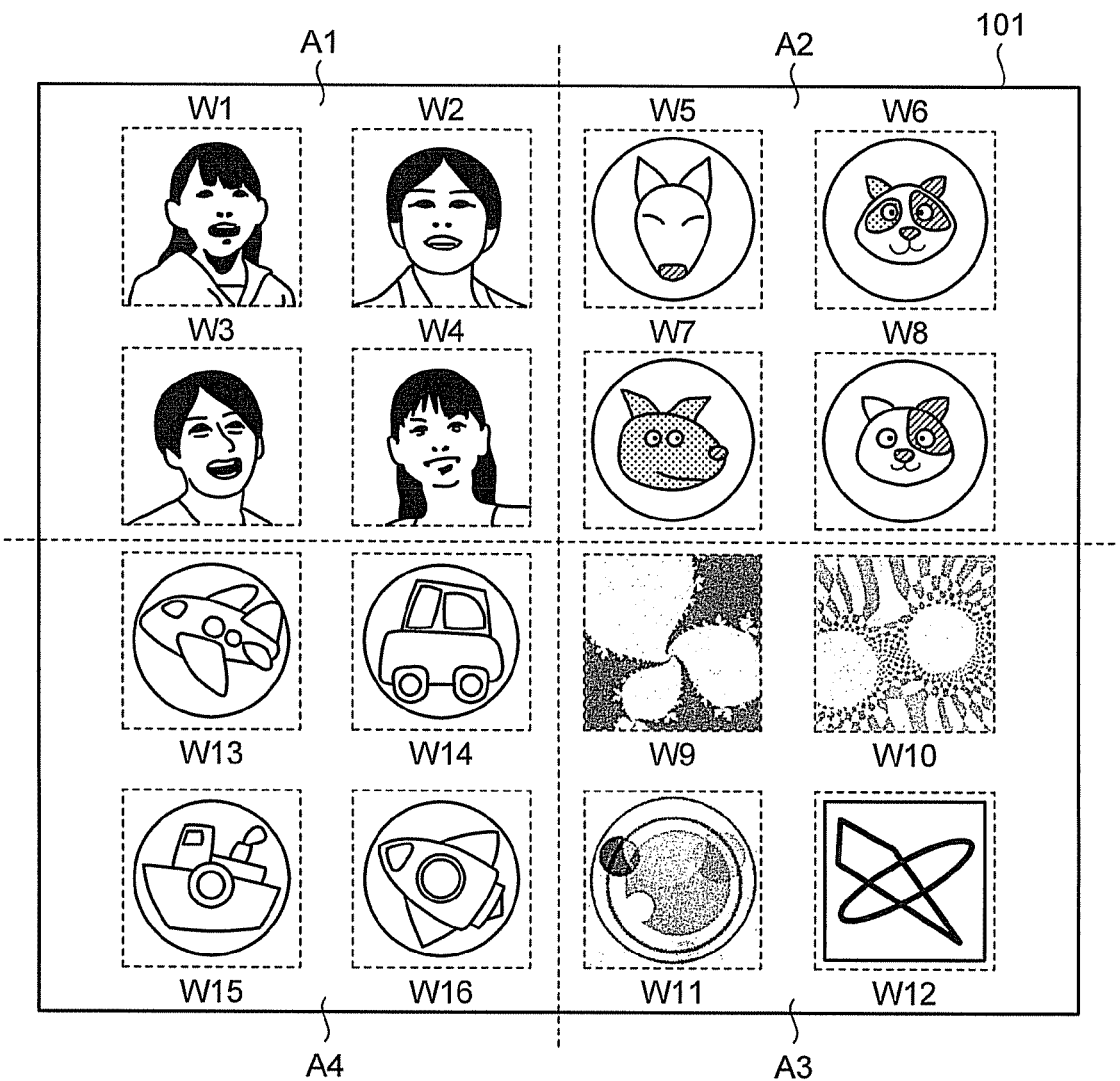
FIG. 19 is an explanatory diagram illustrating an example of a diagnosis image displayed in a first modification.

FIG. 19 is an explanatory diagram illustrating an example of a diagnosis image to be displayed. As illustrated in FIG. 19, the display screen 101 is divided into a plurality of divided regions. Hereinafter, the divided regions are also referred to as areas. In the example of FIG. 19, the display screen 101 is divided into four areas including an area A1, an area A2, an area A3, and an area A4. Note that the number of areas is not limited to the four.

In the present modification, each area is further divided into four regions (partial regions). Hereinafter, the regions of the divided areas are also referred to as windows. In the example of FIG. 19, each area is further divided into the four windows. Note that it may be configured such that the area is not further divided, and one diagnosis image is displayed in each area.

In the area A1, four windows W1, W2, W3, and W4 are set. In the windows W1, W2, W3, and W4, person pictures (person images) are displayed. Here, each picture (image) may be either a still image or a moving image. However, the moving image is more favorable because a subject can easily gaze at the moving image. In the area A2, four windows W5, W6, W7, and W8 are set. In the windows W5, W6, W7, and W8, animal pictures (animal images) as the character images are displayed. In the area A3, four windows W9, W10, W11, and W12 are set. In the windows W9, W10, W11, and W12, geometric pictures (geometric images) are displayed. In the area A4, four windows W13, W14, W15, and W16 are set. In the windows W13, W14, W15, and W16, vehicle pictures (vehicle images) as the character images are displayed.

Note that the output controller 353 may be configured to change the area in which the diagnosis image is displayed in a plurality of measurement periods (a first period and a second period). In this case, the evaluator 354 may obtain an average value of evaluation values calculated in the respective periods, as a final evaluation value. For example, evaluation values respectively calculated in two patterns where positions of the area A1 and the area A3, and positions of the area A2 and the area A4 are interchanged may be averaged. Accordingly, an influence of liking of gazing at (such as starting to look at an upper right first) can be eliminated.

Figure 20:
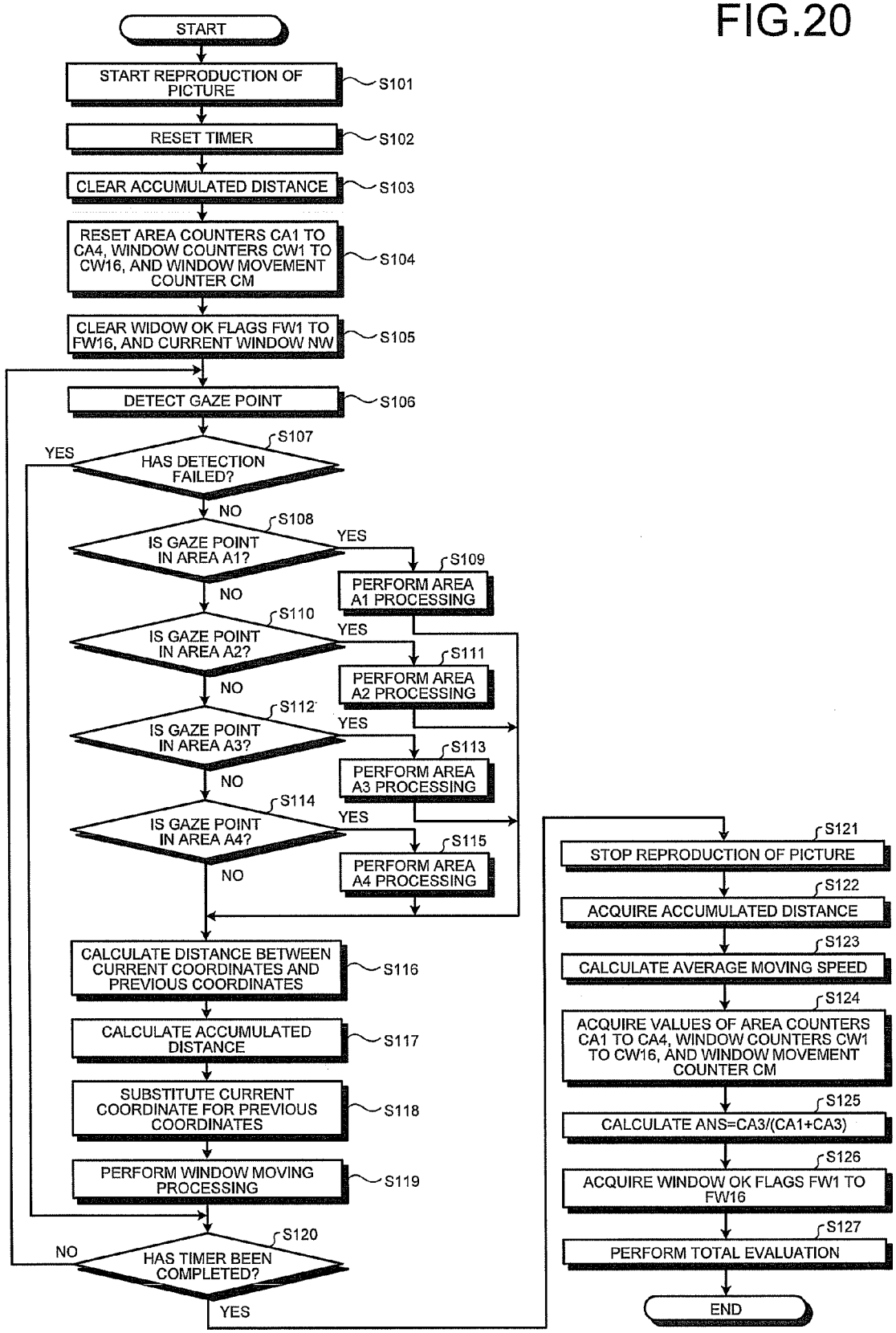
FIG. 20 is a flowchart illustrating an example of diagnosis supporting processing in the first modification.

Next, a diagnosis supporting processing by a diagnosis supporting device 100 according to a first modification configured as described above will be described using FIGS. 20 to 24. FIG. 20 is a flowchart illustrating an example of diagnosis supporting processing in the present modification. Assume that individual calibration has been completed before the processing. The calibration includes camera calibration as described above, and calibration for detecting eye gaze (calibration of eye gaze detection).

First, the output controller 353 starts reproduction of the picture (diagnosis image) (step S101). The output controller 353 resets a timer that determines a picture reproduction time (step S102). The evaluator 354 clears (initializes) an accumulated value (accumulated distance) of the moved distance of the gaze point in a picture reproduction period stored in a storage 150 or the like (step S103).

The evaluator 354 resets (initializes) following counters used in calculation of the evaluation value (step S104).

Area counters CA1 to CA4 that are incremented when a gaze point exists in the areas Window counters CW1 to CW16 that are incremented when a gaze point exists in the windows A window movement counter CM that is incremented when the gaze point is moved from a window to another window.

The evaluator 354 clears (initializes) following information used in calculation of the evaluation value (step S105).

Window OK flags FW1 to FW16 that set 1 when the gaze points exist in the respective windows.

A current window NW that indicates a window where the gaze point has been detected at a present time or a past recent time Next, a gaze point detector 352 detects the gaze point (step S106). The gaze point detector 352 determines whether gaze point detection has failed due to an influence of a blink or the like (step S107). When the blink or the like is caused, pupil detection cannot be performed, and thus the gaze point detection cannot be performed. When the gaze point detection has failed (Yes in step S107), the gaze point detector 352 proceeds to step S120. When the gaze point can be detected (No in step S107), the gaze point detector 352 proceeds to step S108.

In step S108, the gaze point detector 352 determines whether coordinates of the gaze point are within the area A1 (step S108). When the coordinates are within the area A1 (Yes in step S108), the gaze point detector 352 proceeds to step S109. In step S109, the gaze point detector 352 performs processing (area A1 processing) corresponding to the area A1 (step S109). Details of the area A1 processing will be described below. When the coordinates are not within the area A1 (No in step S108), the gaze point detector 352 proceeds to step S110.

In step S110, the gaze point detector 352 determines whether the coordinates of the gaze point are within the area A2 (step S110). When the coordinates are within the area A2 (Yes in step S110), the gaze point detector 352 proceeds to step S111. In step S111, the gaze point detector 352 performs processing (area A2 processing) corresponding to the area A2 (step S111). When the coordinates are not within the area A2 (No in step S110), the gaze point detector 352 proceeds to step S112.

In step S112, the gaze point detector 352 determines whether the coordinates of the gaze point are within the area A3 (step S112). When the coordinates are within the area A3 (Yes in step S112), the gaze point detector 352 proceeds to step S113. In step S113, the gaze point detector 352 performs processing (area A3 processing) corresponding to the area A3 (step S113). When the coordinates are not within the area A3 (No in step S112), the gaze point detector 352 proceeds to step S114.

In step S114, the gaze point detector 352 determines whether the coordinates of the gaze point are within the area A4 (step S114). When the coordinates are within the area A4 (Yes in step S114), the gaze point detector 352 proceeds to step S115. In step S115, the gaze point detector 352 performs processing (area A4 processing) corresponding to the area A4 (step S115). When the coordinates are not within the area A4, for example, when the gaze point exists outside the display screen or the like (No in step S114), the gaze point detector 352 proceeds to step S116.

In step S116, the gaze point detector 352 calculates a distance between the coordinates of a current gaze point and the coordinates of a previous gaze point (step S116). Next, the gaze point detector 352 adds the distance calculated this time to the accumulated distance (step S117). Next, the gaze point detector 352 substitutes the coordinates of the current gaze point for the coordinates of the previous gaze point (step S118). Next, the gaze point detector 352 executes window moving processing (step S119). Details of the window moving processing will be described below.

Next, the output controller 353 determines whether the reproduction of the picture has been terminated (step S120). The output controller 353 determines whether the reproduction of the picture has been terminated according to whether the timer has reached a predetermined value (reproduction time), for example. When the reproduction of the picture has not been terminated (No in step S120), the output controller 353 returns to step S106, and the processing is repeated. When the reproduction of the picture has been terminated (Yes in step S120), the output controller 353 proceeds to step S121.

The output controller 353 stops the reproduction of the picture (step S121). The evaluator 354 acquires the accumulated distance of the gaze point movement (step S122). Further, the evaluator 354 obtains an average speed of the gaze point movement from the accumulated distance and the reproduction time of the picture (step S123). Next, the evaluator 354 acquires values of the area counters CA1 to CA4, acquires values of the window counters CW1 to CW16, and acquired a value of the window movement counter CM (step S124). Next, the evaluator 354 obtains a ratio ANS of the number of gaze points detected in the area (area A3) where the geometric picture is displayed to the total number of gaze points detected in the area (area A1) where the person picture is displayed and in the area (area A3) where the geometric picture is displayed (step S125). The ratio ANS indicates a ratio of looking at the geometric picture, to looking at the person picture and the geometric picture. A possibility of ASD becomes higher as the ratio ANS is higher.

Note that the evaluation value used in the diagnosis support of ASD is not limited to the ratio ANS. For example, a value based on a difference between the number of gaze points detected in the area where the person picture is displayed, and the number of gaze points detected in the area where the geometric picture is displayed, may be used as the evaluation value. Further, in the present modification, the person picture and the geometric picture are compared. However, ratios or the numbers of gaze points of the person picture and the character picture (the animal picture or the vehicle picture) may be compared, or ratios or number of gaze points of the character picture and the geometric picture may be compared. When the person picture and the character picture are compared, the possibility of ASD becomes higher as the ratio of gazing at the character picture is higher. When the character picture and the geometric picture are compared, the possibility of ASD becomes higher as the ratio of gazing at the geometric picture is higher.

Next, the evaluator 354 acquires the window OK flags FW1 to FW16 (step S126). The window OK flag is changed from 0 to 1 when the subject gazes at the corresponding window once. The window OK flags FW1 to FW16 respectively correspond to the windows W1 to W16. The evaluator 354 determines which window the subject looks at, according to the window OK flags.

Finally, the evaluator 354 performs total evaluation (step S127). Details of total evaluation processing will be described below.

Figure 21:
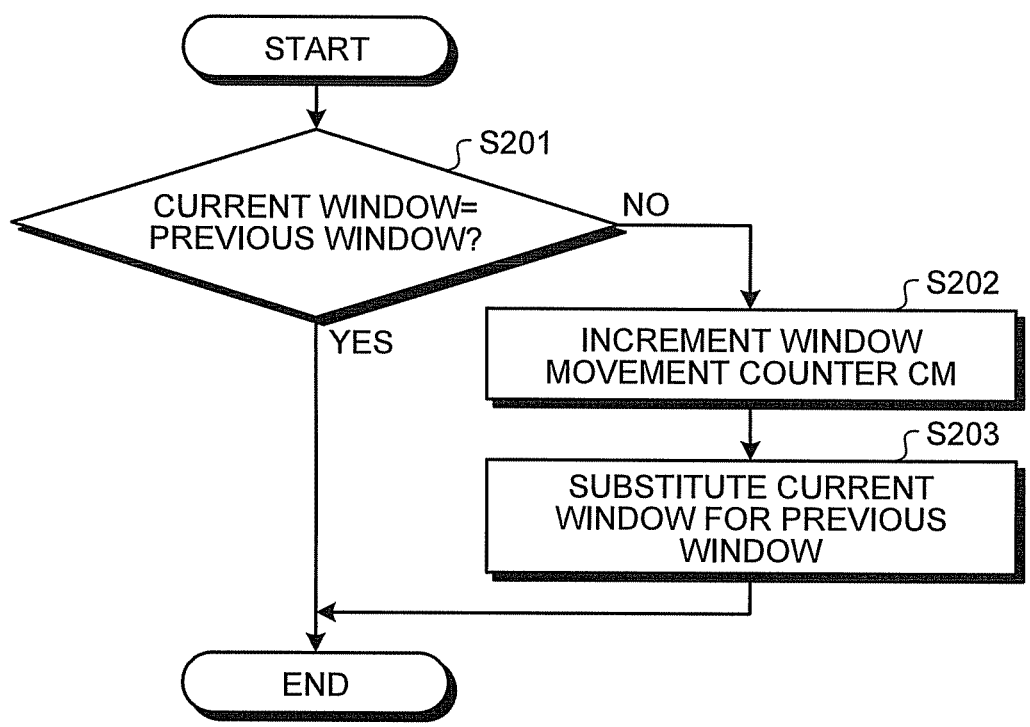
FIG. 21 is a flowchart illustrating an example of window moving processing of FIG. 20.

FIG. 21 is a flowchart illustrating an example of the window moving processing (step S119) of FIG. 20. First, the gaze point detector 352 determines whether the current window is the same as the previous window (step S201).

As described above, the current window is a window where the gaze point has been detected at the current time or the past recent time. When the gaze point has been detected at the current time (No in step S107), and when the gaze point has been detected in any window in the areas, the window where the gaze point has been detected at the current time becomes the current window. Meanwhile, when the gaze point has been detected at the current time (No in step S107), but when the gaze point is not included in any window in the areas, the current window is not updated. That is, the window where the gaze point has been detected at a past time that is not the current time becomes the current window.

The previous window is a window where the gaze point has been detected just before the current window. The current window and the previous window are initialized at the time of the start of the diagnosis supporting processing. When the gaze point has been detected in any window first, the previous window has been initialized, and thus the current window is substituted for the previous window, and the window moving processing may be terminated.

When the current window and the previous window are the same (Yes in step S201), the gaze point detector 352 terminates the window moving processing. When the current window and the previous window are not the same (No in step S201), the gaze point detector 352 increments the window movement counter CM (step S202). Next, the gaze point detector 352 substitutes the current window for the previous window (step S203). In this way, every time the gaze point is moved between the windows, 1 is added to the value of the window movement counter CM.

The window moving processing is processing for confirming movement of the gaze point between the windows. Therefore, when the gaze point has been detected in a place other than the windows, such movement is ignored because the movement is not related to the movement between windows.

Figure 22:
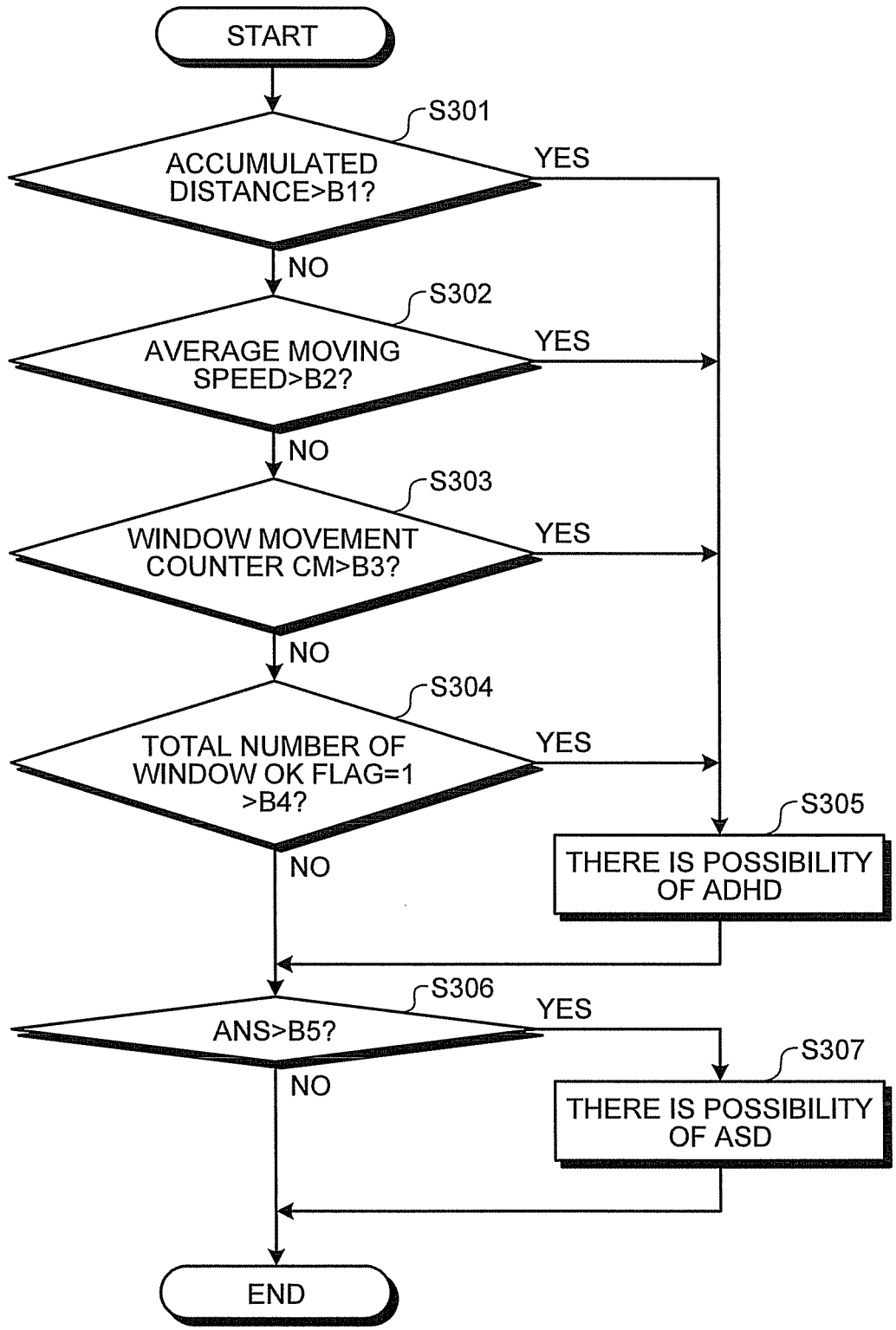
FIG. 22 is a flowchart illustrating an example of total evaluation processing of FIG. 20.

FIG. 22 is a flowchart illustrating an example of the total evaluation processing (step S127) of FIG. 20. First, the evaluator 354 determines whether the accumulated distance of the gaze point is larger than a threshold B1 (step S301). When the accumulated distance is larger than the threshold B1 (Yes in step S301), the evaluator 354 outputs an evaluation result that indicates there is a possibility of ADHD (step S305).

When the accumulated distance is the threshold B1 or less (No in step S301), the evaluator 354 determines whether an average moving speed of the gaze point is larger than a threshold B2 (step S302). When the average moving speed is larger than the threshold 52 (Yes in step S302), the evaluator 354 outputs an evaluation result that indicates there is the possibility of ADHD (step S305).

When the average moving speed is the threshold B2 or less (No in step S302), the evaluator 354 determines whether the value of the window movement counter CM is larger than a threshold 53 (step S303). When the value of the window movement counter CM is larger than the threshold B3 (Yes in step S303), the evaluator 354 outputs an evaluation result that indicates there is the possibility of ADHD (step S305).

When the value of the window movement counter CM is the threshold B3 or less (No in step S303), the evaluator 354 determines whether the number of the window OK flag=1 is larger than a threshold 54 (step S304). When the number of the window OK flag=1 is larger than the threshold B4 (Yes in step S304), the evaluator 354 outputs an evaluation result that indicates there is the possibility of ADHD (step S305).

When the number of the window OK flag=1 is the threshold B4 or less (No in step S304), or after step S305, the evaluator 354 determines whether the ratio ANS that is the evaluation value of ASD is larger than a threshold B5 (step S306). When the ratio ANS is larger than the threshold B5 (Yes in step S306), the evaluator 354 outputs an evaluation result that indicates there is the possibility of ASD (step S307). When the ratio ANS is the threshold B5 or less (No in step S306), or after step S307, the evaluator 354 terminates the total evaluation processing.

Note that the total evaluation processing of FIG. 22 is an example, and is not limited to the example. As described above, the evaluator 354 may just calculate the evaluation value based on at least one of the moved distance (the accumulated distance or the like) of the gaze point, the moving speed (average moving speed or the like) of the gaze point, the number of the gaze points detected in the area (the total number of the window OK flags or the like), and the number of times of movement of the gaze point between the areas (the window movement counter or the like), based on the position of the gaze point.

In the present modification, a different diagnosis image can be displayed in each area of a divided display region, and the evaluation value can be calculated. Therefore, accuracy of diagnosis can be improved.

Figure 23:
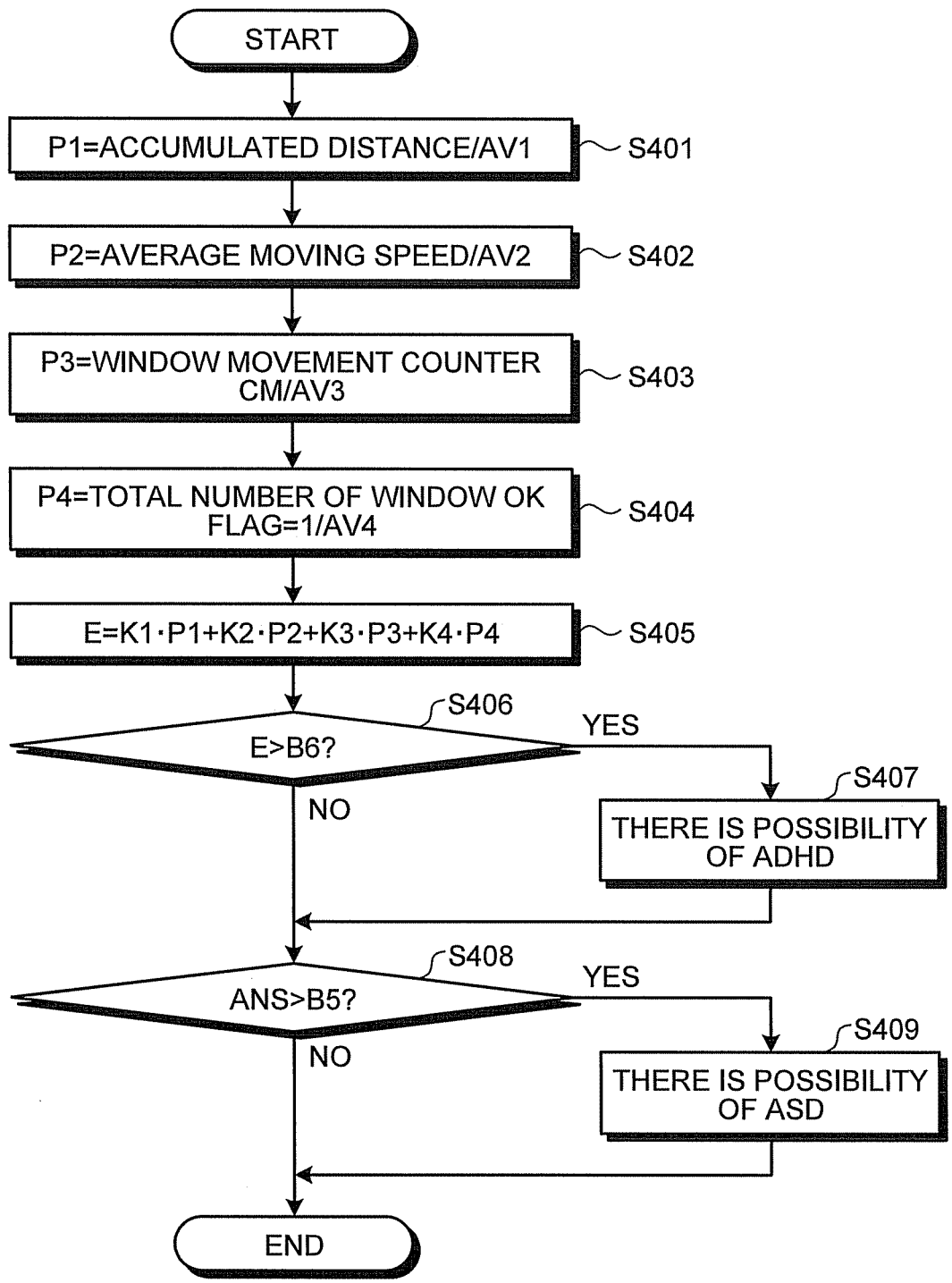
FIG. 23 is a flowchart illustrating another example of the total evaluation processing of FIG. 20.

FIG. 23 is a flowchart illustrating another example of the total evaluation processing (step S127) of FIG. 20. First, the evaluator 354 obtains a ratio P1 of the accumulated distance of the gaze point to an average value AV1 of the accumulated distance (step S401). The evaluator 354 obtains a ratio P2 of the average moving speed of the gaze point to an average value AV2 of the average moving speed (step S402). The evaluator 354 obtains a ratio P3 of the value of the window movement counter CM to an average value AV3 of the value of window movement counter CM (step S403). The evaluator 354 obtains a ratio P4 of the number of the window OK flag=1 to an average value AV4 of the number of the window OK flag=1 (step S404).

As the average values AV1, AV2, AV3, and AV4, average values of the accumulated distances calculated from a large number of subjects, the average moving speeds, the window movement counters CM, and the numbers of the window OK flag=1 are respectively used.

Next, the evaluator 354 obtains an evaluation value E of ADHD that is a total sum of values obtained such that the ratios P1 to 24 are multiplied by weighting coefficients (K1 to K4) respectively (step S405). Next, the evaluator 354 determines whether the evaluation value E of ADHD is larger than a threshold B6 (step S406). When the evaluation value E is larger than the threshold B6 (Yes in step S406), the evaluator 354 outputs an evaluation result that indicates there is the possibility of ADHD (step S407).

When the evaluation value E of ADHD is the threshold B6 or less (No in step S406), or after step S407, the evaluator 354 determines whether the ratio ANS that is the evaluation value of ASD is larger than a threshold B5 (step S408). When the ratio ANS is larger than the threshold B5 (Yes in step S408), the evaluator 354 outputs an evaluation result that indicates there is the possibility of ASD (step S409). When the ratio ANS is the threshold B5 or less (No in step S408), or after step S409, the evaluator 354 terminates the total evaluation processing.

Figure 24:
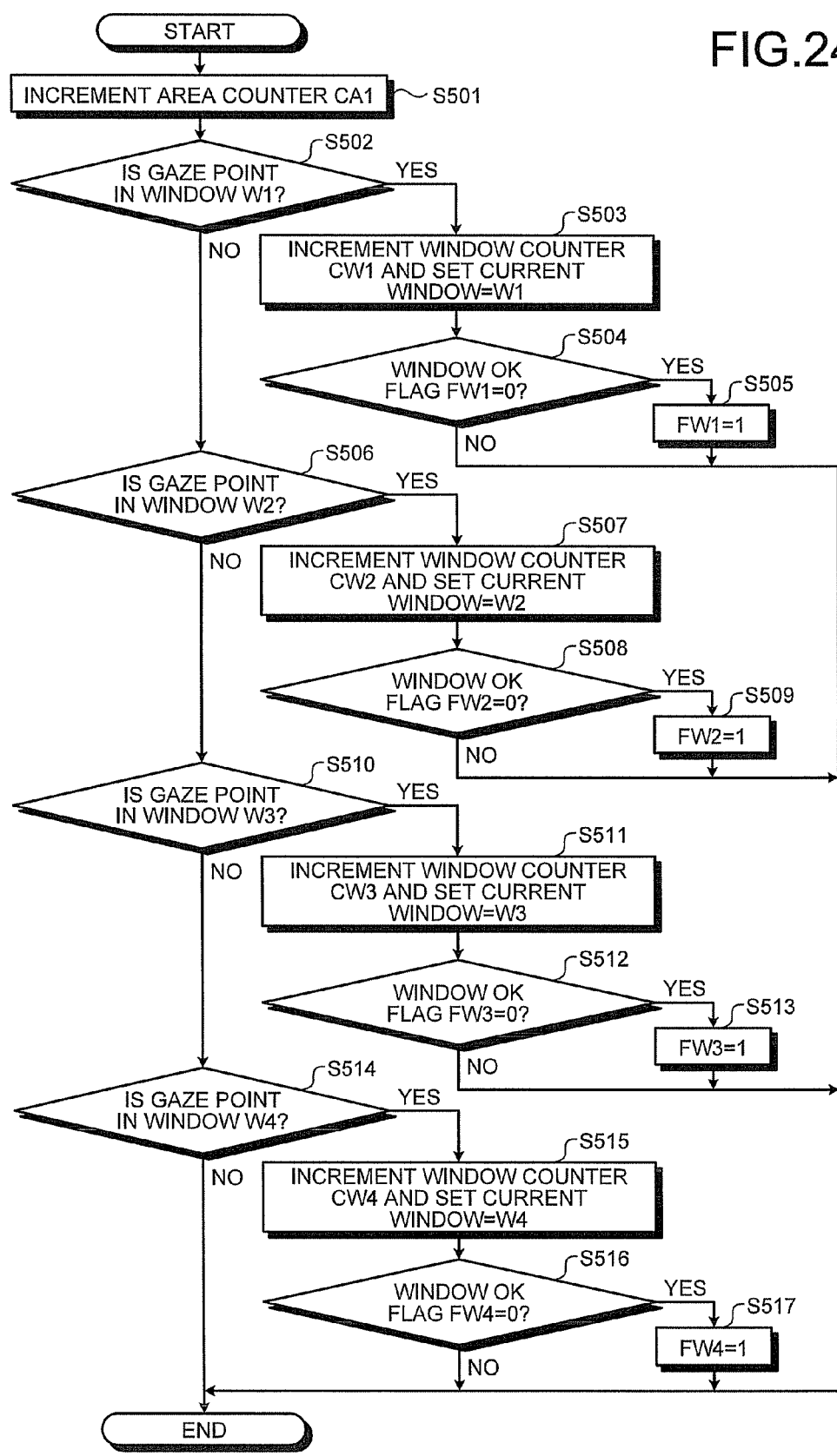
FIG. 24 is a flowchart illustrating an example of area A1 processing of FIG. 20.

FIG. 24 is a flowchart illustrating an example of the area A1 processing (step S109) of FIG. 20. The area A1 processing is performed on the assumption that the current gaze point exists in the area A1 by the determination of step S108.

First, since the gaze point exists in the area A1, the gaze point detector 352 increments an area counter CA1 (step S501).

The gaze point detector 352 determines whether the gaze point exists in the window W1 in the area A1 (step S502). When the gaze point does not exist in the window W1 (No in step S502), the gaze point detector 352 proceeds to step S506. When the gaze point exists in the window W1 (Yes in step S502), the gaze point detector 352 proceeds to step S503. In step S503, the gaze point detector 352 increments the window counter CW1, and sets the window W1 to the current window (step S503).

Next, the gaze point detector 352 determines whether the window OK flag FW1 is 0 (step S504). When the window OK flag FW1=0 (Yes in step S504), the gaze point detector 352 sets the window OK flag FW1=1, and terminates the area A1 processing (step S505). When already the window OK flag FW1=1 (No in step S504), the gaze point detector 352 terminates the area A1 processing.

In step S506, the gaze point detector 352 determines whether the gaze point exists in the window W2 in the area A1 (step S506). When the gaze point does not exist in the window W2 (No in step S506), the gaze point detector 352 proceeds to step S510. When the gaze point exists in the window W2 (Yes in step S506), the gaze point detector 352 proceeds to step S507. In step S507, the gaze point detector 352 increments the window counter CW2, and sets the window W2 to the current window (step S507).

Next, the gaze point detector 352 determines whether a window OK flag FW2 is 0 (step S508). When the window OK flag FW2=0 (Yes in step S508), the gaze point detector 352 sets the window OK flag FW2=1, and terminates the area A1 processing (step S509). When already the window OK flag FW2=1 (No in step S508), the gaze point detector 352 terminates the area A1 processing.

In step S510, the gaze point detector 352 determines whether the gaze point exists in the window W3 in the area A1 (step S510). When the gaze point does not exist in the window W3 (No in step S510), the gaze point detector 352 proceeds to step S514. When the gaze point exists in the window W3 (Yes in step S510), the gaze point detector proceeds to step S511. In step S511, the gaze point detector 352 increments the window counter CW3, and sets the window W3 to the current window (step S511).

Next, the gaze point detector 352 determines whether a window OK flag FW3 is 0 (step S512). When the window OK flag FW3=0 (Yes in step S512), the gaze point detector 352 sets the window OK flag FW3=1, and terminates the area A1 processing (step S513). When already the window OK flag FW3=1 (No in step S512), the gaze point detector 352 terminates the area A1 processing.

In step S514, the gaze point detector 352 determines whether the gaze point exists in the window W4 in the area A1 (step S514). When the gaze point does not exist in the window W4 (No in step S514), the gaze point detector 352 terminates the area A1 processing. When the gaze point exists in the window W4 (Yes in step S514), the gaze point detector 352 proceeds to step S515. In step S515, the gaze point detector 352 increments the window counter CW4, and sets the window W4 to the current window (step S515).

Next, the gaze point detector 352 determines whether a window OK flag FW4 is 0 (step S516). When the window OK flag FW4=0 (Yes in step S516), the gaze point detector 352 sets the window OK flag FW4=1, and terminates the area A1 processing (step S517). When already the window OK flag FW4=1 (No in step S516), the gaze point detector 352 terminates the area A1 processing.

The area A2 processing (step S111), the area A3 processing (step S113), and the area A4 processing (step S115) are similar to the area A1 processing of FIG. 24.

The flowchart of FIG. 24 is an example, and any method can be applied as long as the method can determine whether the gaze point exists in the area (the area counters CA1 to CA4 or the like), whether the gaze point exists in the window (the window counters CW1 to CW16, or the like), or the like. Further, in the case of the configuration in which the area is not divided into the windows, and one diagnosis image is displayed in each area, the processing for windows is replaced with the processing for areas, so that a similar function to the above description can be realized.

As described above, according to the first modification, effects as follows can be obtained, for example:
(1) The device is highly accurate compared with a conventional device that has a problem in accuracy.
(2) A pair of special glasses is not necessary, and even infants can use the device.
(3) Diagnosis support of ASD can be simultaneously performed in addition to ADHD.

(Second Modification)

In diagnosis support of developmental disorder of an infant, a plurality of tests is performed in order to increase detection accuracy of information related to the developmental disorder, and comprehensive determination is made. As the diagnosis tests, tests using characteristics that developmentally disabled children do not look at eyes of a person, and developmentally disabled children prefer a geometric pattern picture than a person picture can be considered.

For example, developmental disabled infants have characteristics that the babies do not look at an object pointed at by a parent, do not look at an object that a parent turns his/her face to and gazes at, do not request a thing that the babies want by pointing a finger at, and the like. Therefore, a diagnosis supporting device of the present modification displays a picture in which a person, and the person points at any of a plurality of gaze objects. Further, the diagnosis supporting device of the present modification measures a dwell time of a gaze point to each region such as a region including an object pointed at by a person with a finger or the like, or a region including an object other than the object, and calculates an evaluation value of developmental disorder. Accordingly, the diagnosis supporting device realizes highly accurate evaluation support of a developmental disorder risk.

In the present modification, a diagnosis image includes, for example, an image of an object, an image of a person who points at the object, and an image of a pointing object such as a finger used to point at the object. Note that the pointing object is not limited to the finger, and an arbitrary object such as a rod-like object can be used as long as the object can point at another object.

In the present modification, an output controller 353 displays a diagnosis image including the image of an object, and the image of a person who points at the object on a display 210.

Figure 25A:
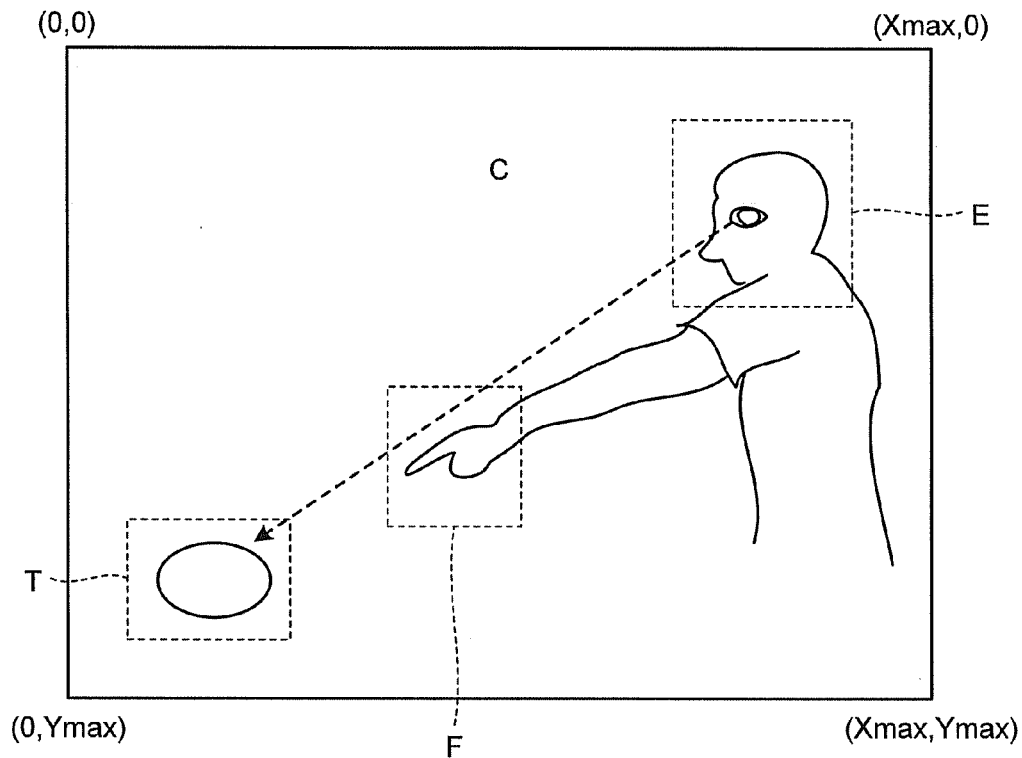
FIG. 25A is an explanatory diagram illustrating an example of a diagnosis image of a second modification.
Figure 25B:
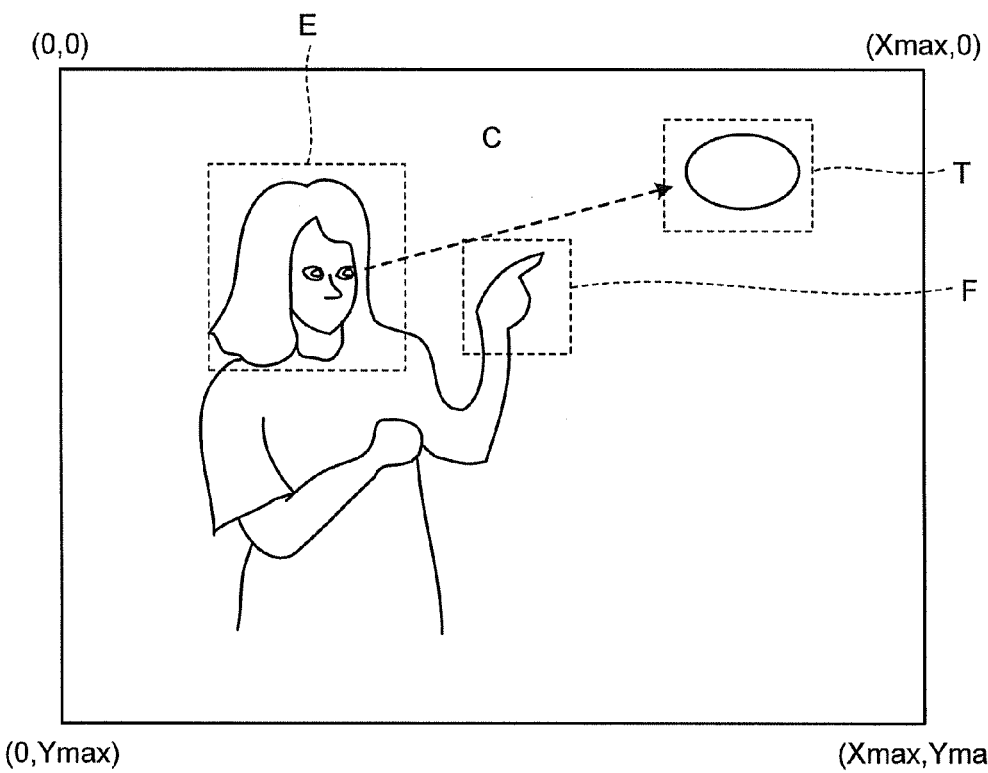
FIG. 25B is an explanatory diagram illustrating an example of a diagnosis image of the second modification.

FIGS. 25A and 25B are explanatory diagrams illustrating examples of the diagnosis image. FIGS. 25A and 25B are examples of images that show a state in which a person points at an object. Note that the images may be either a still image or a moving image (picture). However, the moving image is desirable because a subject can easily gaze at the moving image. As illustrated in FIGS. 25A and 25B, the person points at the object while gazing at the object.

A region including the object is a region T, a region including the pointing object (such as a hand) is a region F, and a region including a face is a region E. A region other than the aforementioned regions on a screen is a region C. On the screen, a position is expressed by coordinates where an upper left position is expressed by (0, 0) and a lower right position is expressed by (Xmax, Ymax). That is, a right direction is plus in X coordinates, and a down direction is plus in Y coordinates.

Figure 26:
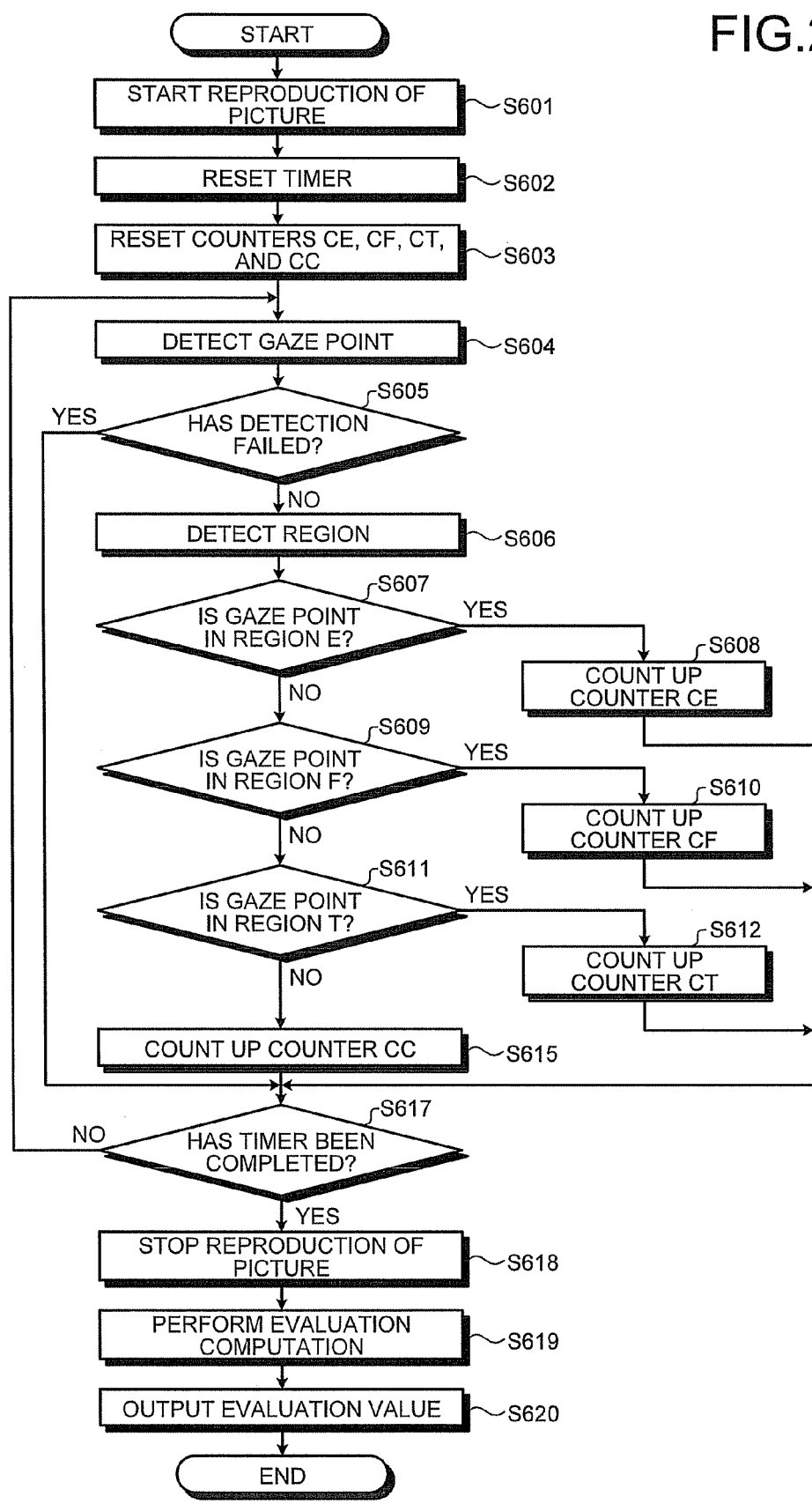
FIG. 26 is a flowchart illustrating an example of diagnosis supporting processing in the second modification.

Diagnosis supporting processing of when a diagnosis image including one object, one pointing object, and one face is used, like FIGS. 25A and 25B will be described. FIG. 26 is a flowchart illustrating an example of the diagnosis supporting processing of this case.

First, the output controller 353 starts reproduction of a picture (step S601). The output controller 353 resets a timer that measures a slightly shorter time than a reproduction time of the picture (step S602). An evaluator 354 resets (initializes) following counters used in calculation of an evaluation value (step S603).

A counter CE that is counted up when a subject gazes at the region E including the face A counter CF that is counted up when a subject gazes at the region F including the pointing object (a hand or the like)

A counter CT that is counted up when a subject gazes at the region T including the object A counter CC that is counted up when a subject gazes at the region C other than the aforementioned regions Gaze point measurement is performed for each one frame of stereo cameras that capture an image in synchronization with each other, for example. That is, a gaze point is measured in each predetermined time interval. Further, a count value of each counter corresponds to a gaze time (the dwell time of the gaze point).

Next, a gaze point detector 352 performs gaze point detection (step S604). The gaze point detector 352 determines whether the gaze point detection has failed (step S605). When an image of a pupil or a corneal reflection cannot be obtained due to a blink or the like, the gaze point detection fails. Further, when the gaze point does not exist on a display screen 101 (when the subject looks at a thing other than the display screen 101), the gaze point detection fails.

When the gaze point detection has failed (Yes in step S605), the gaze point detector 352 moves onto step S617 so as not to influence the counters. When the gaze point detection has succeeded (No in step S605), the gaze point detector 352 detects which region the gaze point of the subject exists, from coordinates of the gaze point (step S606). Next, the gaze point detector 352 determines whether the gaze point exists in the region E (step S607). When the gaze point exists in the region E (Yes in step S607), the gaze point detector 352 counts up the counter CE (step S608). When the gaze point does not exist in the region E (No in step S607), the gaze point detector 352 determines whether the gaze point exists in the region F (step S609). When the gaze point exists in the region F (Yes in step S609), the gaze point detector 352 counts up the counter CF (step S610). When the gaze point does not exist in the region F (No in step S609), the gaze point detector 352 determines whether the gaze point exists in the region T (step S611). When the gaze point exists in the region T (Yes in step S611), the gaze point detector 352 counts up the counter CT (step S612). When the gaze point does not exist in the region T (No in step S611), that is, when the gaze point does not exist in any of the regions E, F, and T, the gaze point detector 352 counts up the counter CC (step S615).

Accordingly, a counted value of the counter of the region that the subject gazes at is increased, and the dwell time of the gaze can be measured.

Next, the output controller 353 determines whether the timer has been completed (step S617). When the timer has not been completed (No in step S617), the output controller 353 returns to step S604, and the processing is repeated. When the timer has been completed (Yes in step S617), the output controller 353 stops the reproduction of the picture (step S618).

Next, the evaluator 354 performs evaluation computation related to diagnosis support of a developmental disorder risk, based on the dwell times of the gaze points of the respective regions (step S619). Next, the evaluator 354 outputs an evaluation value, and terminates the processing (step S620).

Many methods are applicable to the evaluation computation of step S619. A simplest method is a method of calculating the dwell time itself (the counted value of the counter CT) of the gaze point in the region T including the object, as the evaluation value. A neurotypical subject has a strong tendency to gaze at an object in a direction pointed at. Therefore, a possibility of developmental disorder becomes higher as a value of the dwell time is lower.

Further, the neurotypical subject has a tendency to loot at a face of a person, and has a tendency to look at the front of an eye gaze when pointed at. Therefore, the accuracy is further improved by considering the dwell time of the gaze point in the region (region E) including the face. For example, an evaluation value ANS calculated by a following formula (1) may be used.

$$ANS = (Kt \times CT) + (Ke \times CE) \qquad (1)$$

where Kt and Ke are weighting coefficients, and Kt>Ke.

Further, the neurotypical subject has a strong tendency to look at the pointing object (such as a hand that points a finger at an object). Therefore, the accuracy is further improved by considering the dwell time of the gaze point in the region F. For example, an evaluation value ANS calculated by a following formula (2) may be used.

$$ANS = (Kt \times CT) + (Kf \times CF) \qquad (2)$$

where Kf is a weighting coefficient.

Further, an evaluation value ANS calculated by a following formula (3), putting the formulae (1) and (2) together, may be used.

$$ANS=(Kt \times CT)+(Ke \times CE)+(Kf \times CF) \quad (3)$$

A subject having a high risk of developmental disorder has a high probability of gazing at the region C outside predetermined regions. Therefore, the accuracy is further improved by considering the dwell time of the gaze point in the region C. For example, an evaluation value ANS calculated by a following formula (4) may be used.

$$ANS=(Kt \times CT)+(Ke \times CE)+(Kf \times CF)-(Kc \times CC) \quad (4)$$

where Kc is a weighting coefficient.

The diagnosis images of FIGS. 25A and 25B are examples, and a diagnosis image used for diagnosis is not limited to the examples. For example, a diagnosis image including a plurality of objects may be used.

Figure 27A:
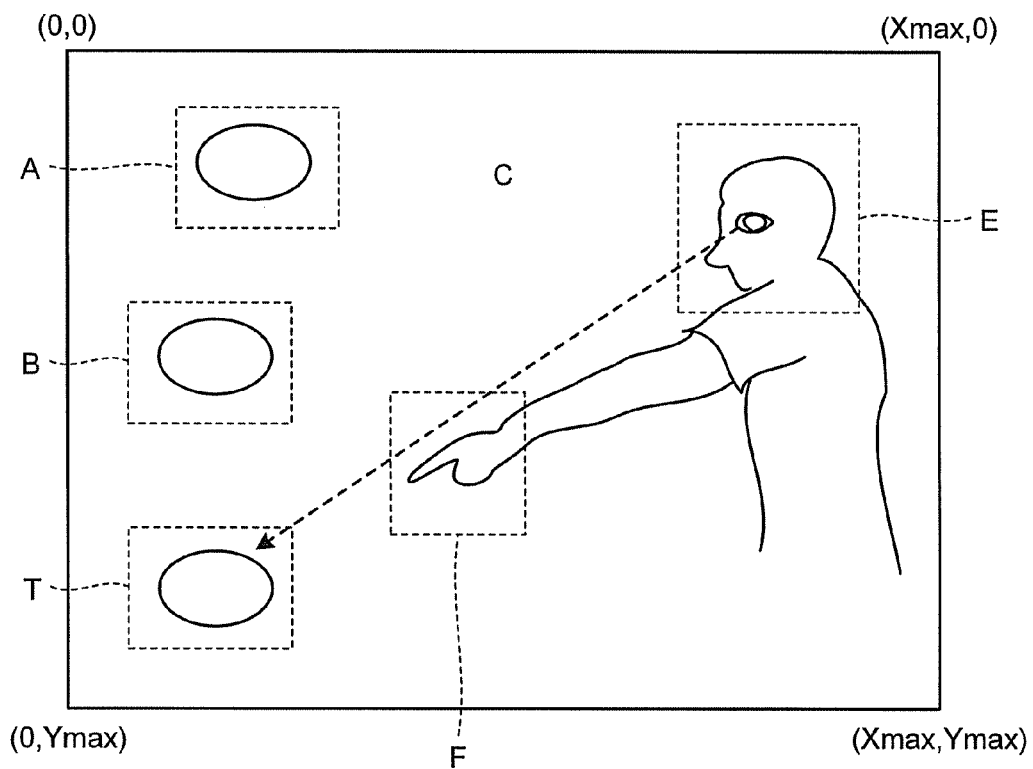
FIG. 27A is an explanatory diagram illustrating another example of a diagnosis image.
Figure 27B:
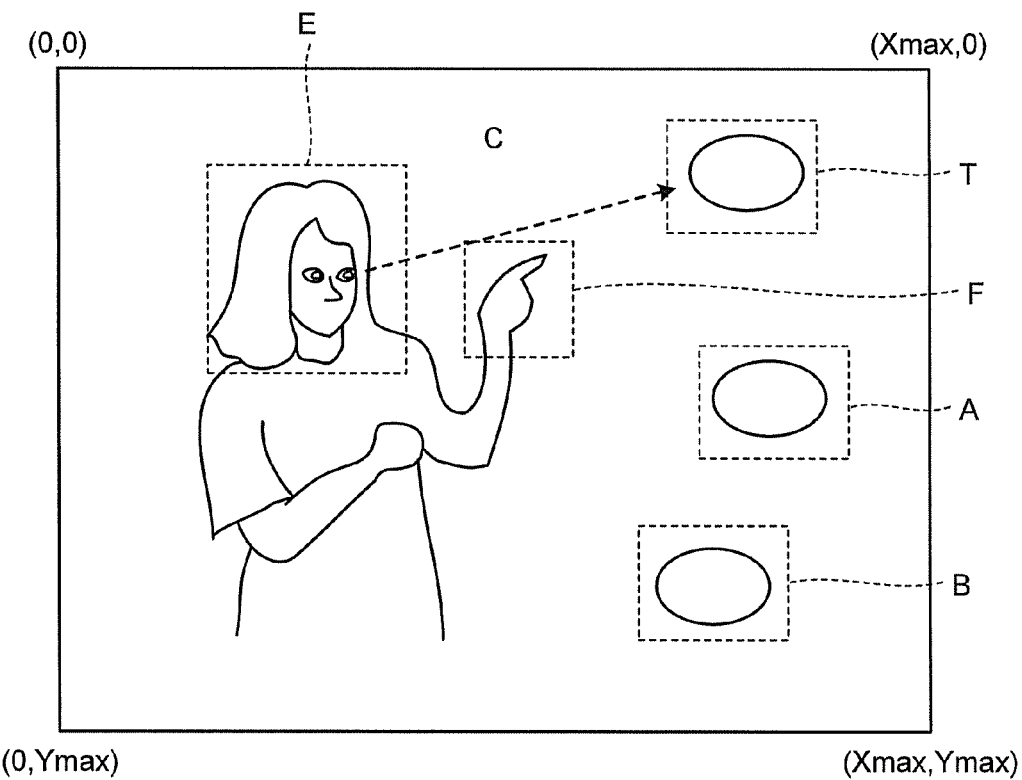
FIG. 27B is an explanatory diagram illustrating another example of a diagnosis image.

FIGS. 27A and 27B are explanatory diagrams illustrating other examples of diagnosis images. FIGS. 27A and 27B are examples of diagnosis images that further include other objects similar to an object pointed at. In FIGS. 27A and 27B, two regions including other objects are a region A and a region B. A subject with developmental disorder has a high probability of gazing at the region A or the region B than the region T. Therefore, detection accuracy is improved by use of a diagnosis image like FIG. 27A or 27B.

Figure 28:
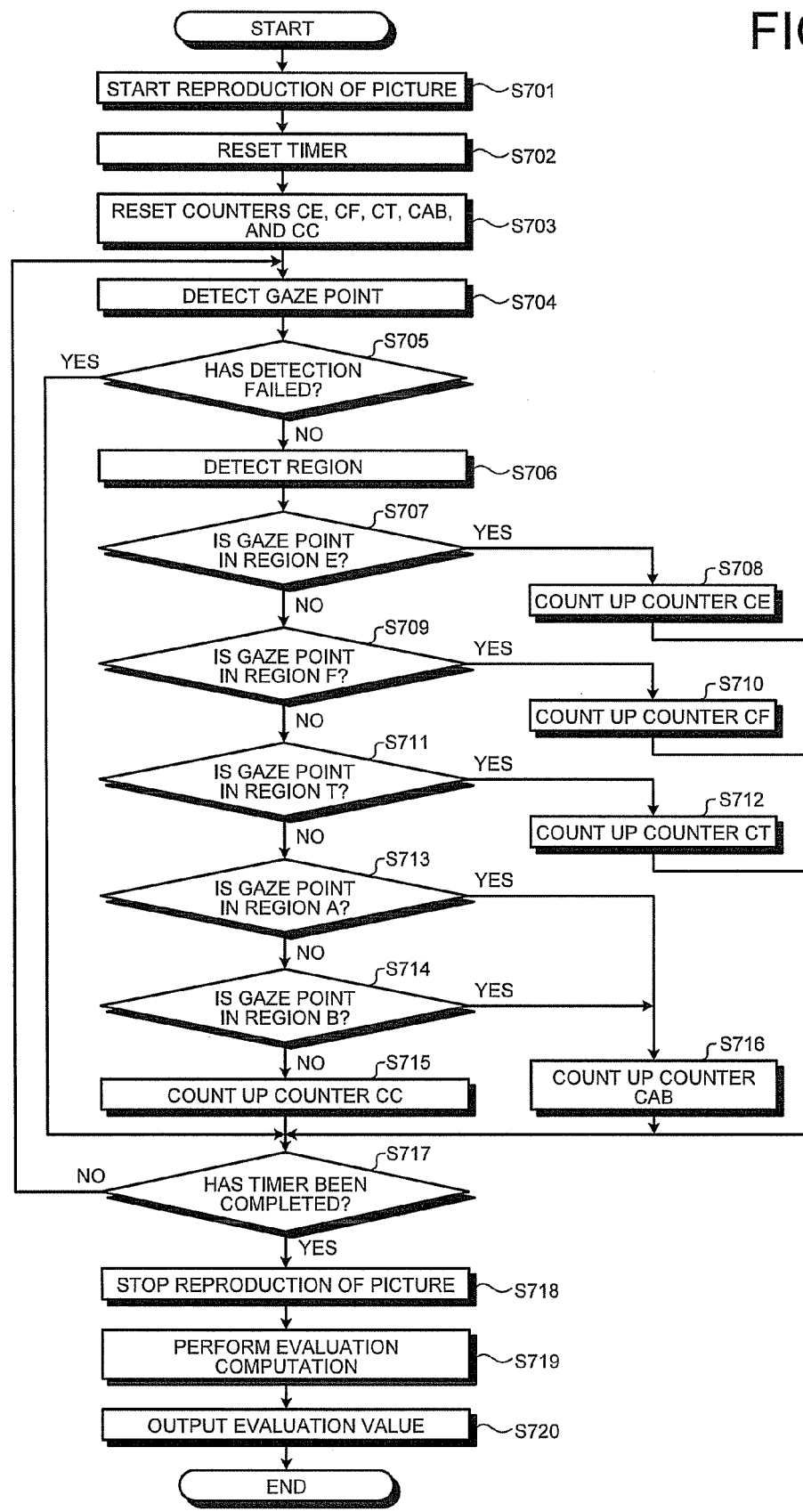
FIG. 28 is a flowchart illustrating another example of the diagnosis supporting processing.

Diagnosis supporting processing of when a diagnosis image including a plurality of objects, a pointing object, and a face, like FIGS. 27A and 27B, will be described. FIG. 28 is a flowchart illustrating an example of the diagnosis supporting processing of this case.

FIG. 28 is different from FIG. 26 in that steps S713, S714, and S716 are added. Further, FIG. 28 is different in that a counter CAB is further reset (initialized) in step S703. Further, evaluation computation of step S719 is different from step S619. Other steps have similar processing to FIG. 26, and thus description is omitted.

Steps S713, S714, and S716 are processing related to the region A and the region B.

The gaze point detector 352 determines whether the gaze point exists in the region A (step S713) when the gaze point does not exist in the region T (No in step S711). When the gaze point exists in the region A (Yes in step S713), the gaze point detector 352 counts up the counter CAB (step S716). When the gaze point does not exist in the region A (No in step S713), the gaze point detector 352 determines whether the gaze point exists in the region B (step S714). When the gaze point exists in the region B (Yes in step S714), the gaze point detector 352 counts up the counter CAB (step S716). When the gaze point does not exist in the region B (No in step S714), the gaze point detector 352 counts up the counter CC (step S715).

As described above, in the example of FIG. 28, the counter CAB is used. The counter CAB is a counter counted up when a subject gazes at the region A or the region B. Evaluation computation of step S719 is different from S619 in that the counter CAB is used as follows. That is, the evaluator 354 may use an evaluation value ANS calculated by a following formula (5).

$$ANS=(Kt \times CT)+(Ke \times CE)-(Kab \times CAB) \quad (5)$$

Further, the neurotypical subject has a strong tendency to look at the pointing object (a hand that points a finger at an object, or the like). Therefore, the accuracy is further improved by considering the dwell time of the gaze point in the region F. For example, an evaluation value ANS calculated by a following formula (6) may be used.

$$ANS=(Kt \times CT)+(Kf \times CF)-(Kab \times CAB) \quad (6)$$

Further, an evaluation value ANS calculated by a following formula (7), putting the formulae (5) and (6) together, may be used.

$$ANS=(Kt \times CT)+(Ke \times CE)+(Kf \times CF)-(Kab \times CAB) \quad (7)$$

The subject having a high risk of developmental disorder has a high probability of gazing at the region C outside predetermined regions. Therefore, the accuracy is further improved by considering the dwell time of the gaze point in the region C. For example, an evaluation value ANS calculated by a following formula (8) may be used.

$$ANS=(Kt \times CT)+(Ke \times CE)+(Kf \times CF)-(Kc \times CC)-(Kab \times CAB) \quad (8)$$

Figure 29:
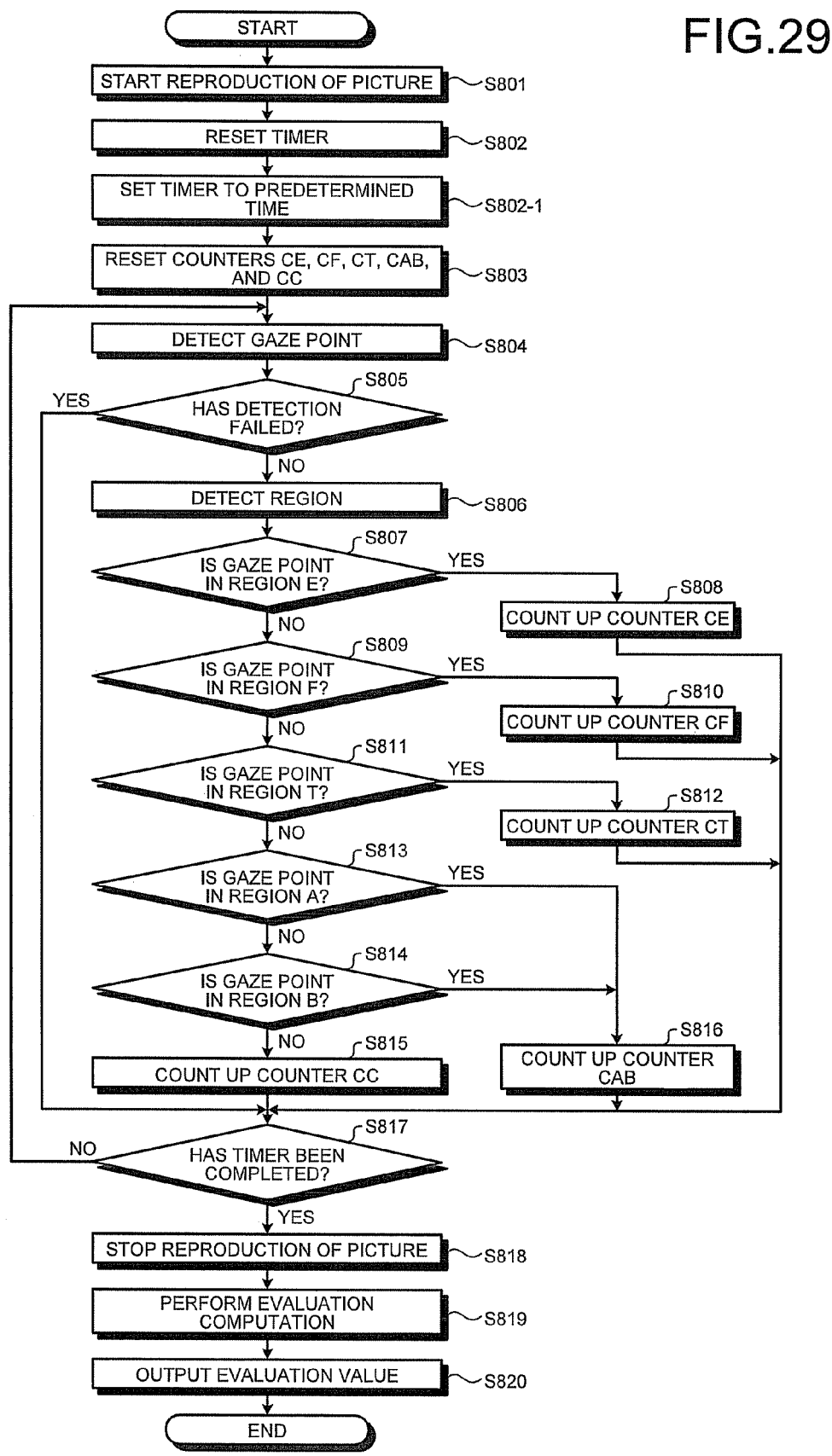
FIG. 29 is a flowchart illustrating another example of the diagnosis supporting processing.

Another example of the diagnosis supporting processing of when a diagnosis image including a plurality of objects is used will be described. FIG. 29 is a flowchart illustrating another example of the diagnosis supporting processing of this case. This example uses a diagnosis image, in which a picture is started in a state where a person does not point at an object, and after the elapse of a predetermined time from the start, the person points at an object T while gazing at the object T. That is, diagnosis supporting processing that makes use of a tendency that a subject looks at a direction pointed at by a hand or a finger, after being prompted to pay attention to movement of the hand or the finger is realized. With such a configuration, the accuracy of diagnosis is further improved.

FIG. 29 is different from FIG. 28 in that step S802-1 is added. In step S802-1, the gaze point detector 352 performs processing of waiting for elapse of a predetermined time using a timer (step S802-1). The predetermined time is a time to complete an operation to point at an object by a person. Accordingly, the gaze point of the subject after completion of the operation to point at an object can be measured. Note that the gaze point detector 352 performs the processing of waiting for elapse of a predetermined time using a timer in FIG. 29. Instead, the evaluator may calculate an evaluation value, based on a value output from the gaze point detector after the elapse of a predetermined time.

Figure 30:
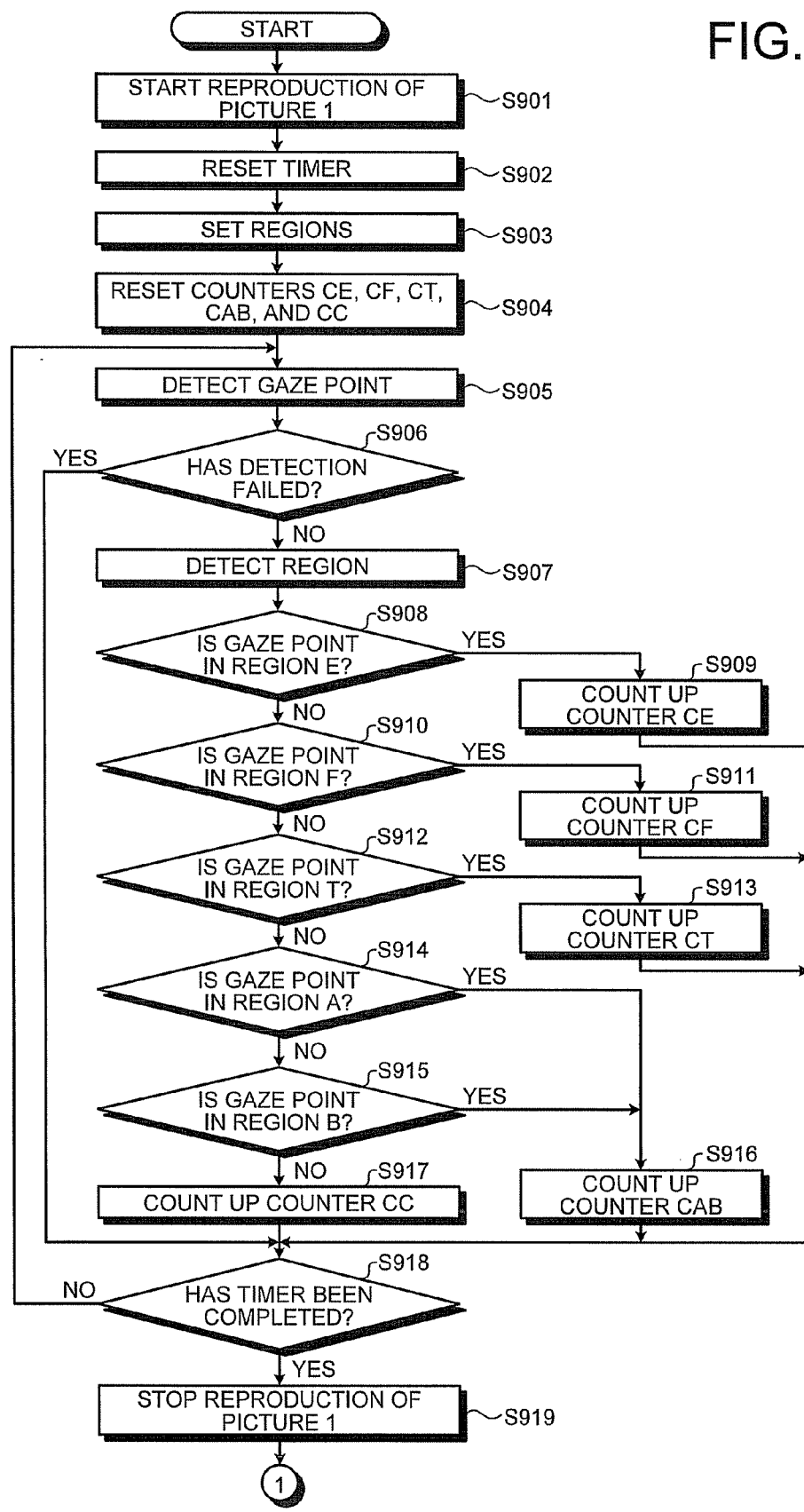
FIG. 30 is a flowchart illustrating an example of diagnosis supporting processing of when a plurality of diagnosis images is used.
Figure 31:
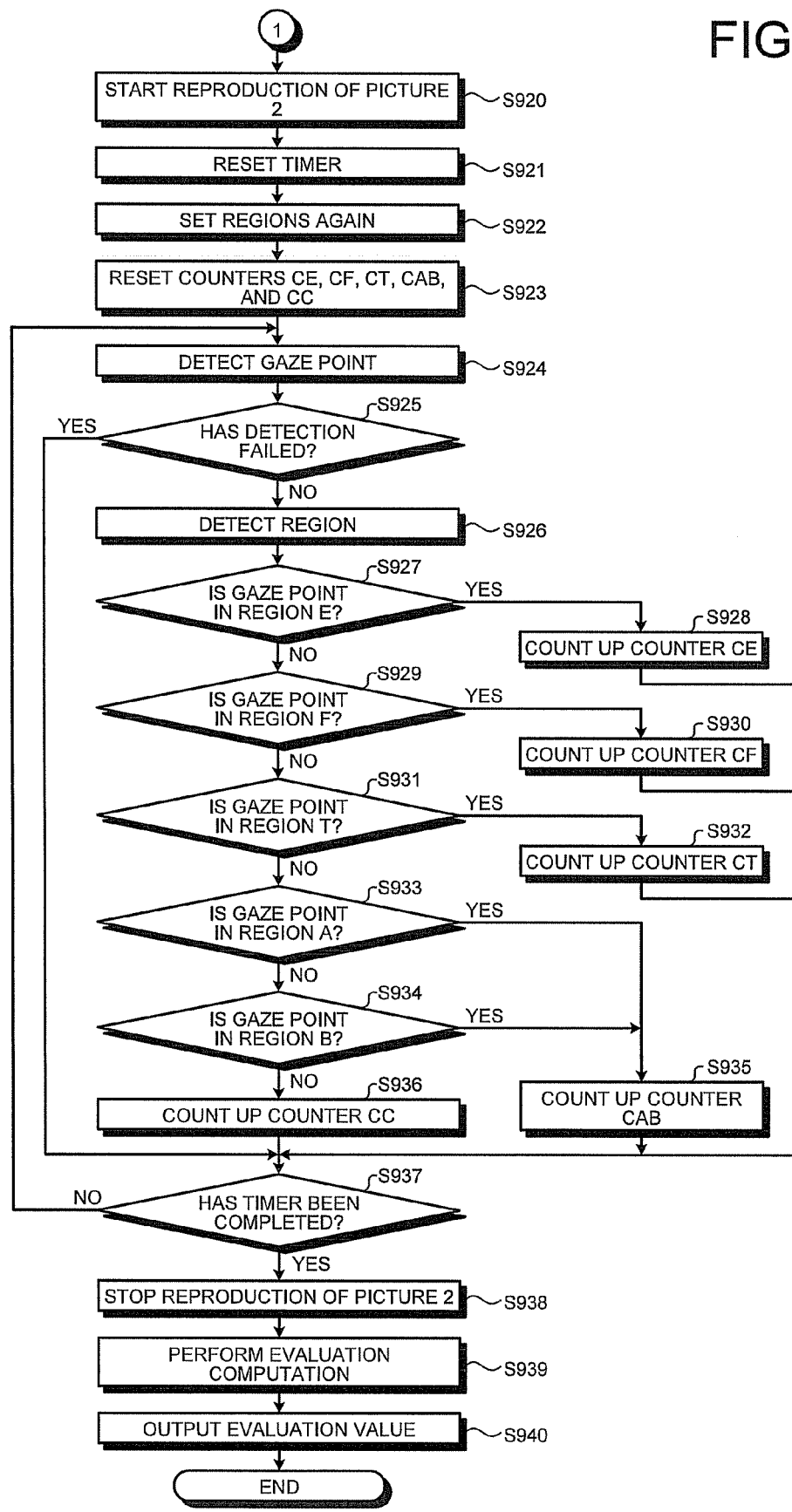
FIG. 31 is a flowchart illustrating an example of diagnosis supporting processing of when a plurality of diagnosis images is used.

Examples using one diagnosis image have been described so far. However, a plurality of diagnosis images may be used. FIGS. 30 and 31 are flowcharts illustrating an example of diagnosis supporting processing of when a plurality of diagnosis images is used. FIGS. 30 and 31 are an example of a case where two pictures like FIGS. 27A and 27B are continuously displayed, and evaluation is comprehensively performed. The two pictures are connected, for example. Note that a similar process can be applied to a case where three or more pictures are continuously displayed.

A different point of FIG. 30 from FIG. 28 is that step S903 is added. In step S903, the gaze point detector 352 sets regions (regions E, F, T, A, and B) to the first picture (picture 1). Since two different pictures are displayed, setting of regions corresponding to respective pictures is performed in this step. Further, a different point of FIG. 31 from FIG. 28 is that step S922 is added. In step S922, the gaze point detector 352 sets regions (regions E, F, T, A, and B) to the second picture (picture 2). For example, the gaze point detector 352 refers to a coordinate value determined for each picture and stored in a storage 150 or the like, and sets regions of each picture.

In the example of FIGS. 30 and 31, a dwell time of a gaze point in each region is continuously measured for the two pictures having mutually different positions of an object and a person. With this method, influences of liking and tendency of when a subject observes a picture can be eliminated. For example, as illustrated in FIGS. 27A and 27B, if two diagnosis images in which positions of an object and a person are symmetric are used, even for a subject who is more likely to look at a left side or a subject who is more likely to look at a right side, an influence of the tendency of the subject can be eliminated, and more accurate diagnosis can be realized. Further, the image of an object is favorably an image that is not a geometric pattern image, which is more likely to be looked at by a developmentally disabled child by preference. For example, an image of a character, a nature image (an animal, a plant, a landscape of nature, or the like), a vehicle, or the like, which can be distinguished from the image of a person are favorable.

In the above-described example, diagnosis images that include an image of a person who points at an object, and an image of a pointing object such as a finger used to point at the object are used. However, diagnosis images are not limited to the above example. As described above, infants with developmental disorder have a characteristic that the babies do not look at an object that a parent turns his/her face to and gazes at. In the present modification, diagnosis images in which a person turns his/her face to an object and gazes at the object are used, in consideration of the characteristic.

Figure 32A:
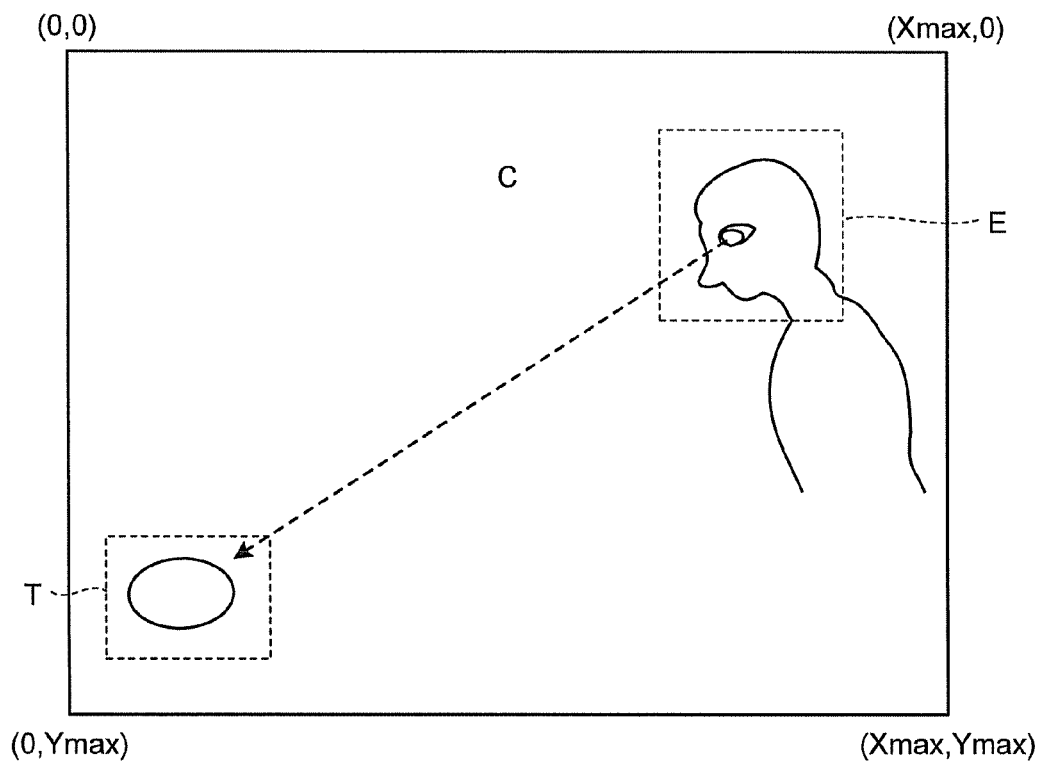
FIG. 32A is an explanatory diagram illustrating another example of a diagnosis image.
Figure 32B:
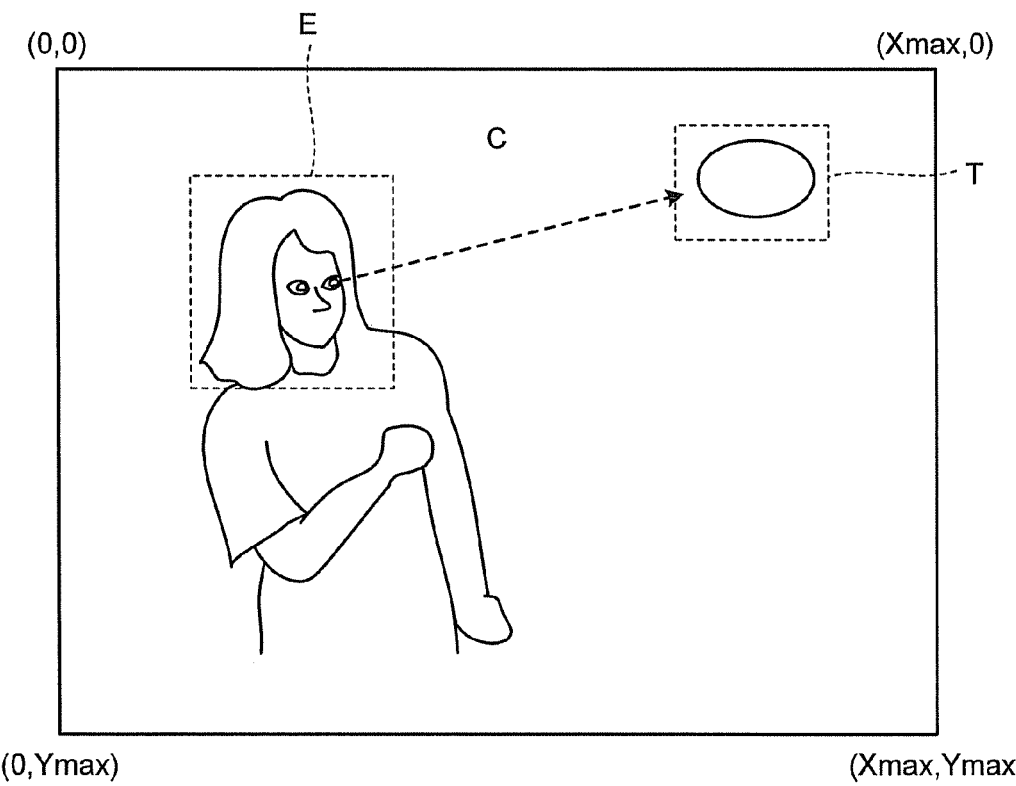
FIG. 32B is an explanatory diagram illustrating another example of a diagnosis image.

FIGS. 32A to 32D are explanatory diagrams illustrating other examples of diagnosis images. FIGS. 32A and 32B are examples of images illustrating a state in which a person turns his/her face in a direction of a gaze object, and gazes at the gaze object. The persons in the diagnosis images turn their faces in the direction of an object while gazing at the object.

In FIGS. 32A and 32B, a region including an object is a region T, and a region including a face is a region E. A region other than the aforementioned regions on a screen is a region C. On the screen, a position is expressed by coordinates, where an upper left position is (0, 0), and a lower right position is (Xmax, Ymax). That is, a right direction is plus in X coordinates, and a down direction is plus in Y coordinates.

Diagnosis supporting processing of when diagnosis images like FIGS. 32A and 32B are used can be realized by a flowchart similar to FIG. 26, for example. Since the diagnosis images of the present modification do not include the region F that includes a pointing object, following processing related to the region F in the flowchart of FIG. 26 can be omitted.

Initialization of the counter CF in step S603
step S609
step S610

Following various evaluation computation methods are applicable in the present modification.

A method of calculating the dwell time itself (the counted value of the counter CT) of the gaze point in the region T including an object, as the evaluation value A method using the evaluation value ANS calculated by the formula (1)

A method using an evaluation value ANS calculated by a following formula (9) similar to the formula (4)

$$ANS=(Kt \times CT)+(Ke \times CE)-(Kc \times CC) \quad (9)$$

Figure 32C:
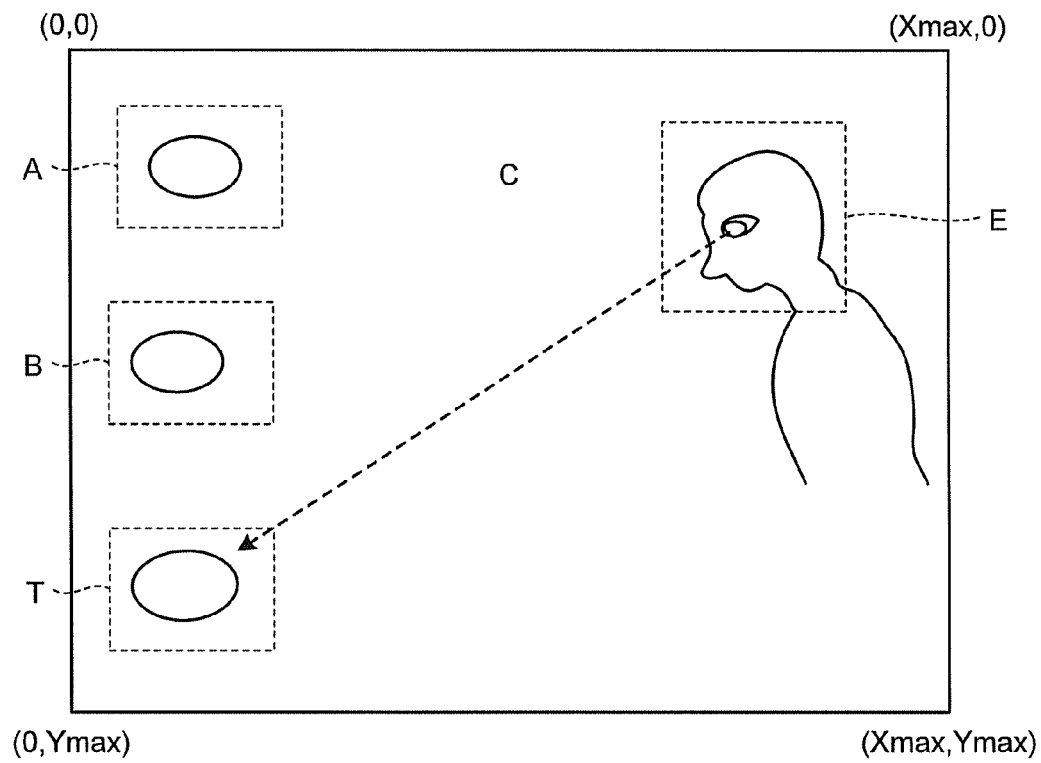
FIG. 32C is an explanatory diagram illustrating another example of a diagnosis image.
Figure 32D:
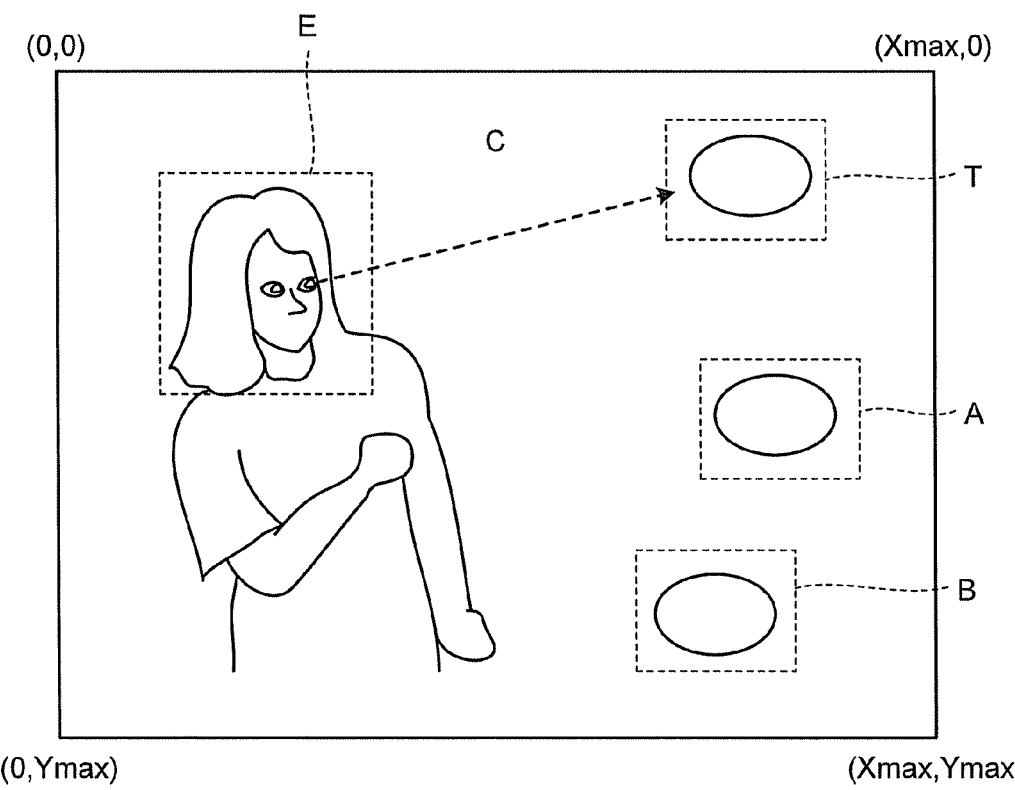
FIG. 32D is an explanatory diagram illustrating another example of a diagnosis image.

FIGS. 32C and 32D are explanatory diagrams illustrating other examples of diagnosis images. FIGS. 32C and 32D are examples of diagnosis images that further include other objects similar to the object. In FIGS. 32C and 32D, two regions that include other objects are a region A and a region B, respectively. The subject with developmental disorder has a high probability of gazing at the region A or the region B than the region T. Therefore, by use of diagnosis images like FIGS. 32C and 32D, the accuracy of detection is improved.

Diagnosis supporting processing of when diagnosis images like FIGS. 32C and 32D are used can be realized by a flowchart similar to FIG. 28, for example. Since the diagnosis images in the present modification do not include the region F that includes a pointing object, following processing related to the region F in the flowchart of FIG. 28 can be omitted.

Initialization of the counter CF in step S703
step S709
step S710

A following evaluation computation method may be applied when FIGS. 32C and 32D are used.

A method using the evaluation value ANS calculated by the formula (5)

A method using an evaluation value ANS calculated by a following formula (10) similar to the formula (8)

$$ANS=(Kt \times CT)+(Ke \times CE)-(Kc \times CC)-(Kab \times CAB) \quad (10)$$

Similarly to FIG. 29, a diagnosis image in which a person gazes at an object after elapse of a predetermined time may be used. That is, a diagnosis image in which a picture is started in a state where a person does not turn his/her face to an object and does not gaze at the object, and after elapse of a predetermined time from the start, the person turns his/her face to an object T, and gazes at the object T may be used. In the first modification, the direction of the face of the person has been described. However, a direction of an eye may be employed instead of the direction of the face. That is, diagnosis supporting processing that makes use of tendency that a subject looks at a direction indicated by a face or an eye, after being prompted to pay attention to movement of the face or the eye of a person is realized. With such a configuration, the accuracy of diagnosis is further improved. Further, the diagnosis may be realized by both of the direction of the face and the direction of the eye of the person, or may be realized by all of a direction of the pointing object such as a finger used to point at an object, the direction of the face, and the direction of the eye.

Similarly to FIG. 30, a method of continuously displaying a plurality of pictures, and comprehensively performing evaluation may be applied. For example, two pictures like FIGS. 32A and 32B, or FIGS. 32C and 32D may be continuously displayed, and comprehensively evaluated. The two pictures are connected, and both are configured in a predetermined time.

As described above, according to the second modification, following effects can be obtained, for example.

(1) A reaction of an infant to pointing a finger can be measured.

(2) A reaction after a plurality of objects is displayed and is pointed at can be measured, and thus accuracy is improved.

(3) Since a characteristic of gazing at a fingertip or a face of a person can be taken into account, accuracy is improved.

(4) Since pointing a finger is not included, a movement of an eye gaze influenced by movement can be suppressed, and specificity of measurement is increased.

(Third Modification)

A method of displaying a person picture and a geometric pattern in parallel, and checking which ratio of the picture or the pattern a subject gazes at is higher, like a conventional method, has a problem of difficulty in an increase in detection sensitivity, depending on a characteristic of the picture. This is because, when a geometric pattern with loud color and dramatic movement is used, for example, even a neurotypical subject looks at the geometric pattern, while when a geometric pattern with quiet color and quiet movement is used, even a subject with developmental disorder may not gaze at the geometric pattern. As described above, for highly accurate diagnosis support, it is desirable to produce a well-balanced picture. However, there is individual difference, and such production has been difficult.

Therefore, a diagnosis supporting device of a third modification includes a picture region in which a person picture is displayed and a picture region in which a geometric pattern picture is displayed, and the person picture and the geometric pattern picture are displayed respectively within a display time, while at least one of contrast, color density, the degree of transmittance, and the like is changed. Accordingly, deviation of developmental disorder detection sensitivity due to individual difference of the picture is decreased, and highly accurate detection is realized.

In the present modification, a diagnosis image includes, for example, a person image (person picture) and a geometric pattern image (geometric pattern picture).

In the present modification, an output controller 353 displays the diagnosis image including a person image and a geometric pattern image on a display 210. Further, the output controller 353 displays the diagnosis image in which at least one of contrast, color density, and the degree of transmittance of the person image or the geometric pattern image is changed over time, on the display 210.

The diagnosis image may just include an image (a geometric pattern picture or the like) that is preferred by the subject with developmental disorder, and an image (a personal picture or the like) other than the aforementioned image. For example, as the image other than the image preferred by the subject with developmental disorder, a nature image may be used. The nature image may just be an image of a natural object or an image that is associated with a natural object, other than the geometric image. For example, an image (a still image or a moving image) obtained such that a person, an animal, a plant, a landscape of nature, or the like is captured by a camera may be used as the nature image. Further, an image (a still image or a moving image) of a character that mimics a person or an animal may be used as the nature image.

Figure 33A:
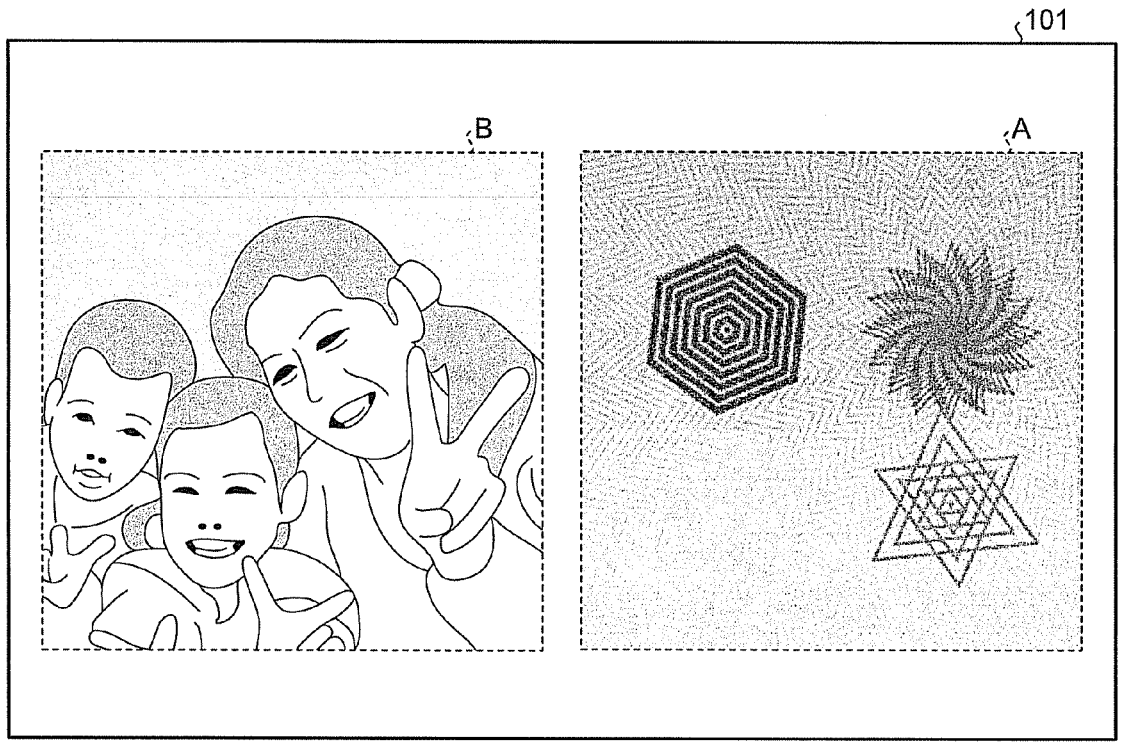
FIG. 33A is an explanatory diagram illustrating an example of a diagnosis image of a third modification.

FIGS. 33A to 33E are explanatory diagrams illustrating examples of diagnosis images. Note that the diagnosis images may be either a still image or a moving image (picture). However, the moving image is desirable because a subject can easily gaze at. As illustrated in FIG. 33A, the diagnosis image includes a region (geometric pattern region A) in which the geometric pattern picture is displayed on the right of a display screen 101, and a region (person region B) in which the person picture is displayed on the left of the display screen 101.

Figure 34A:
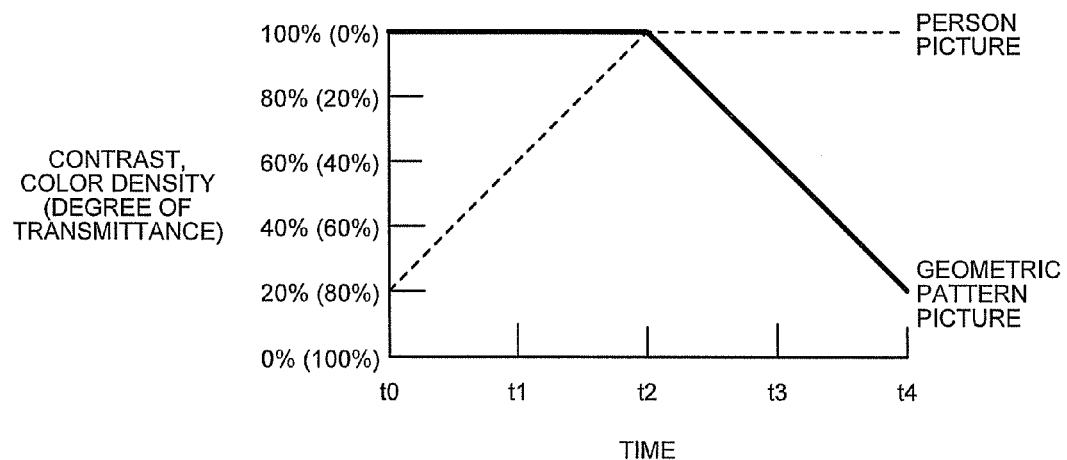
FIG. 34A is a diagram illustrating an example of change of an attribute of a person picture and a geometric pattern picture with respect to time.
Figure 34B:
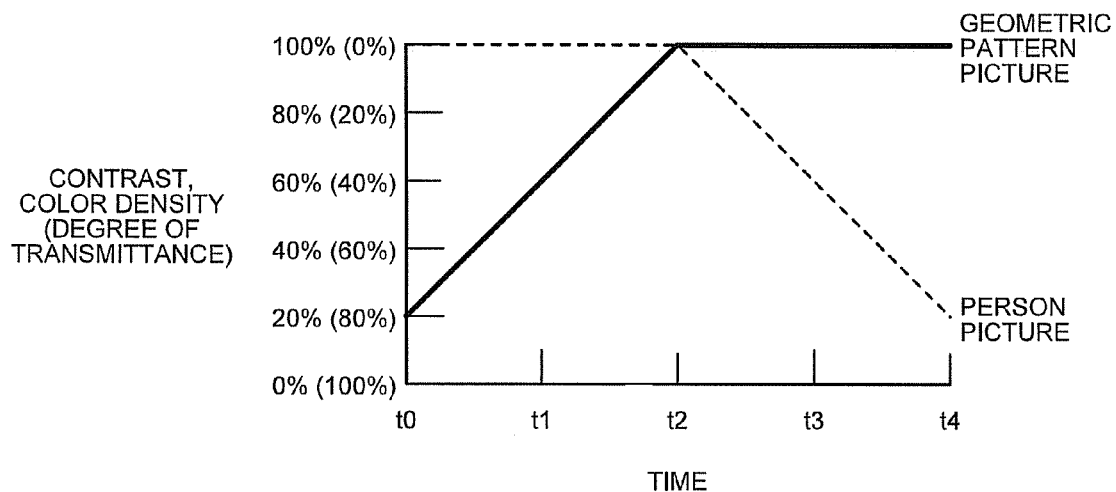
FIG. 34B is a diagram illustrating an example of change of an attribute of a person picture and a geometric pattern picture with respect to time.

FIGS. 34A and 34B are diagrams illustrating examples of change of an attribute of the person picture and the geometric pattern picture with respect to time. In FIGS. 34A and 34B, the horizontal axis represents time, and the vertical axis represents the contrast, the color density, and the degree of transmittance of the pictures. The contrast is expressed by a ratio where the lowest contrast is 0% and the highest contrast is 100%. The color density is expressed by a ratio where the density being 0 is 0% and the density having the same value as the original image is 100%. Note that the degree of transmittance may be changed, instead of changing the color density. For example, the degree of transmittance may be changed such that the degree of transmittance of 100% corresponds to the color density of 0%, and the degree of transmittance of 0% corresponds to the color density of 100%.

It is desirable to simultaneously change the contrast and the color density. However, only one of the contrast and the color density may be changed. Further, when the person picture and the geometric pattern picture are superimposed on a background and displayed, the degree of transmittance may just be changed.

Display of the entire pictures is terminated at a time t4. The output controller 353 does not change the geometric pattern picture from a time t0 that is the start of display to a time t2, and changes the contrast and the color density (the degree of transmittance) of the person picture from 20% (80%) to 100% (0%). Further, the output controller 353 does not change the person picture from the time t2 to the time t4, and changes the contrast and the color density (the degree of transmittance) of the geometric pattern picture from 100% (0%) to 20% (80%). The description within the brackets is description about the degree of transmittance. That is, the geometric pattern picture is not changed from the time t0 that is the start of display to the time t2, and the contrast and the color density of the person picture are changed from 20% to 100%. Then, from the time t2 to the time t4, the person picture is not changed, and the contrast and the color density of the geometric pattern picture are changed from 100% to 20%. Further, as for the degree of transmittance, the geometric pattern picture is not changed from the time t0 that is the start of display to the time t2, and the degree of transmittance of the person picture is changed from 80% to 0%. Then, from the time t2 to the time t4, the person picture is not changed, and the degree of transmittance of the geometric pattern picture is changed from 0% to 80%. Accordingly, the person picture gradually clearly stands out until the time t2, and the geometric pattern picture gradually fades out on and after the time t2.

FIG. 34B illustrates an example of a case where the states of change of the person picture and the geometric pattern picture are interchanged with respect to FIG. 34A. The output controller 353 may display a diagnosis image like FIG. 34B. As illustrated in FIGS. 34A and 34B, the output controller 353 may display the diagnosis image in which the contrast, the color density, the degree of transmittance, and the like of the person picture and the geometric pattern picture are changed in a contradictory manner over time.

Figure 33B:
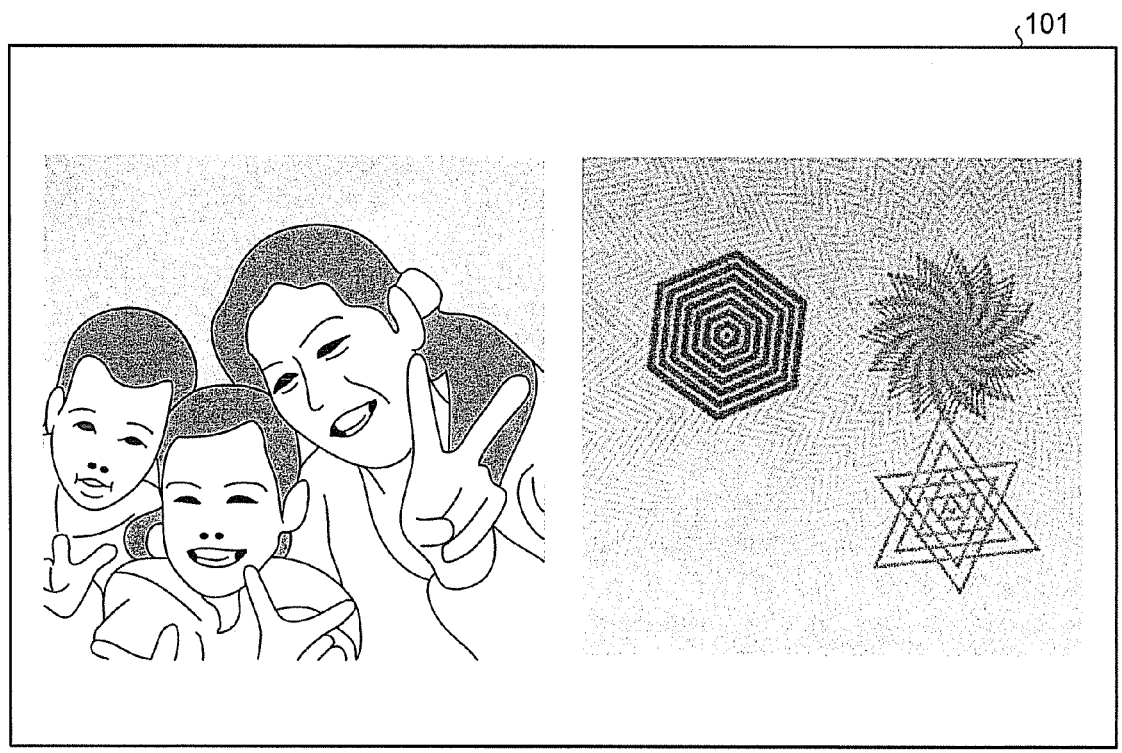
FIG. 33B is an explanatory diagram illustrating an example of a diagnosis image of the third modification.
Figure 33C:
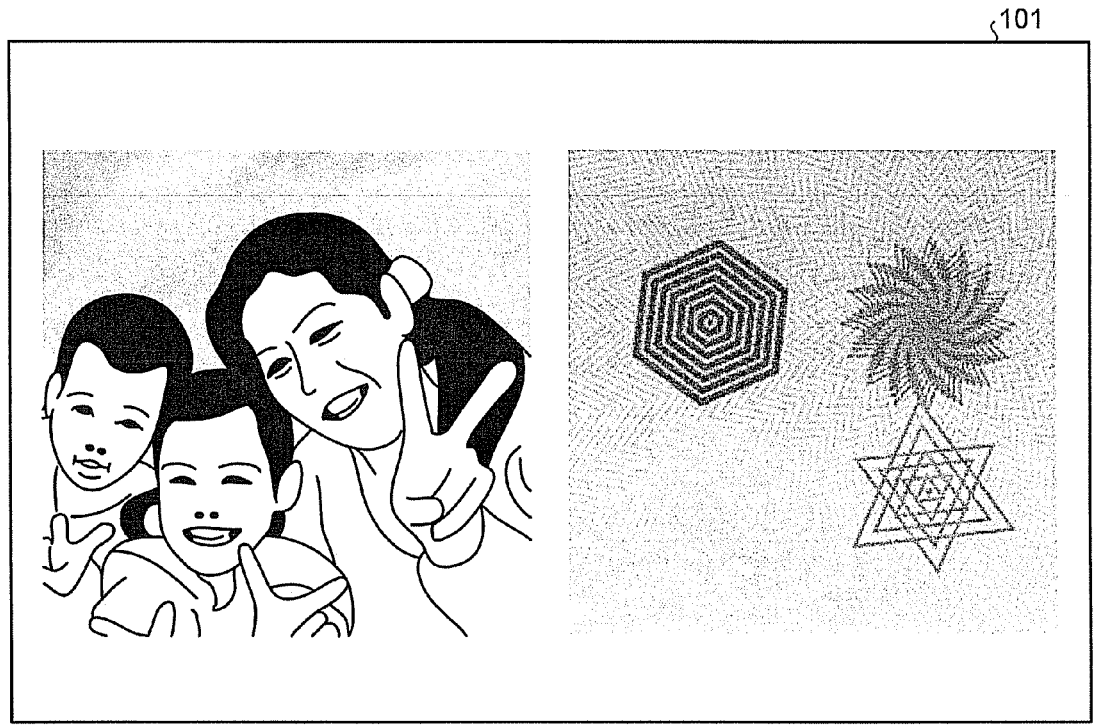
FIG. 33C is an explanatory diagram illustrating an example of a diagnosis image of the third modification.
Figure 33D:
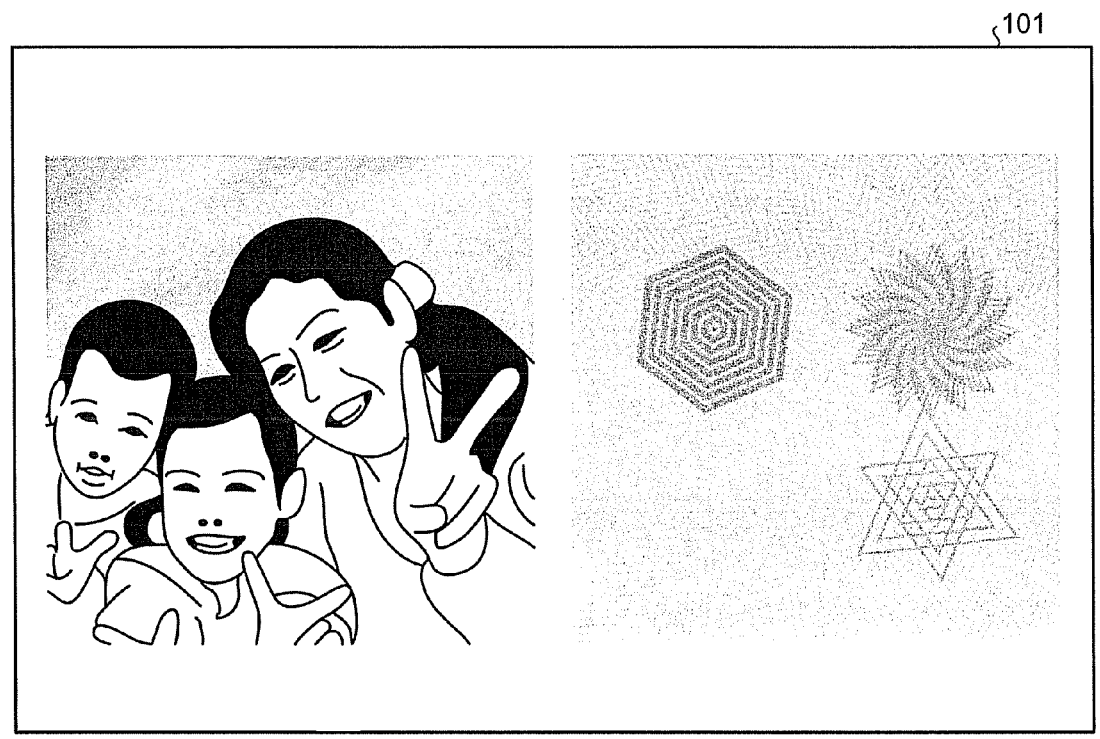
FIG. 33D is an explanatory diagram illustrating an example of a diagnosis image of the third modification.
Figure 33E:
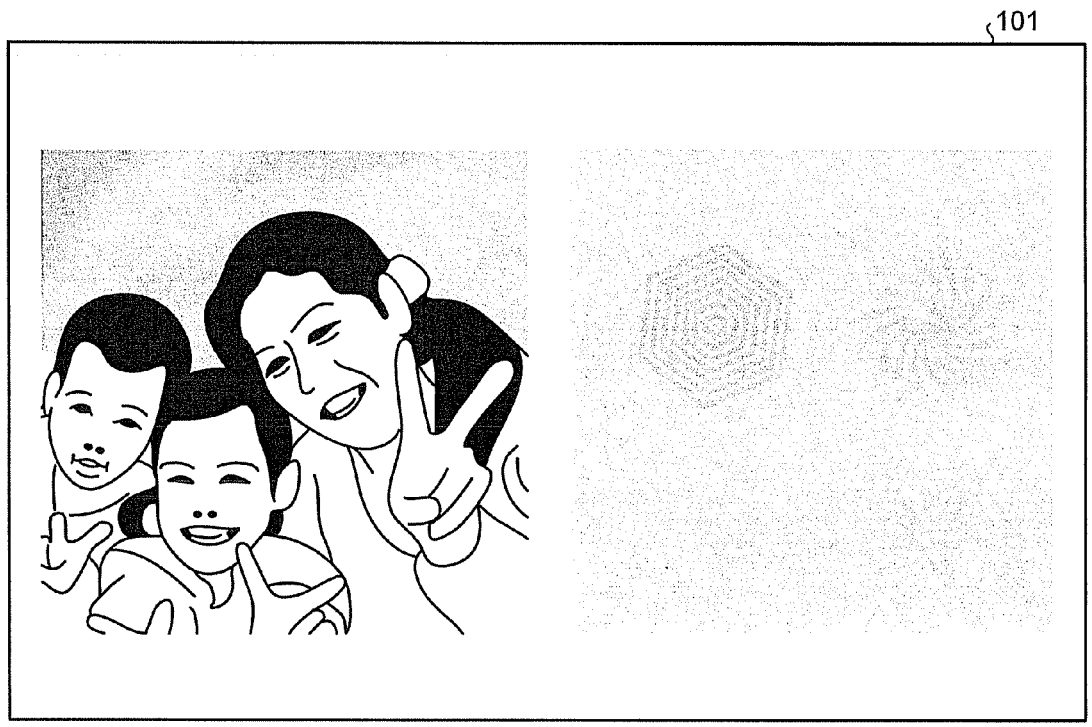
FIG. 33E is an explanatory diagram illustrating an example of a diagnosis image of the third modification.

FIGS. 33A to 33E illustrate examples of pictures displayed when the pictures are changed like FIG. 34A. FIG. 33A is an example of the diagnosis image at the time t0 of FIG. 34A. For convenience of description, both of the person picture and the geometric pattern picture are the same images in the respective drawings. However, in practice, the pictures are moving images, and thus different images corresponding to different scenes are displayed. FIG. 33B is an example of the diagnosis image at a time t1. FIG. 33C is an example of the diagnosis image at the time t2. FIG. 33D is a display screen at the time t3. FIG. 33E is the display screen at the time t4.

Figure 35A:
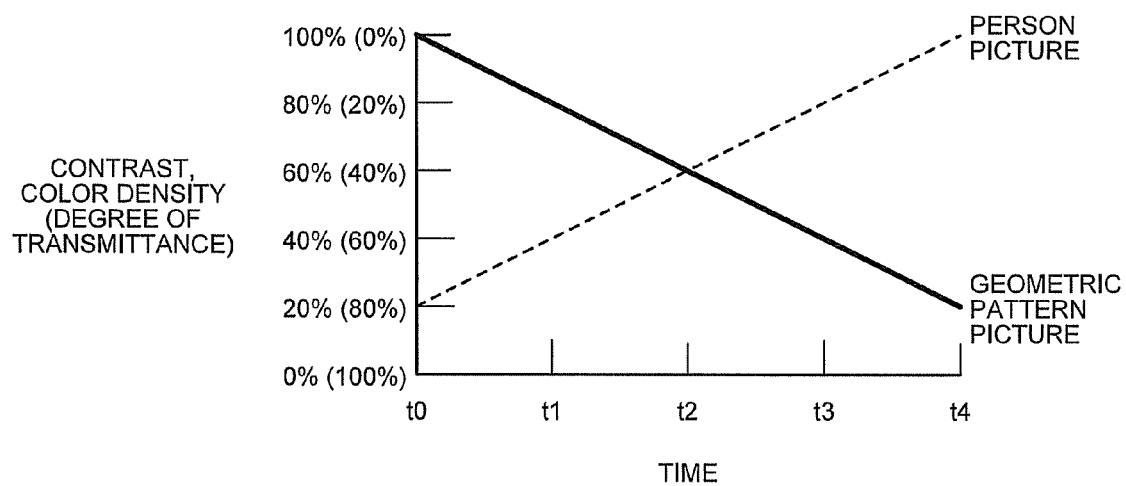
FIG. 35A is a diagram illustrating another example of change of an attribute of a person picture and a geometric pattern picture with respect to time.
Figure 35B:
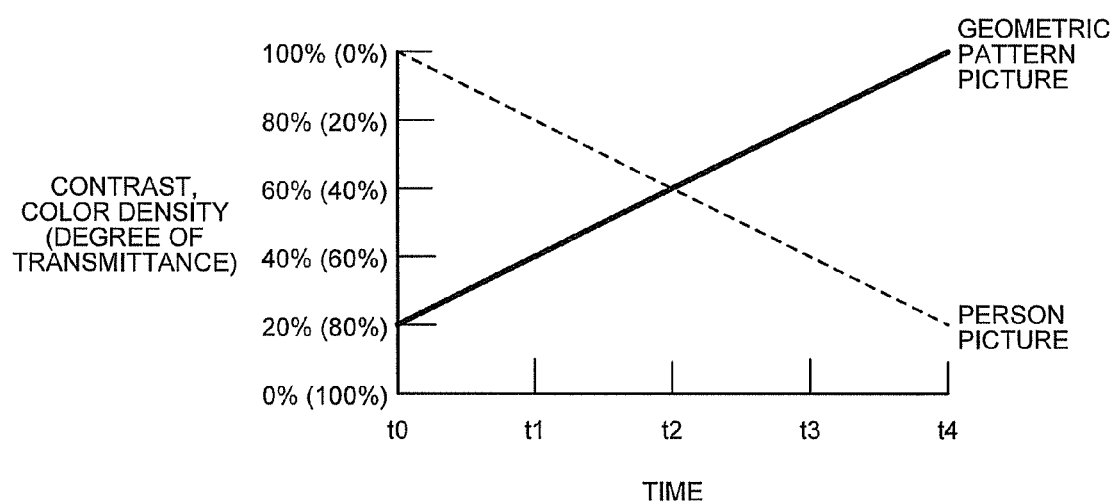
FIG. 35B is a diagram illustrating another example of change of an attribute of a person picture and a geometric pattern picture with respect to time.

FIGS. 35A and 35B are diagrams illustrating other examples of change of the contrast, the color density, and the degree of transmittance of the person picture and the geometric pattern picture with respect to time. Similarly to FIGS. 34A and 34B, in FIGS. 35A and 35B, the horizontal axis represents time, and the vertical axis represents the contrast, the color density, and the degree of transmittance of the pictures. It is desirable to simultaneously change the contrast and the color density. However, only one of the contrast and the color density may be changed. Further, when the person picture and the geometric pattern picture are superimposed on a background and displayed, the degree of transmittance may just be changed.

Display of the entire pictures is terminated at the time t4. At the time t0 to the time t4, the output controller 353 changes the contrast and the color density (the degree of transmittance) of the person picture from 20% (80%) to 100% (0%). Further, the output controller 353 changes the contrast and the color density (the degree of transmittance) of the geometric pattern picture from 100% (0%) to 20% (80%). The description in the brackets is description about the degree of transmittance. That is, from the time t0 that is the start of display to the time t4, the contrast and the color density of the person picture is changed from 20% to 100%, and the contrast and the color density of the geometric pattern picture is changed from 100% to 20%. Further, as for the degree of transmittance, from the time t0 that is the start of display to the time t4, the degree of transmittance of the person picture is changed from 80% to 0%, and the degree of transmittance of the geometric pattern picture is changed from 0% to 80%. Accordingly, the person picture gradually clearly stands out, and the geometric pattern picture gradually fades out.

FIG. 35B illustrates an example of a case where the states of change of the person picture and the geometric pattern picture are interchanged with respect to FIG. 35A. The output controller 353 may display a diagnosis image like FIG. 35B.

The change illustrated in FIGS. 34A, 34B, 35A, and FIG. 35B is an example, and change is not limited to the example. FIGS. 34A, 34B, 35A, and 35B are examples in which the contrast, the color density, and the degree of transmittance are continuously changed. However, the contrast, the color density, and the degree of transmittance may be changed in a stepwise manner. Further, the contrast, the color density, and the degree of transmittance do not need to be linearly changed, and may be changed in a curved manner. If the change is rapidly performed, the change easily attracts the subject's attention. Therefore, it is desirable to perform change such that a rate of change of the attributes per unit time becomes a fixed value or less. Values indicating the contrast and the color density are examples, and are not limited to the example. In the present embodiment, the contrast, the color density, and the degree of transmittance are changed. However, one of them may be changed.

Figure 36A:
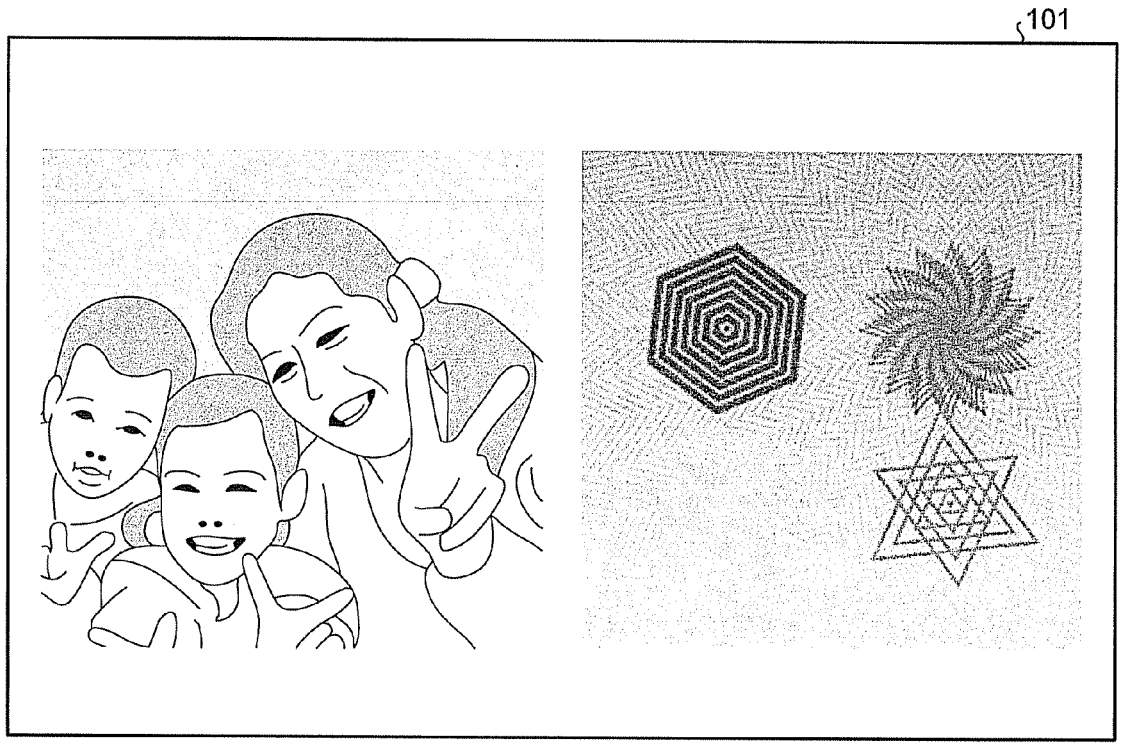
FIG. 36A is an explanatory diagram illustrating another example of a diagnosis image.
Figure 36B:
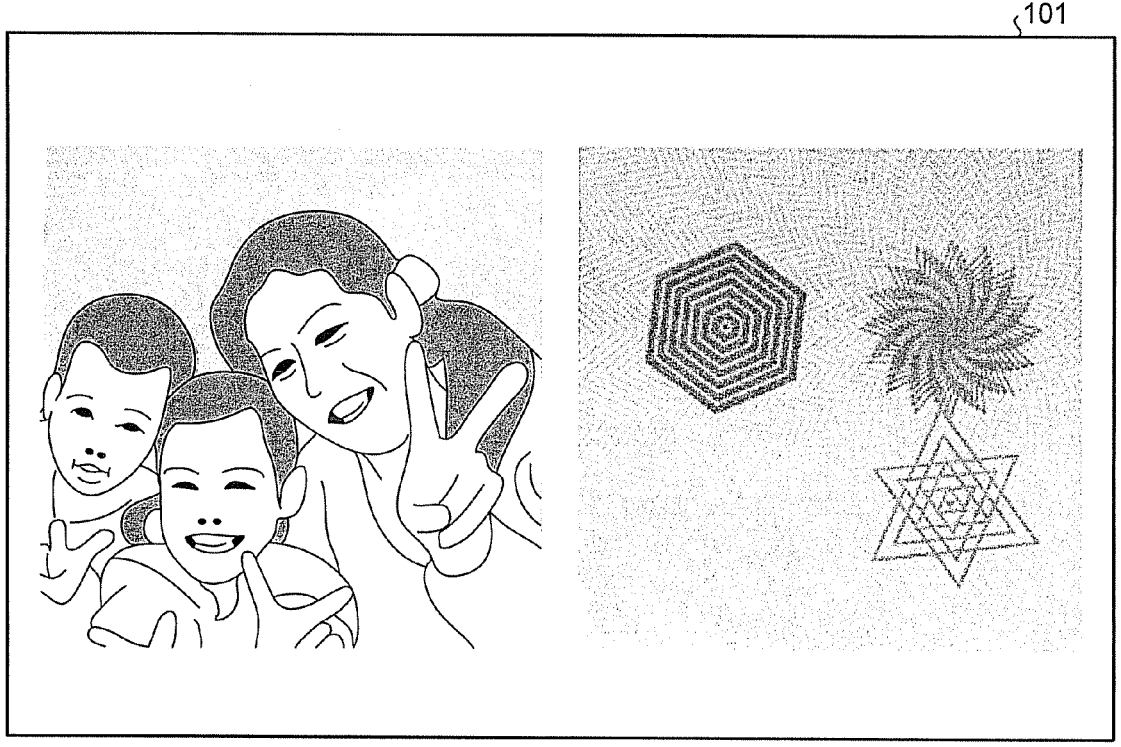
FIG. 36B is an explanatory diagram illustrating another example of a diagnosis image.
Figure 36C:
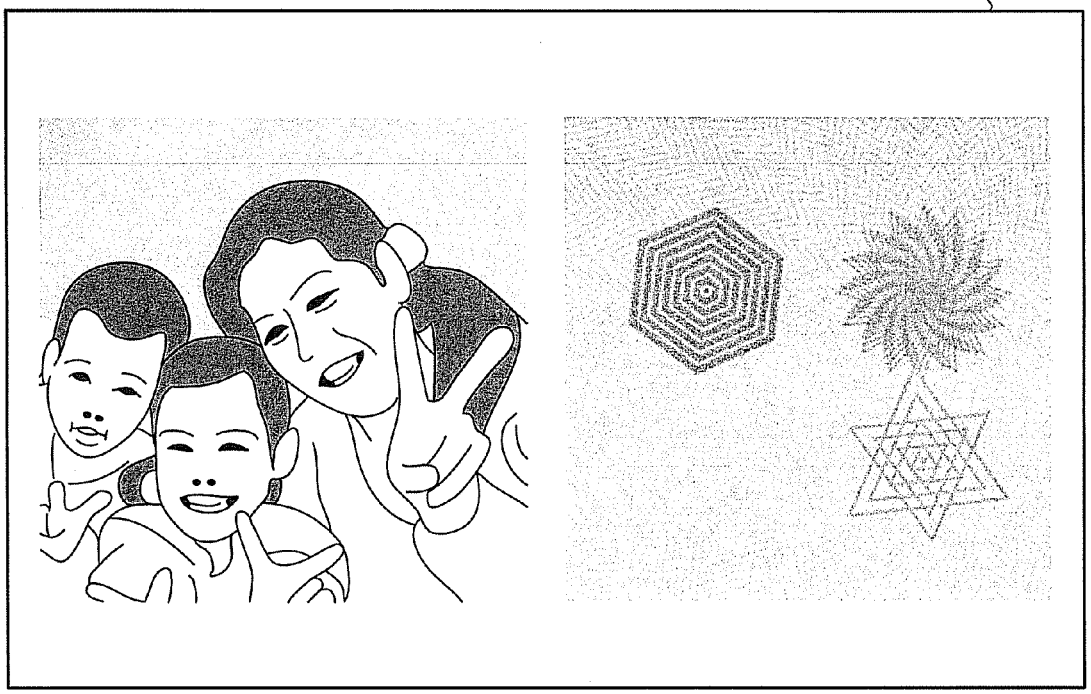
FIG. 36C is an explanatory diagram illustrating another example of a diagnosis image.
Figure 36D:
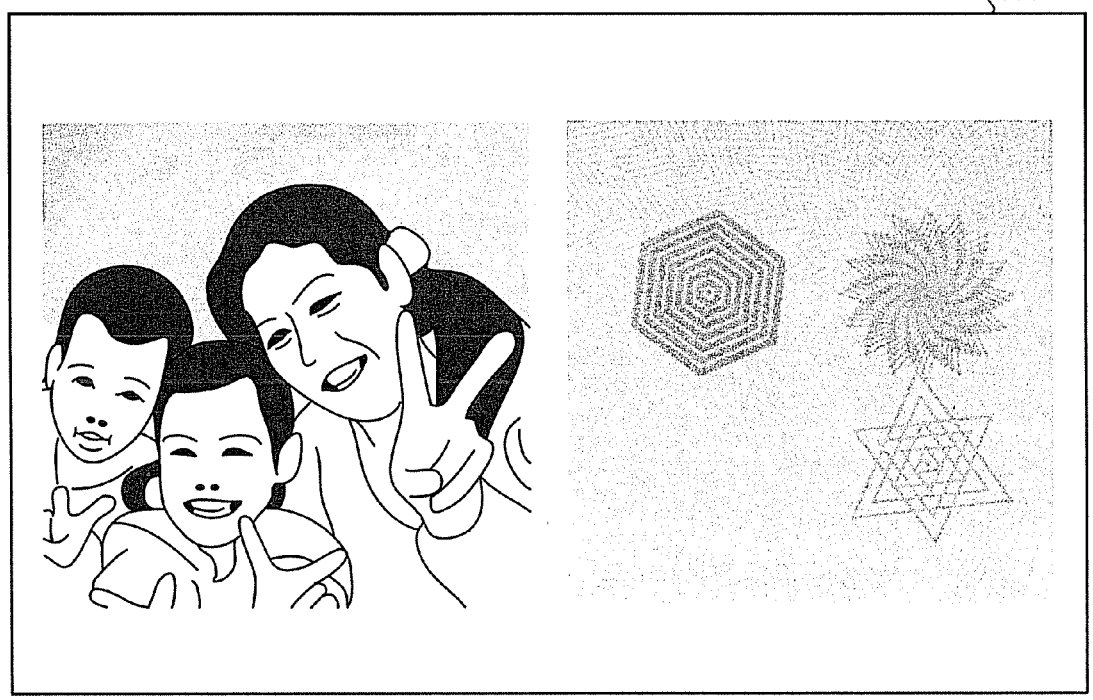
FIG. 36D is an explanatory diagram illustrating another example of a diagnosis image.
Figure 36E:
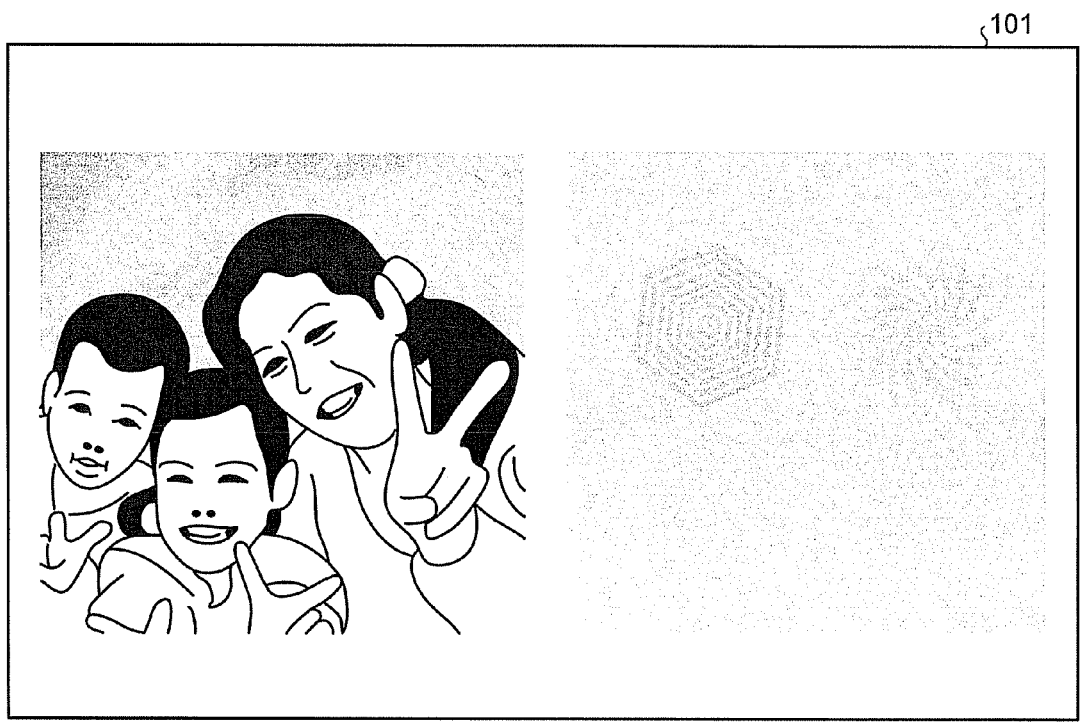
FIG. 36E is an explanatory diagram illustrating another example of a diagnosis image.

FIGS. 36A to 36E are explanatory diagrams illustrating other examples of diagnosis images. FIGS. 36A to 36E illustrate examples of pictures displayed when the picture are changed like FIG. 35A. FIG. 36A is an example of the diagnosis image at the time t0 of FIG. 35A. For convenience of description, both of the person picture and the geometric pattern picture are the same images in the respective drawings. However, in practice, since the pictures are moving images, and thus different images corresponding to different scenes are displayed. FIG. 36B is an example of the diagnosis image at the time t1. FIG. 36C is an example of the diagnosis image at the time t2. FIG. 36D is an example of the diagnosis image at the time t3. FIG. 36E is an example of the diagnosis image at the time t4.

Figure 37:
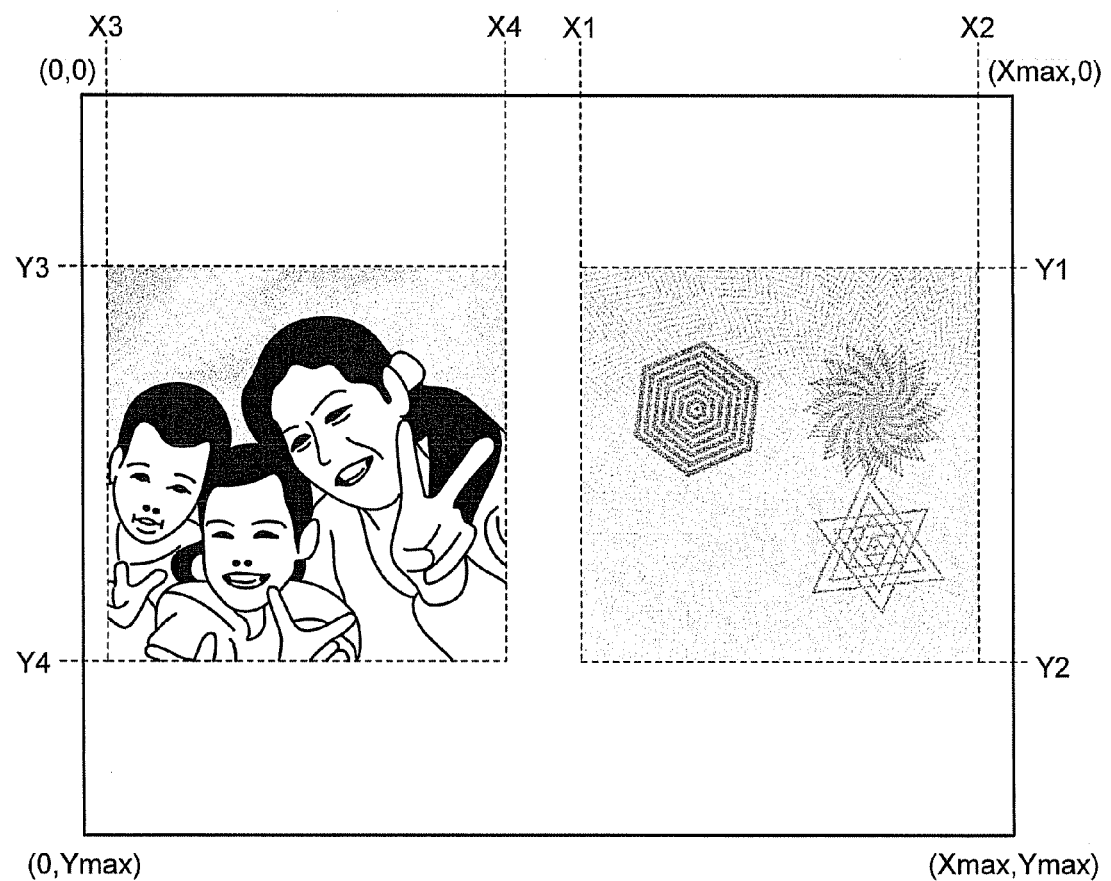
FIG. 37 is a diagram illustrating an example of coordinates of an image displayed in a display.

FIG. 37 is a diagram illustrating an example of coordinates of images displayed on the display 210. In the coordinate system on the display 210, an upper left position is the origin, which is different from the above-described world coordinates (space coordinates) for gaze point detection.

The number of pixels of the display 210 is Xmax×Ymax. The X coordinate of a left side of the geometric pattern region A is X1, the X coordinate of a right side is X2, the Y coordinate of an upper side is Y1, and the Y coordinate of a lower side is Y2. The X coordinate of a left side of the person region B is X3, the X coordinate of a right side is X4, the Y coordinate of an upper side is Y3, and the Y coordinate of a lower side is Y4. FIG. 37 illustrates an example in which Y1=Y3 and Y2=Y4.

Figure 38:
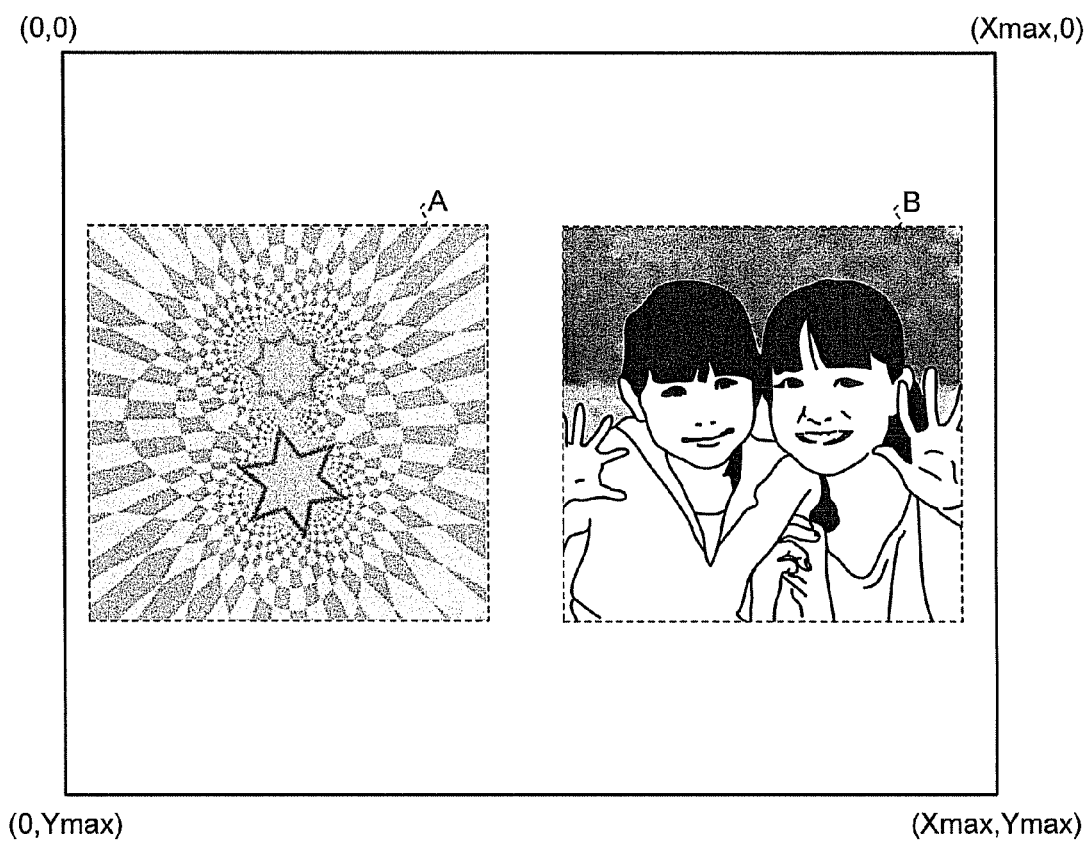
FIG. 38 is a diagram illustrating another example of coordinates of an image displayed in a display.

FIG. 38 is a diagram illustrating another example of coordinates of images displayed on the display 210. FIG. 38 is an example of a diagnosis image in which arrangement of the person picture and the geometric pattern picture is different from FIG. 37. That is, in FIG. 38, the left is the geometric pattern picture, and the right is the person picture.

An example of diagnosis supporting processing using a diagnosis image like FIG. 37 or 38 will be described using FIGS. 39, and 40A to 40C.

Figure 39:
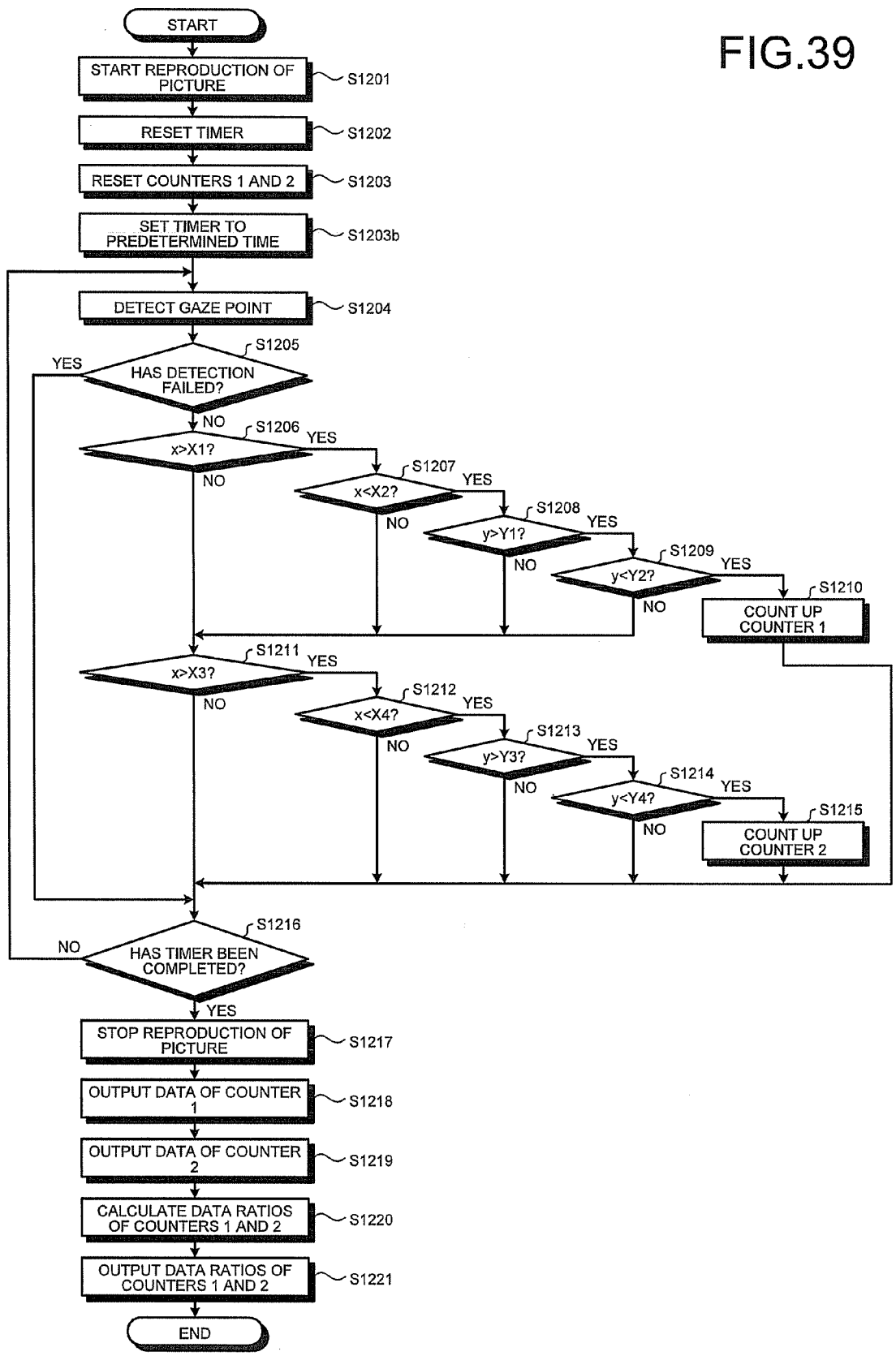
FIG. 39 is a flowchart illustrating an example of diagnosis supporting processing using one picture (diagnosis image).

FIG. 39 is a flowchart illustrating an example of diagnosis supporting processing using one picture (diagnosis image). In this example, the person picture and the geometric pattern picture are composited in advance.

First, the output controller 353 starts reproduction of the picture (diagnosis image) (step S1201). Next, the output controller 353 resets a timer that measures a slightly shorter time than a reproduction time of the picture (step S1202). A gaze point detector 352 resets (initializes) a counter 1 that is counted up when a subject gazes at an inside of the geometric pattern region A, and a counter 2 that is counted up when a subject gazes at an inside the person region B (step S1203). Processing of next step S1203b will be described below. This step S1203b may not be executed.

Gaze point measurement is performed for each one frame of stereo cameras that capture an image in synchronization with each other, for example. That is, the gaze point is measured in each predetermined time interval. Count values of the counter 1 and the counter 2 correspond to gaze times.

Next, the gaze point detector 352 performs the gaze point detection (step S1204). The gaze point detector 352 determines whether the gaze point detection has failed (step S1205). When an image of a pupil or a corneal reflection cannot be obtained due to a blink or the like, the gaze point detection fails. Further, when the gaze point does not exist in the display screen 101 (when the subject looks at a thing other than the display screen 101), the gaze point detection fails.

When the gaze point detection has failed (Yes in step S1205), the gaze point detector 352 moves onto step S1216 so as not to influence the counter 1 and the counter 2. When the gaze point detection has succeeded (No in step S1205), the gaze point detector 352 checks whether the x coordinate of the detected gaze point on the display 210 is larger than X1 (step S1206). When the x coordinate is larger than X1 (Yes in step S1206), the gaze point detector 352 checks whether the x coordinate on the display 210 is smaller than X2 (step S1207). When the x coordinate is smaller than X2 (Yes in step S1207), the gaze point detector 352 checks whether the y coordinate on the display 210 is larger than Y1 (step S1208). When the y coordinate is larger than Y1 (Yes in step S1208), the gaze point detector 352 checks whether the y coordinate on the display 210 is smaller than Y2 (step S1209). When the y coordinate is smaller than Y2 (Yes in step S1209), the gaze point exists an inside of the geometric pattern region A, the gaze point detector 352 counts up the counter 1 (step S1210).

When the condition of counting up of the counter 1 is not satisfied (No in step S1206, No in step S1207, No in step S1208, and No in step S1209), the gaze point detector 352 proceeds to step S1211.

The gaze point detector 352 checks whether the x coordinate of the detected gaze point on the display 210 is larger than X3 (step S1211). When the x coordinate is larger than X3 (Yes in step S1211), the gaze point detector 352 checks whether the x coordinate on the display 210 is smaller than X4 (step S1212). When the x coordinate is smaller than X4 (Yes in step S1212), the gaze point detector 352 checks whether the y coordinate on the display 210 is larger than Y3 (step S1213). When the y coordinate is larger than Y3 (Yes in step S1213), the gaze point detector 352 checks whether the y coordinate on the display 210 is smaller than Y4 (step S1214). When the y coordinate is smaller than Y4 (Yes in step S1214), the gaze point exists inside the person region B. Therefore, the gaze point detector 352 counts up the counter 2 (step S1215).

After the counters 1 and 2 are counted up, or the condition of counting up of the counter 2 is not satisfied (No in step S1211, No in step S1212, No in step S1213, or No in step S1214), the gaze point detector 352 proceeds to step S1216.

The output controller 353 determines whether the timer has been completed in order to confirm end of the picture (step S1216). When the timer has not been completed (No in step S1216), the output controller 353 returns to step S1204, and repeats the processing.

When the timer has been completed (Yes in step S1216), the output controller 353 stops the reproduction of the picture (step S1217). Next, the evaluator 354 outputs data of the counter 1 (step S1218). The data of the counter 1 corresponds to the gaze time of the geometric pattern region A. Next, the evaluator 354 outputs data of the counter 2 (step S1219). The data of the counter 2 corresponds to the gaze time of the person region B. Next, an evaluator 354 calculates ratios of the counter 1 and the counter 2, as an evaluation value (step S1220). For example, the evaluator 354 calculates an evaluation value that indicates a ratio of the counter 2 to the counter 1. The calculated evaluation value serves as a guideline of a possibility of developmental disorder. For example, as the ratio of gazing at the geometric pattern region A is higher, the possibility of developmental disorder is determined to become higher. The evaluator 354 outputs the calculated evaluation value (ratio data) (step S1221).

In the example of FIG. 39, at the beginning where the picture is display, many subjects gaze at the geometric pattern with high contrast. The contrast of the person picture becomes higher over time. The neurotypical subject is changed to gaze at the person picture with high contrast. Meanwhile, the subject with developmental disorder continuously gazes at the geometric pattern picture without moving the gaze point, because having a high interest in the geometric pattern.

Therefore, in the output of step S1221, the subject with developmental disorder has a high ratio of the counted value of the counter 1. Further, the contrast and the color density (the degree of transmittance) are changed in a relative manner. Therefore, the degree of standing out of the picture is changed. In the present modification, the degree of standing out is reversed regardless of the picture. Therefore, movement of the gaze point of the neurotypical subject occurs at any point in time.

As illustrated in FIGS. 34B and 35B, in the case where the contrast of the person picture is high in the beginning, converse phenomenon takes place. That is, the neurotypical subject has less movement of the gaze point, and the subject with developmental disorder has a lot of movement of the gaze point. Since the subject with developmental disorder has a strong tendency (persistency) to continuously gaze at the diagnosis image that the subject is gazing at, the patterns of FIGS. 34A and 35A are more desirable.

Figure 40A:
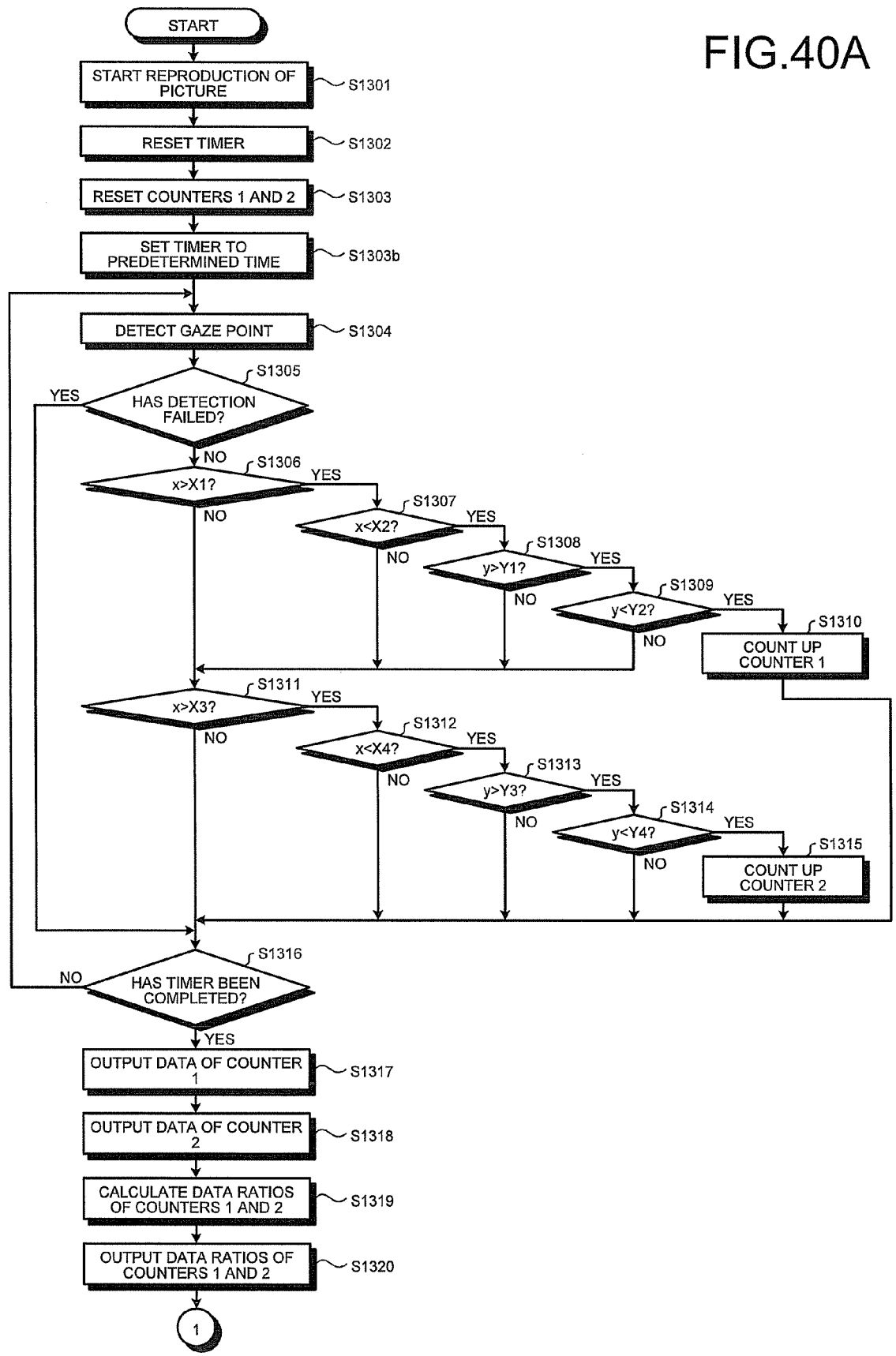
FIG. 40A is a flowchart illustrating an example of diagnosis supporting processing using two pictures.
Figure 40B:
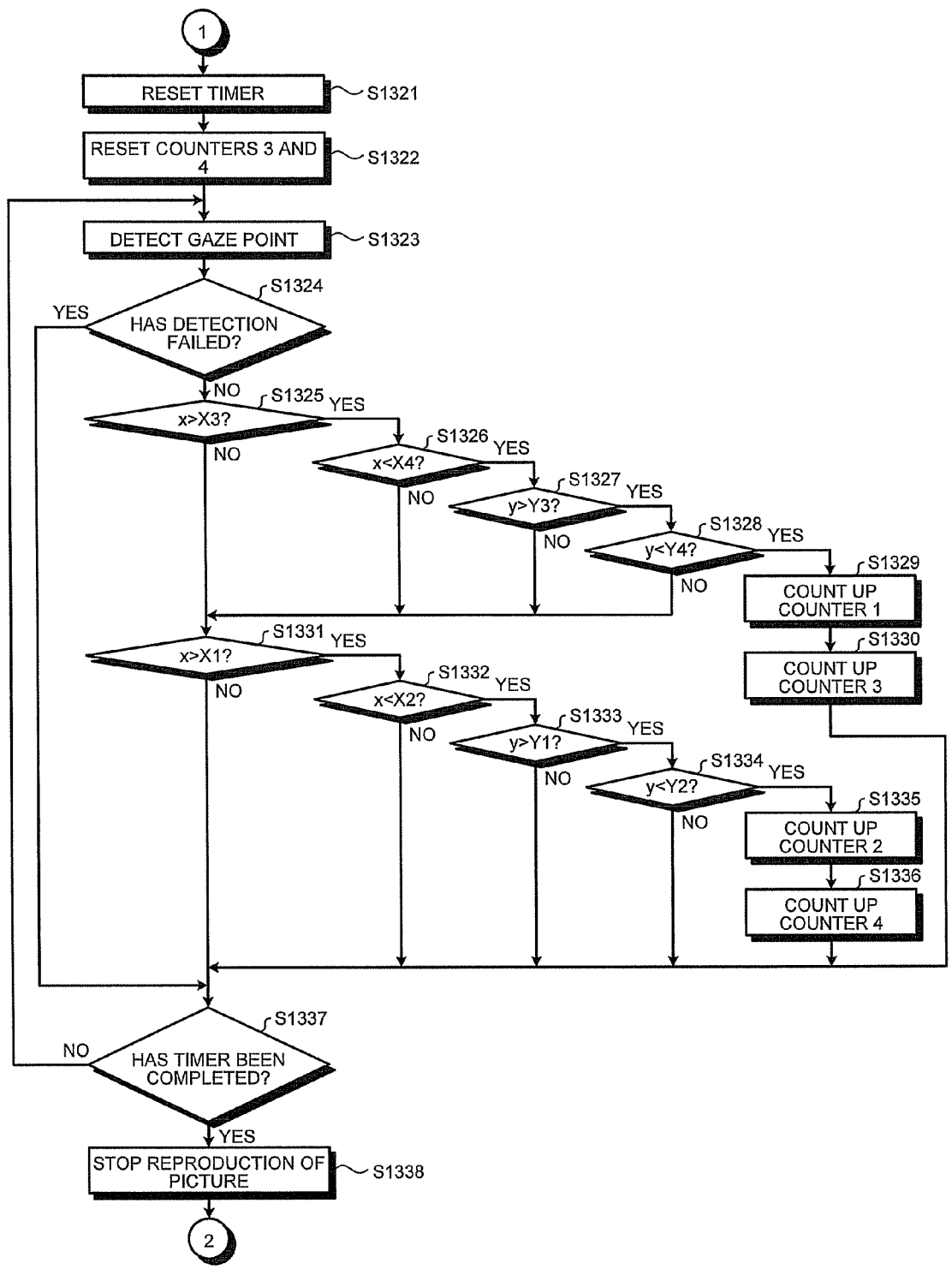
FIG. 40B is a flowchart illustrating an example of diagnosis supporting processing using two pictures.
Figure 40C:
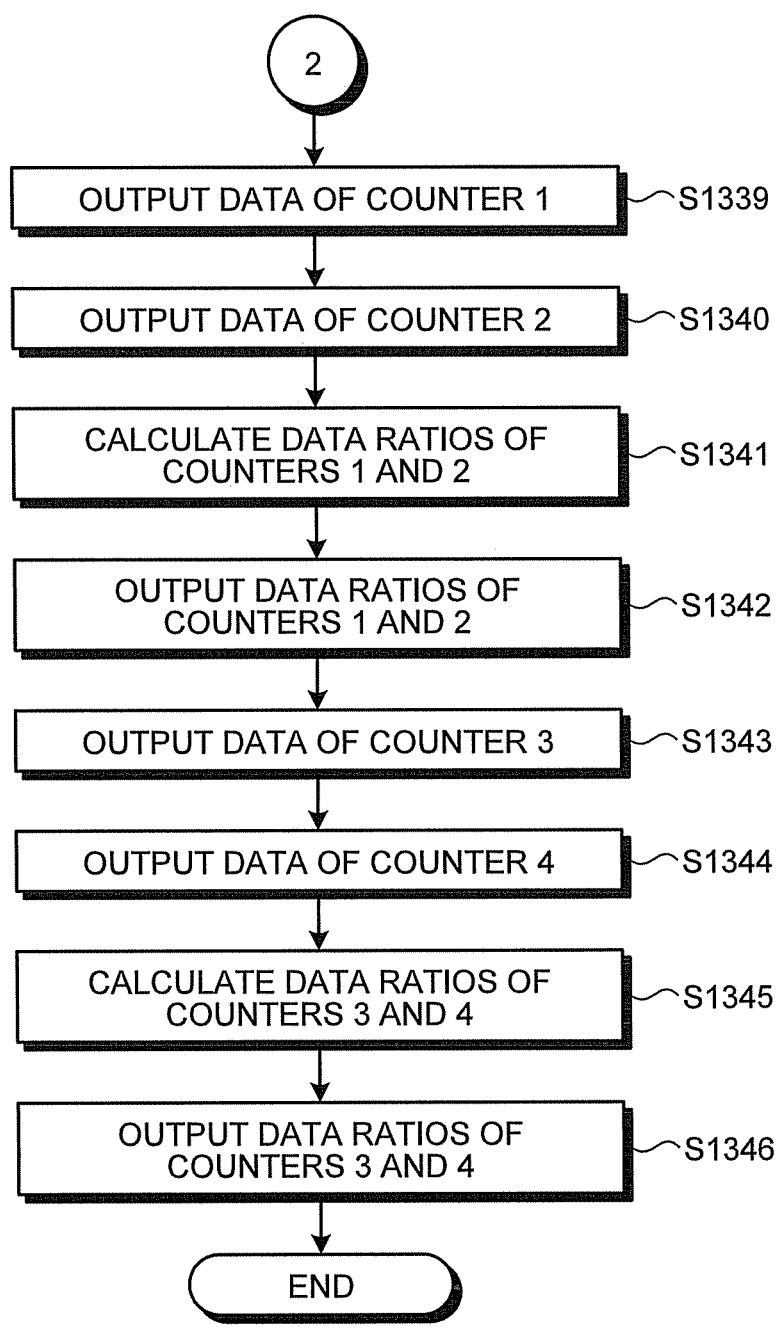
FIG. 40C is a flowchart illustrating an example of diagnosis supporting processing using two pictures.

FIGS. 40A to 40C are flowcharts illustrating an example of diagnosis supporting processing using two pictures. In this example, the person picture and the geometric pattern picture are composited in advance. Further, the two pictures are connected, and are configured to be reproduced in a predetermined time. In the example below, in the first half, the picture of FIGS. 33A to 33E is reproduced, and in the latter half, the picture in which arrangement of the geometric pattern picture and the person picture is reversed, like FIG. 38, is reproduced.

Processing from step S1301 to S1320 is equal to steps S1201 to S1216, and steps S1218 to S1221 of FIG. 39.

However, roles of the counter 1 and the counter 2 are different from FIG. 39. In the example of FIGS. 40A to 40B, the counter 1 and the counter 2 are counters that are counted through the picture 1 and the picture 2 that are the two pictures. However, the counter 1 and the counter 2 output a count result of the picture 1 and the ratio thereof, at the time of end of the picture 1 (steps S1317 to S1320). Following that, in the picture 2, the counter 1 and the counter 2 are counted, and a total value and a ratio are output (steps S1339 to S1342).

FIG. 40B will be described. Immediately before step S1321, reproduction of the second picture is started. The output controller 353 resets a timer that measures a slightly shorter time than a reproduction time of the second picture (picture 2) (step S1321). The gaze point detector 352 resets a counter 3 that is counted up when a subject gazes at an inside of the geometric pattern region A in the picture 2, and a counter 4 that is counted up when a subject gazes at the person region B (step S1322).

Next, the gaze point detector 352 performs the gaze point detection (step S1323). The gaze point detector 352 determines whether gaze point detection has failed (step S1324). When the gaze point detection has failed (Yes in step S1324), the gaze point detector 352 moves onto step S1337 so as not to influence the counter 1, the counter 2, the counter 3, and the counter 4.

When the gaze point detection has succeeded (No in step S1324), the gaze point detector 352 checks whether the x coordinate of the detected gaze point on the display 210 is larger than X3 (step S1325). When the x coordinate is larger than X3 (Yes in step S1325), the gaze point detector 352 checks whether the x coordinate on the display 210 is smaller than X4 (step S1326). When the x coordinate is smaller than X4 (Yes in step S1326), the gaze point detector 352 checks whether the y coordinate on the display 210 is larger than Y3 (step S1327). When the y coordinate is larger than Y3 (Yes in step S1327), the gaze point detector 352 checks whether the y coordinate on the display 210 is smaller than Y4 (step S1328). When the y coordinate is smaller than Y4 (Yes in step S1328), the gaze point exists inside the geometric pattern region A, and thus the gaze point detector 352 counts up the counter 1 (step S1329), and counts up the counter 3 (step S1330).

When the condition of counting up of the counters 1 and 3 is not satisfied (No in step S1325, No in step S1326, No in step S1327, or No in step S1328), the gaze point detector 352 proceeds to step S1331.

The gaze point detector 352 checks whether the x coordinate of the detected gaze point on the display 210 is larger than X1 (step S1331). When the x coordinate is larger than X1 (Yes in step S1331), the gaze point detector 352 checks whether the x coordinate on the display 210 is smaller than X2 (step S1332). When the x coordinate is smaller than X2 (Yes in step S1332), the gaze point detector 352 checks whether the y coordinate on the display 210 is larger than Y1 (step S1333). When the y coordinate is larger than Y1 (Yes in step S1333), the gaze point detector 352 checks whether the y coordinate on the display 210 is smaller than Y2 (step S1334). When the y coordinate is smaller than Y2 (Yes in step S1334), the gaze point exists inside the person region B, and thus the gaze point detector 352 counts up the counter 2 (step S1335), and counts up the counter 4 (step S1336).

The output controller 353 determines whether the timer has been completed in order to confirm end of the picture (step S1337). When the timer has not been completed (No in step S1337), the output controller returns to step S1323, and the processing is repeated.

When the timer has been completed (Yes in step S1337), the output controller 353 stops the reproduction of the picture (step S1338).

Next, the evaluator 354 outputs data of the counter 1 (step S1339). Here, the data of the counter 1 output here corresponds to the gaze time of the geometric pattern region A in the picture 1 and the picture 2. Next, the evaluator 354 outputs data of the counter 2 (step S1340). The data of the counter 2 output here corresponds to the gaze time of the person region B in the picture 1 and the picture 2. The evaluator 354 calculates the ratios of the counter 1 and the counter 2, as the evaluation value (step S1341). This evaluation value serves as a guideline of the possibility of developmental disorder. For example, as the ratio of gazing at the geometric pattern region A is higher, the possibility of developmental disorder is determined to become higher. The evaluator 354 outputs the calculated evaluation value (ratio data) (step S1342).

Further, the evaluator 354 outputs data of the counter 3 (step S1343). The data of the counter 3 corresponds to the gaze time of the geometric pattern region A in the picture 2. Next, the evaluator 354 outputs data of the counter 4 (step S1344). The data of the counter 4 corresponds to the gaze time of the person region B in the picture 2. Next, the evaluator 354 calculates ratios of the counter 3 and the counter 4, as the evaluation value (step S1345). This evaluation value also serves as a guideline of the possibility of developmental disorder. For example, as the ratio of gazing at the geometric pattern region A is higher, the possibility of developmental disorder is determined to become higher. The evaluator 354 outputs the calculated evaluation value (ratio data) (step S1346).

Here, the tendency of the subject can be obtained by comparison of a count result of the picture 1 and the ratio thereof (steps S1317 to S1320), and a count result of the picture 2 and the ratio thereof (steps S1343 to S1346). For example, when the subject has a tendency to look at a picture from a right side of the screen, the count value of the geometric pattern region A tends to be increased in the picture 1, and the count value of the geometric pattern region A tends to be decreased in the picture 2. When the subject looks at the picture in a right and left balanced manner, it can be considered that the subject gazes at the picture according to his/her liking after starting to look at a central portion.

Further, as illustrated in step S1203b of FIG. 39 and step S1303b of FIG. 40A, the gaze point detector 352 may perform processing of waiting for elapse of a predetermined time, using a-timer or the like. The predetermined time is a time until a decrease in the contrast and the color density of the geometric pattern picture is started in the picture 1, for example. In the example of FIG. 34A, the predetermined time corresponds to the time from the time t0 to the time t2. In the first picture portion, most of the subjects gaze at the geometric pattern picture. Therefore, by performing of the waiting processing like steps S1203b and S1303b, the first half time is not measured, and only the latter half can be measured. In this case, the detection accuracy can be further improved. Further, the diagnosis supporting processing may be executed using three or more pictures. In this case, for example, a total value of the count results and a total value of the evaluation values in all of the pictures may be output.

Further, the change of the contrast and the like of the picture may be realized by use of a picture with such contrast and the like in advance.

As described above, according to the third modification, following effects can be obtained, for example.

(1) Even if there is a difference in the degrees of attention of the person picture and the geometric pattern picture, a favorabe detection is possible, and the detection accuracy is improved.

(2) An influence of an individual difference of a subject becomes small.

(3) Production of a picture (diagnosis image) for diagnosis support becomes easy.

Second Embodiment

In a second embodiment, an eye gaze detection device and an eye gaze detection method are realized, which can further simplify a device configuration compared with the first embodiment.

Hereinafter, an eye gaze detection device and an eye gaze detection method of the second embodiment will be described in detail based on the drawings. Note that the present invention is not limited by this embodiment. Hereinafter, an example of using an eye gaze detection device, as a diagnosis supporting device that supports diagnosis of developmental disorder and the like, using eye gaze detection results will be described. An applicable device is not limited to the diagnosis supporting device.

An eye gaze detection device (diagnosis supporting device) of the present embodiment detects an eye gaze, using an illuminator installed in one place. Further, the eye gaze detection device (diagnosis supporting device) of the present embodiment calculates a corneal curvature center position in a high accurate manner, using a result of measurement obtained by causing a subject to gaze at one point, before detection of the eye gaze.

Note that the illuminator is an element that includes a light source and can irradiate an eye ball of the subject with light. The light source is an element that emits light, such as a light emitting diode (LED). The light source may be configured' from one LED, or may be configured such that a plurality of LEDs is combined and is arranged at one place. Hereinafter, "light source" may be used as a term that indicates the illuminator.

Figure 41:
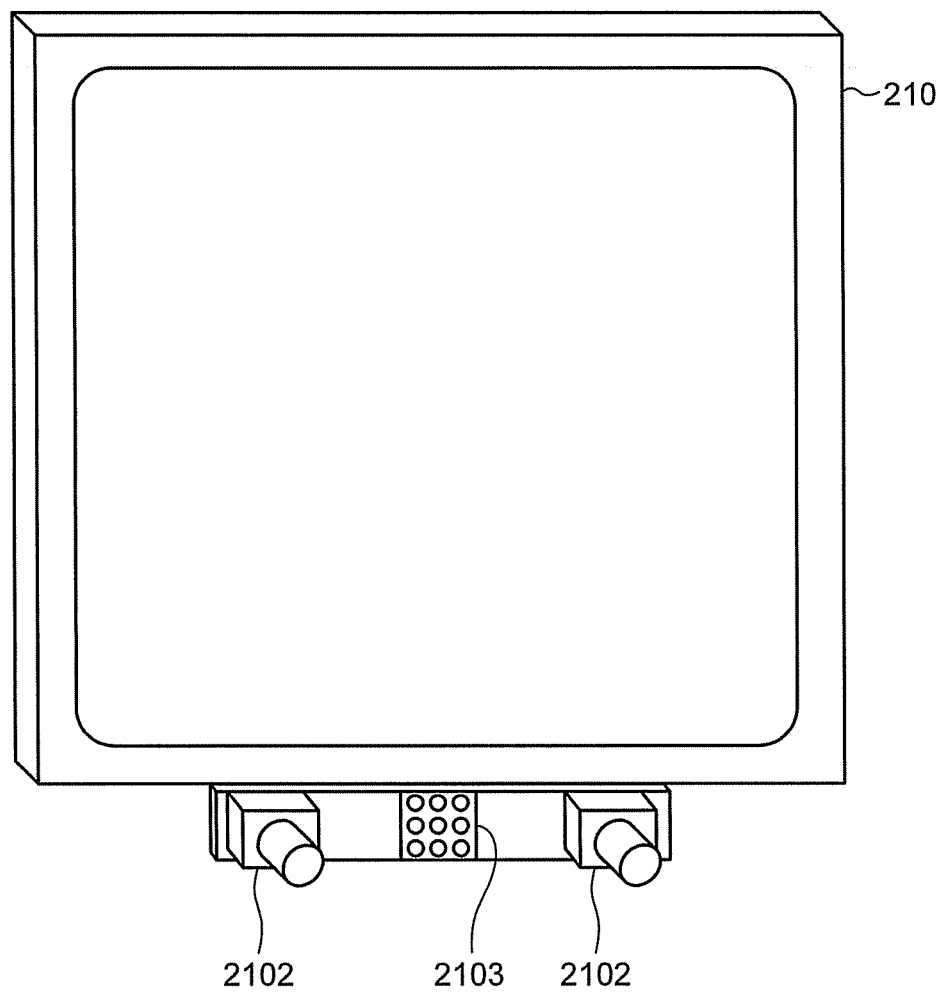
FIG. 41 is a diagram illustrating an example of arrangement of a display, stereo cameras, and an infrared light source of a second embodiment.
Figure 42:
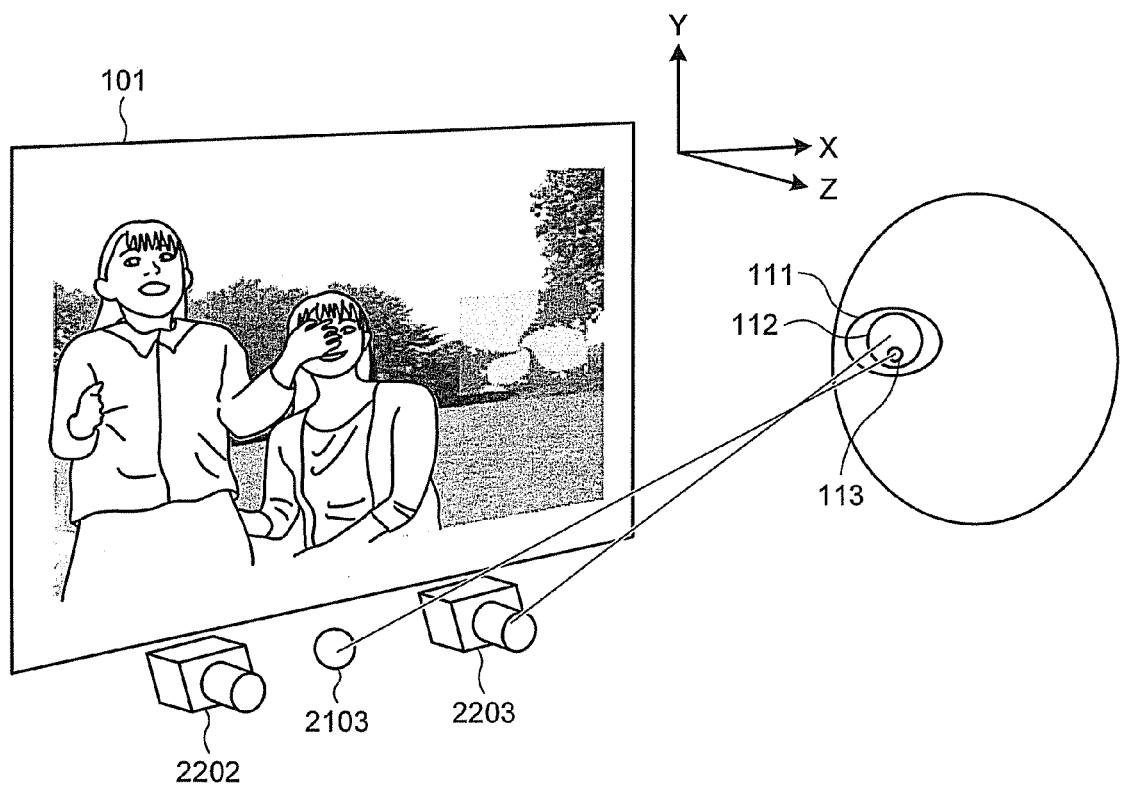
FIG. 42 is a diagram illustrating an example of arrangement of a display, stereo cameras, an infrared light source, and a subject of the second embodiment.

FIGS. 41 and 42 are diagrams illustrating an example of arrangement of a display, stereo cameras, an infrared light source, and a subject of the second embodiment. Note that the same configuration as the first embodiment is denoted with the same reference sign, and description may be omitted.

As illustrated in FIG. 41, a diagnosis supporting device of the second embodiment includes a display 210, a stereo camera 2102, and an LED light source 2103. The stereo camera 2102 is arranged under the display 210. The LED light source 2103 is arranged at a center position of two cameras included in the stereo camera 2102. The LED light source 2103 is, for example, a light source that irradiates the subject with a near infrared ray with a wavelength of 850 nm. FIG. 41 illustrates an example in which the LED light source 2103 (illuminator) is configured from nine LEDs. Note that, in the stereo camera 2102, a lens that can transmit near infrared light with a wavelength of 850 nm is used.

As illustrated in FIG. 42, the stereo camera 2102 includes a right camera 2202 and a left camera 2203. The LED light source 2103 irradiates an eye ball 111 of the subject with the near infrared light. In an image obtained by the stereo camera 2102, a pupil 112 is reflected at low luminance and becomes dark, and corneal reflection 113 caused in the eye ball 111, as a virtual image, is reflected at high luminance and becomes bright. Therefore, positions of the pupil 112 and the corneal reflection 113 on the image can be obtained by the two cameras (the right camera 2202 and the left camera 2203).

Further, three-dimensional world coordinate values of positions of a pupil 112 and a corneal reflection 113 are calculated from positions of the pupil 112 and the corneal reflection 113 obtained by the two cameras. In the present embodiment, as the three-dimensional world coordinates, a coordinate in an up and down direction is a Y coordinate (the up direction is +), a coordinate in a transverse direction is an X coordinate (the right direction is +), and a coordinate in a depth direction is a Z coordinate (the front side is +), where a middle position on a display screen 101 is the origin.

Figure 43:
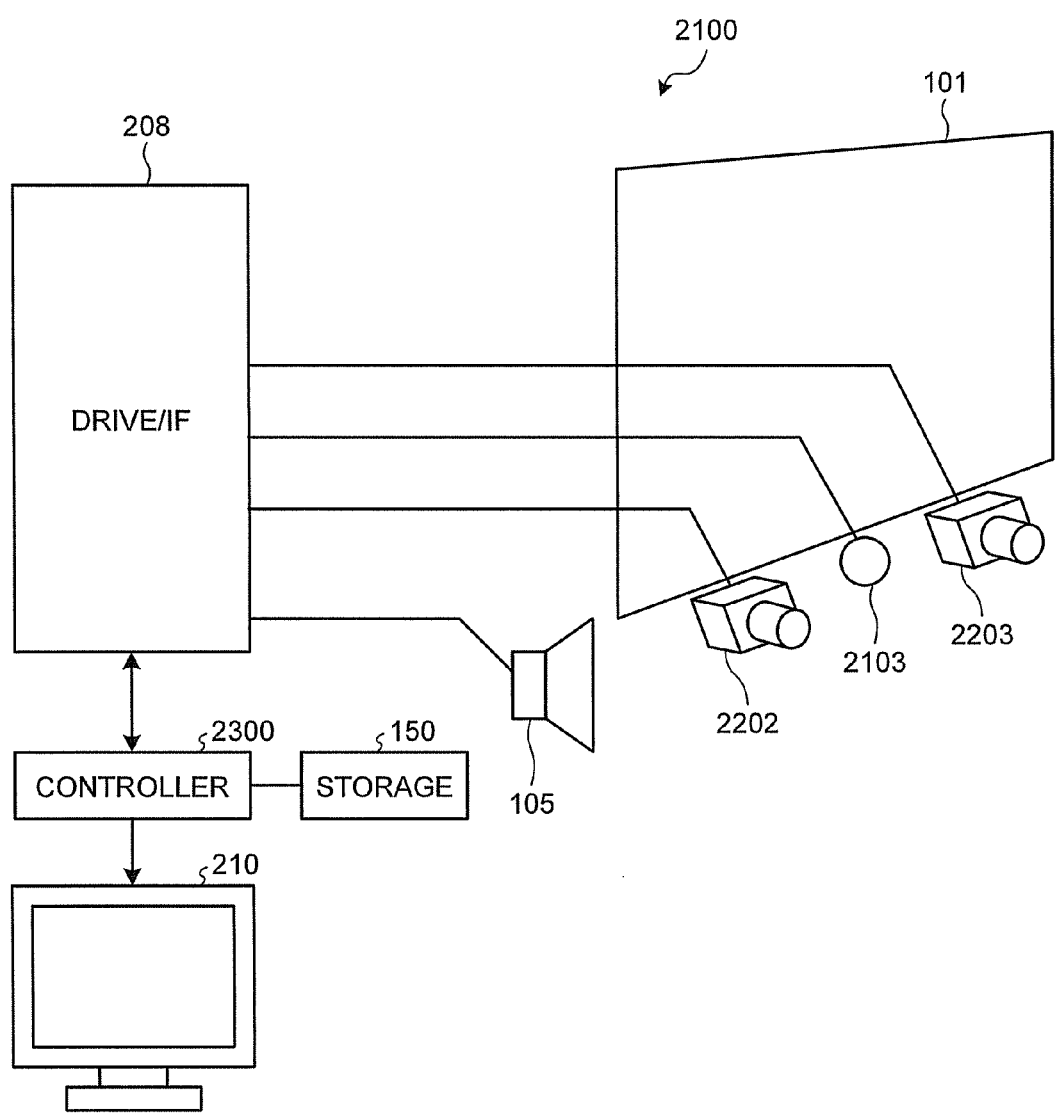
FIG. 43 is a diagram illustrating an outline of functions of a diagnosis supporting device.

FIG. 43 is a diagram illustrating an outline of functions of a diagnosis supporting device 2100 of the second embodiment. FIG. 43 illustrates the configurations illustrated in FIGS. 41 and 42, and other configurations used for driving the aforementioned configurations. As illustrated in FIG. 43, the diagnosis supporting device 2100 includes the right camera 2202, the left camera 2203, the LED light source 2103, a speaker 105, a drive/IF (interface) 208, a controller 2300, a storage 150, and the display 210. In FIG. 43, a positional relationship between a display screen 101, and the right camera 2202 and the left camera 2203 is illustrated in an easily understandable manner. The display screen 101 is a screen displayed in the display 210. Note that the driver and the IF may be integrated or separated.

The speaker 105 functions as an audio output unit that outputs an audio and the like for prompting the subject to pay attention, at the time of calibration and the like.

The drive/IF 208 drives units included in the stereo camera 2102. Further, the drive/IF 208 serves as an interface between the units included in the stereo camera 2102, and the controller 2300.

The controller 2300 can be realized by a computer that includes a control device such as a central processing unit (CPU), a storage device such as read only memory (ROM) and random access memory (RAM), a communication I/F that is connected with a network and performs communication, and a bus that connects the units.

The storage 150 stores various types of information such as a control program, a measurement result, and a diagnosis support result. The storage 150 stores an image to be displayed in the display 210, and the like. The display 210 displays various types of information such as an object image for diagnosis, and the like.

Figure 44:
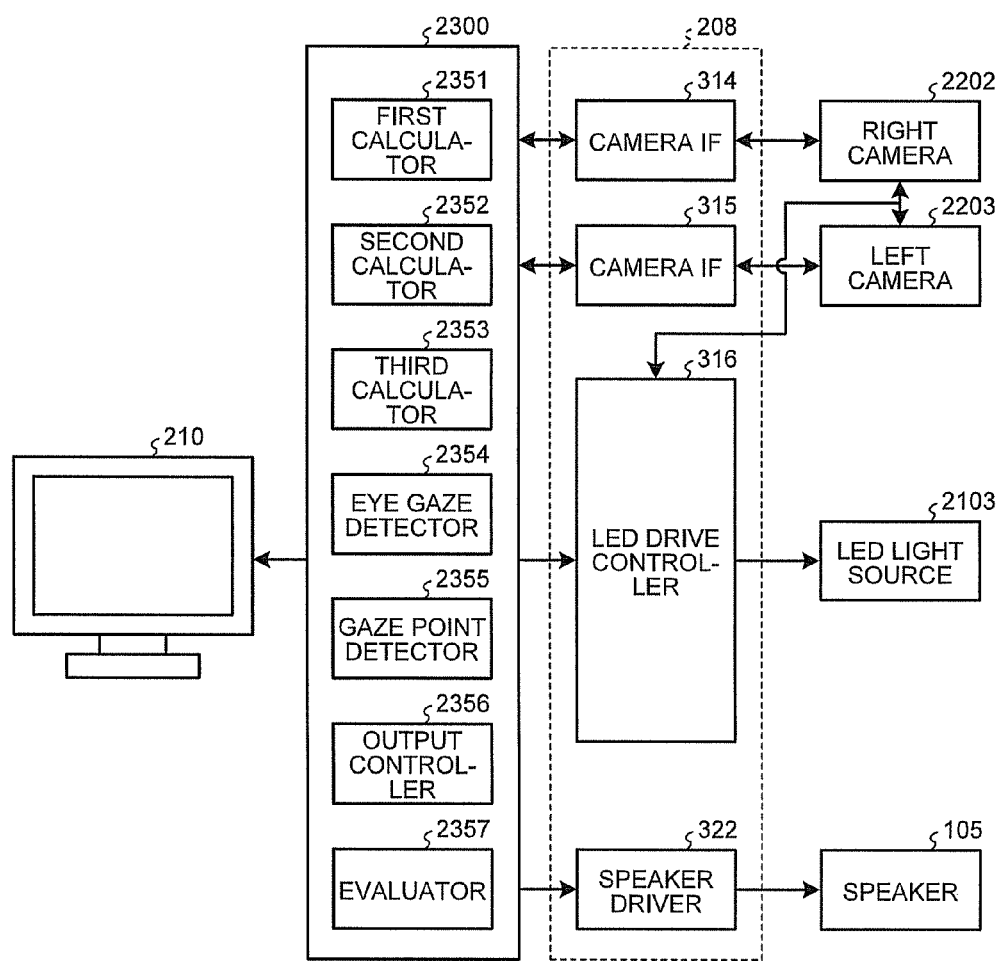
FIG. 44 is a block diagram illustrating an example of detailed functions of respective units illustrated in FIG. 43.

FIG. 44 is a block diagram illustrating an example of detailed functions of the respective units illustrated in FIG. 43. As illustrated in FIG. 44, the display 210 and the drive/IF 208 are connected to the controller 2300. The drive/IF 208 includes camera IFs 314 and 315, an LED drive controller 316, and a speaker driver 322.

The right camera 2202 and the left camera 2203 are connected to the drive/IF 208 through the camera IFs 314 and 315, respectively. The drive/IF 208 drives these cameras to capture the subject.

The speaker driver 322 drives the speaker 105. Note that the diagnosis supporting device 2100 may include an interface (printer IF) for being connected with a printer as a print unit. Further, the printer may be included inside the diagnosis supporting device 2100.

A controller 2300 controls the entire diagnosis supporting device 2100. The controller 2300 includes a first calculator 2351, a second calculator 2352, a third calculator 2353, an eye gaze detector 2354, a gaze point detector 2355, an output controller 2356, and an evaluator 2357. Note that at least the first calculator 2351, the second calculator 2352, the third calculator 2353, and the eye gaze detector 2354 may just be included as an eye gaze detection device.

The elements (the first calculator 2351, the second calculator 2352, the third calculator 2353, the eye gaze detector 2354, the gaze point detector 2355, the output controller 2356, and the evaluator 2357) included in the controller 2300 may be realized by software (a program), may be realized by a hardware circuit, or may be realized by use of the software and the hardware circuit together.

When the elements are realized by the programs, the programs are recorded in a computer-readable recording medium such as a compact disk read only memory (CD-ROM), a flexible disk (FD), a compact disk recordable (CD-R), or a digital versatile disk (DVD) in a file in an installable format or in an executable format, and provided as a computer program product. The programs may be stored on a computer connected to a network such as the Internet, and provided by being downloaded through the network. Further, the programs may be provided or distributed through the network such as the Internet. Further, the programs may be provided by being incorporated in ROM or the like in advance.

The first calculator 2351 calculates a position (first position) of a pupil center that indicates a center of a pupil, from an image of an eye ball captured by a stereo camera 2102. The second calculator 2352 calculates a position (second position) of a corneal reflection center that indicates a center of a corneal reflection, from the captured image of an eye ball. The first calculator 2351 and the second calculator 2352 correspond to a position detector that detects the first position that indicates the center of the pupil and the second position that indicates the center of the corneal reflection.

The third calculator 2353 calculates a corneal curvature center (fourth position), from a straight line (first straight line) that connects an LED light source 2103 and the corneal reflection center. For example, the third calculator 2353 calculates a position where the distance from the corneal reflection center becomes a predetermined value, on the straight line, as the corneal curvature center. As the predetermined value, a value determined in advance from a curvature radius value of a typical cornea can be used.

An individual difference may be caused in the curvature radius value of a cornea. Therefore, there is a possibility that an error becomes large when the corneal curvature center is calculated using the value determined in advance. Therefore, the third calculator 2353 may calculates the corneal curvature center in consideration of the individual difference. In this case, the third calculator 2353 first calculates an intersection point of a straight line (second straight line) that connects the pupil center and a target position, and the first straight line that connects the corneal reflection center and the LED light source 2103, using the pupil center and the corneal reflection center calculated when the subject is caused to gaze at the target position (third position). The third calculator 2353 then calculates a distance (first distance) between the pupil center and the calculated intersection point, and stores the calculated distance in a storage 150, for example.

The target position may be any position as long as the position can be determined in advance, and three-dimensional world coordinate values can be calculated. For example, a middle position (the origin of the three-dimensional world coordinates) of the display screen 101 can be used as the target position. In this case, for example, the output controller 2356 displays an image (target image) or the like that the subject is caused to gaze at, in the target position (center) on the display screen 101. Accordingly, the subject can gaze at the target position.

The target image may be any image as long as the image can draw attention from the subject. For example, an image with a varying display form such as luminance or a color, an image having different display form from other regions, or the like can be used as the target image.

Note that the target position is not limited to the center of the display screen 101, and any position can be employed. If the center of the display screen 101 is employed as the target position, the distance between the center and any end part of the display screen 101 is minimized. Therefore, for example, a measurement error at the time of detecting the eye gaze can be made smaller.

Processing up to the calculation of the distance is executed in advance before actual detection of an eye gaze is started, for example. At the time of actual detection of an eye gaze, the third calculator 2353 calculates a position where the distance from the pupil center becomes the distance calculated in advance, on the straight line that connects the LED light source 2103 and the corneal reflection center, as the corneal curvature center. The third calculator 2353 corresponds to a calculator that calculates the corneal curvature center (fourth position), from the position of the LED light source 2103, the predetermined position (third position) that indicates a target image on a display, the position of the pupil center, and the position of the corneal reflection center.

The eye gaze detector 2354 detects the eye gaze of the subject from the pupil center and the corneal curvature center. For example, the eye gaze detector 2354 detects a direction from the corneal curvature center toward the pupil center, as an eye gaze direction of the subject.

The gaze point detector 2355 detects a gaze point of the subject, using the detected eye gaze direction. The gaze point detector 2355 detects, for example, a gaze point that is a point that the subject gazes at on the display screen 101. The gaze point detector 2355 detects an intersection point of an eye gaze vector and an XY plane, which are expressed in a three-dimensional world coordinate system as illustrated in FIG. 42, as the gaze point of the subject.

The output controller 2356 controls output of various types of information to the display 210, the speaker 105, and the like. For example, the output controller 2356 outputs the target image to the target position on the display 210. Further, the output controller 2356 controls output to the display 210, such as a diagnosis image, an evaluation result by the evaluator 2357, and the like.

The diagnosis image may just be an image according to evaluation processing based on an eye gaze (gaze point) detection result. For example, when a developmental disorder is diagnosed, a diagnosis image that includes an image (a geometrical pattern picture or the like) preferred by the subject with the developmental disorder, and another image (a picture of a person, or the like) may be used.

The evaluator 2357 performs evaluation processing based on the diagnosis image, and the gaze point detected by the gaze point detector 2355. For example, when the developmental disorder is diagnosed, the evaluator 2357 analyzes the diagnosis image and the gaze point, and evaluates whether the subject with the developmental disorder has gazed at the image that the subject prefers.

The output controller 2356 may display a diagnosis image similar to the first embodiment, and the evaluator 2357 may perform evaluation processing similar to the evaluator 354 of the first embodiment. In other words, the eye gaze detection processing (eye gaze detector 351) of the first embodiment may be replaced with eye gaze detection processing (the first calculator 2351, the second calculator 2352, the third calculator 2353, and the eye gaze detector 2354) of the second embodiment. Accordingly, an effect of the second embodiment (simplification of the device configuration, and the like) can be achieved in addition to the effect of the first embodiment.

Figure 45:
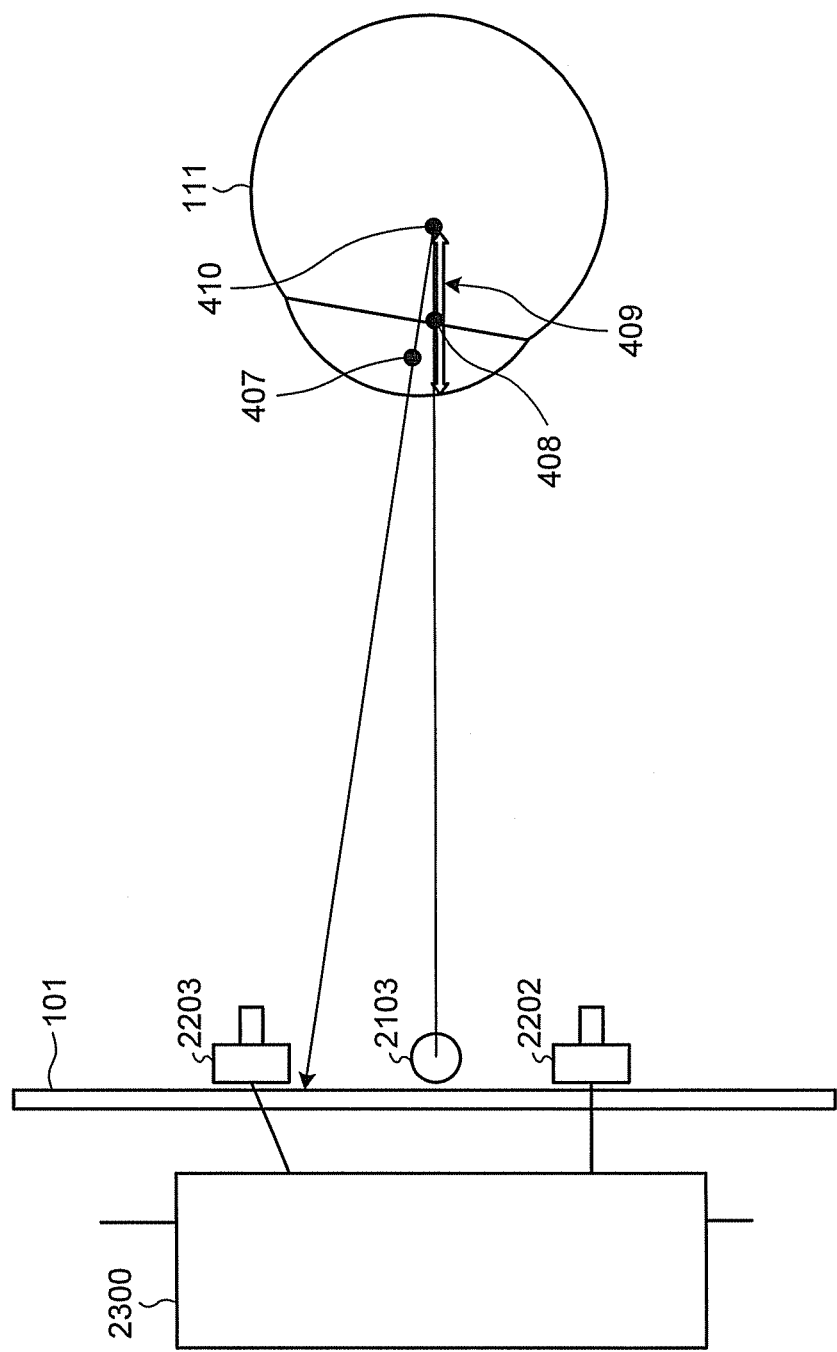
FIG. 45 is a diagram illustrating an outline of processing executed by the diagnosis supporting device of the second embodiment.

FIG. 45 is a diagram for describing an outline of processing executed by the diagnosis supporting device 2100 of the present embodiment. Elements described in FIGS. 41 to 44 are denoted with the same reference signs, and description is omitted.

A pupil center 407 and a corneal reflection center 408 respectively indicate the center of the pupil and the center of a corneal reflection point detected when the LED light source 2103 is lighted. A cornea curvature radius 409 indicates the distance from a surface of the cornea to a corneal curvature center 410.

Figure 46:
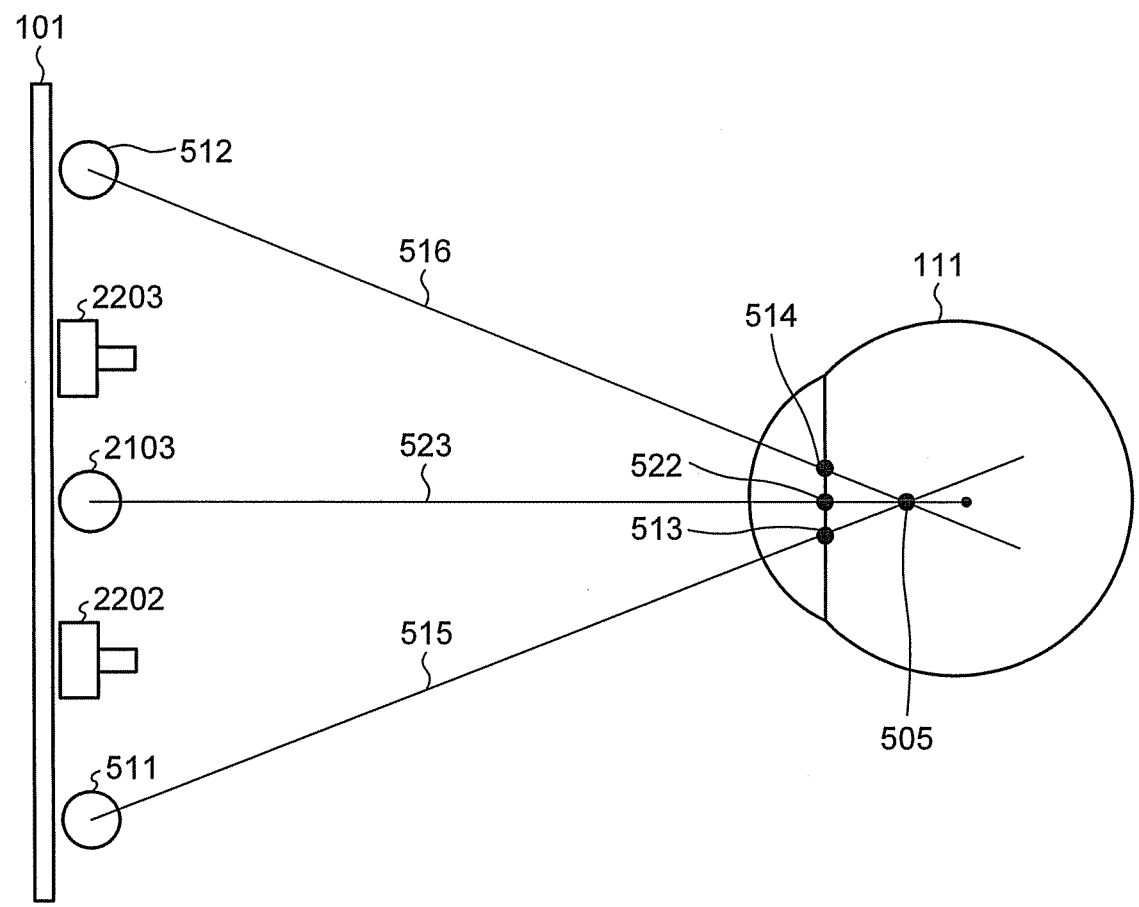
FIG. 46 is an explanatory diagram illustrating a difference between a method of using two light sources and the second embodiment using one light source.

FIG. 46 is an explanatory diagram illustrating a difference between a method using two light sources (illuminators) (hereinafter, referred to as method A), and the present embodiment using one light source (illuminator). Elements described in FIGS. 41 to 44 are denoted with the same reference signs, and description is omitted.

The method A uses two LED light sources 511 and 512, in place of the LED light source 2103. In the method A, an intersection point of a straight line 515 that connects a corneal reflection center 513 and the LED light source 511 of when the LED light source 511 irradiates the subject with light, and a straight line 516 that connects a corneal reflection center 514 and the LED light source 512 of when the LED light source 512 irradiates the subject with light is calculated. This intersection point serves as a corneal curvature center 505.

In contrast, in the present embodiment, a straight line 523 that connects a corneal reflection center 522 and the LED light source 2103 of when the LED light source 2103 irradiates the subject with light is considered. The straight line 523 passes through the corneal curvature center 505. Further, the curvature radius of a cornea is known to have a small influence due to the individual difference and have a nearly fixed value. According to this fact, the corneal curvature center of when the LED light source 2103 irradiates the subject with light exists on the straight line 523, and can be calculated using a typical curvature radius value.

However, when the gaze point is calculated using the position of the corneal curvature center obtained using the typical curvature radius value, the gaze point position is deviated from an original position due to the individual difference of the eye ball, and an accurate gaze point position may not be able to be detected.

Figure 47:
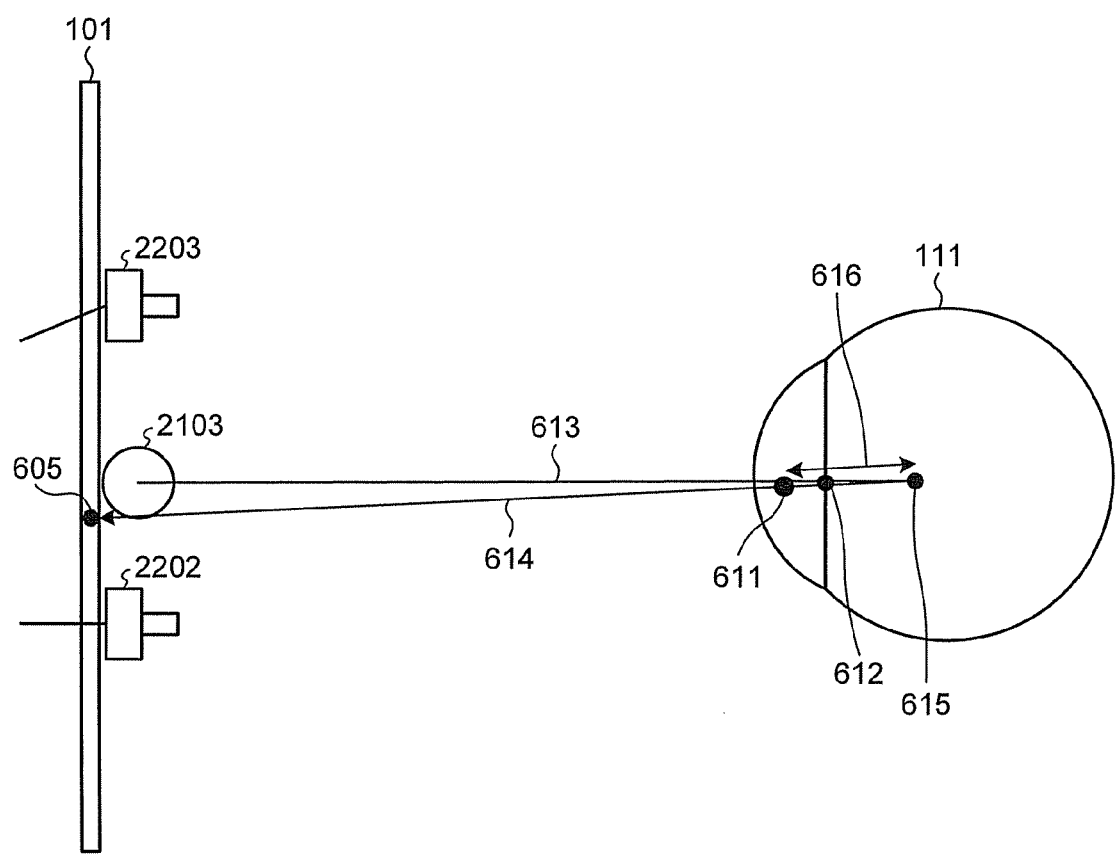
FIG. 47 is a diagram for describing calculation processing of calculating a distance between a pupil center position and a corneal curvature center position.

FIG. 47 is a diagram for describing calculation processing of calculating a corneal curvature center position, and the distance between a pupil center position and the corneal curvature center position, before the gaze point detection (eye gaze detection) is performed. Elements described in FIGS. 41 to 44 are denoted with the same reference signs, and description is omitted. Note that connection of the right and left cameras (the right camera 2202 and the left camera 2203) and the controller 2300 is not illustrated and is omitted.

A target position 605 is a position for causing the subject to gaze at, by outputting of a target image or the like to one point on a display 210. In the present embodiment, the target position 605 is a middle position on a display screen 101. A straight line 613 is a straight line that connects the LED light source 2103 and a corneal reflection center 612. A straight line 614 is a straight line that connects the target position 605 (gaze point) that the subject gazes at and a pupil center 611. A corneal curvature center 615 is an intersection point of the straight line 613 and the straight line 614. The third calculator 2353 calculates and stores a distance 616 between the pupil center 611 and the corneal curvature center 615.

Figure 48:
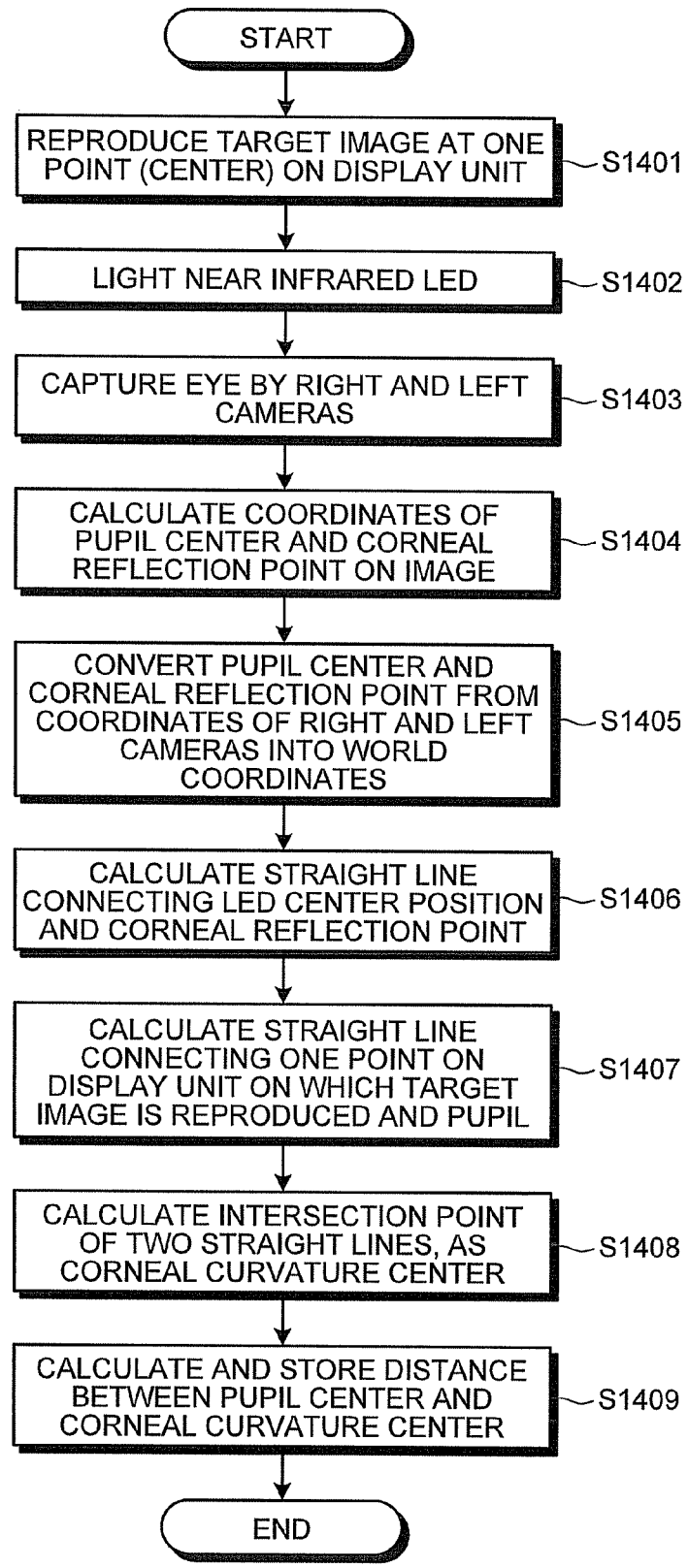
FIG. 48 is a flowchart illustrating an example of the calculation processing of the second embodiment.

FIG. 48 is a flowchart illustrating an example of calculation processing in the present embodiment.

First, the output controller 2356 reproduces the target image at one point on the display screen 101 (step S1401), and prompts the subject to gaze at the one point. Next, the controller 2300 lights the LED light source 2103 toward an eye of the subject, using an LED drive controller 316 (step S1402). The controller 2300 captures the eye of the subject by right and left cameras (a right camera 2202 and a left camera 2203) (step S1403).

By the irradiation of the LED light source 2103, a pupil part is detected as a dark part (dark pupil). Further, as reflection of the LED irradiation, a virtual image of the corneal reflection occurs, and a corneal reflection point (corneal reflection center) is detected as a bright part. That is, the first calculator 2351 detects a pupil part from a captured image, and calculates coordinates that indicate the position of the pupil center. The first calculator 2351 detects a region having predetermined brightness or less including a darkest part in a fixed region including the eye, as the pupil part, and a region having predetermined brightness or more including the brightest part, as the corneal reflection. Further, the second calculator 2352 detects a corneal reflection part from the captured image, and calculates coordinates that indicate the position of the corneal reflection center. Note that the first calculator 2351 and the second calculator 2352 calculate respective coordinate values for two images obtained by the right and left cameras (step S1404).

Note that the right and left cameras are subjected to camera calibration by a stereo calibration method in advance in order to acquire the three-dimensional world coordinates, and a conversion parameter is calculated. As the stereo calibration method, any conventionally used method can be applied, such as a method using the Tsai's camera calibration theory or the like.

The first calculator 2351 and the second calculator 2352 convert the coordinates of the right and left cameras into three-dimensional world coordinates of the pupil center and the corneal reflection center, using the conversion parameter (step S1405). The third calculator 2353 obtains a straight line that connects the obtained world coordinates of the corneal reflection center, and world coordinates of a center position of the LED light source 2103 (step S1406). Next, the third calculator 2353 calculates a straight line that connects world coordinates of a center of the target image displayed at the one point on the display screen 101, and the world coordinates of the pupil center (step S1407). The third calculator 2353 obtains an intersection point of the straight line calculated in step S1406 and the straight line calculated in step S1407, and employs this intersection point as the corneal curvature center (step S1408). The third calculator 2353 calculates a distance between the pupil center and the corneal curvature center of this time, and stores the calculated distance in the storage 150, or the like (step S1409). The stored distance is used to calculate the corneal curvature center at a subsequent time of detection of a gaze point (eye gaze).

The distance between the pupil center and the corneal curvature center of when the subject gazes at the one point on the display 210 in the calculation processing is constantly maintained within a range of detecting the gaze point in the display 210. The distance between the pupil center and the corneal curvature center may be obtained from an average of entire values calculated during the reproduction of the target image, or may be obtained from an average of values of several times, of values calculated during the reproduction.

Figure 49:
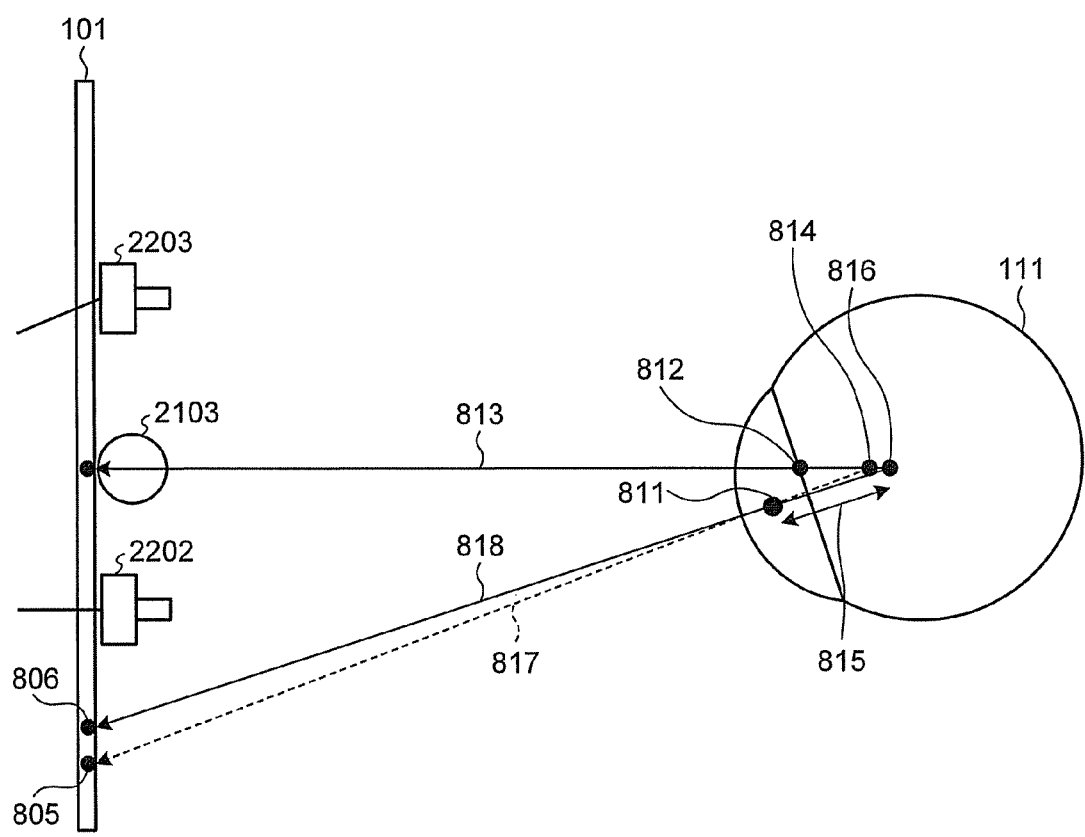
FIG. 49 is a diagram illustrating a method of calculating a corneal curvature center position using a distance obtained in advance.

FIG. 49 is a diagram illustrating a method of calculating a position of a corrected corneal curvature center, using the distance between the pupil center and the corneal curvature center obtained in advance, when the gaze point is detected. A gaze point 805 indicates the gaze point obtained from the corneal curvature center calculated using the typical curvature radius value. A gaze point 806 indicates the gaze point obtained from the corneal curvature center calculated using the distance obtained in advance.

A pupil center 811 and a corneal reflection center 812 respectively indicate the position of the pupil center calculated at the time of detecting the gaze point, and the position of the corneal reflection center. A straight line 813 is a straight line that connects the LED light source 2103 and the corneal reflection center 812. A corneal curvature center 814 is the position of the corneal curvature center calculated from the typical curvature radius value. A distance 815 is the distance between the pupil center and the corneal curvature center calculated in the previous calculation processing. A corneal curvature center 816 is the position of the corneal curvature center calculated using the distance obtained in advance. The corneal curvature center 816 is obtained from the facts that the corneal curvature center exists on the straight line 813, and the distance between the pupil center and the corneal curvature center is the distance 815. Accordingly, an eye gaze 817 calculated when the typical curvature radius value is used is corrected to an eye gaze 818. Further, the gaze point on the display screen 101 is corrected from the gaze point 805 to the gaze point 806. Note that connection of the right and left cameras (the right camera 2202 and the left camera 2203) and the controller 2300 is not illustrated and omitted.

Figure 50:
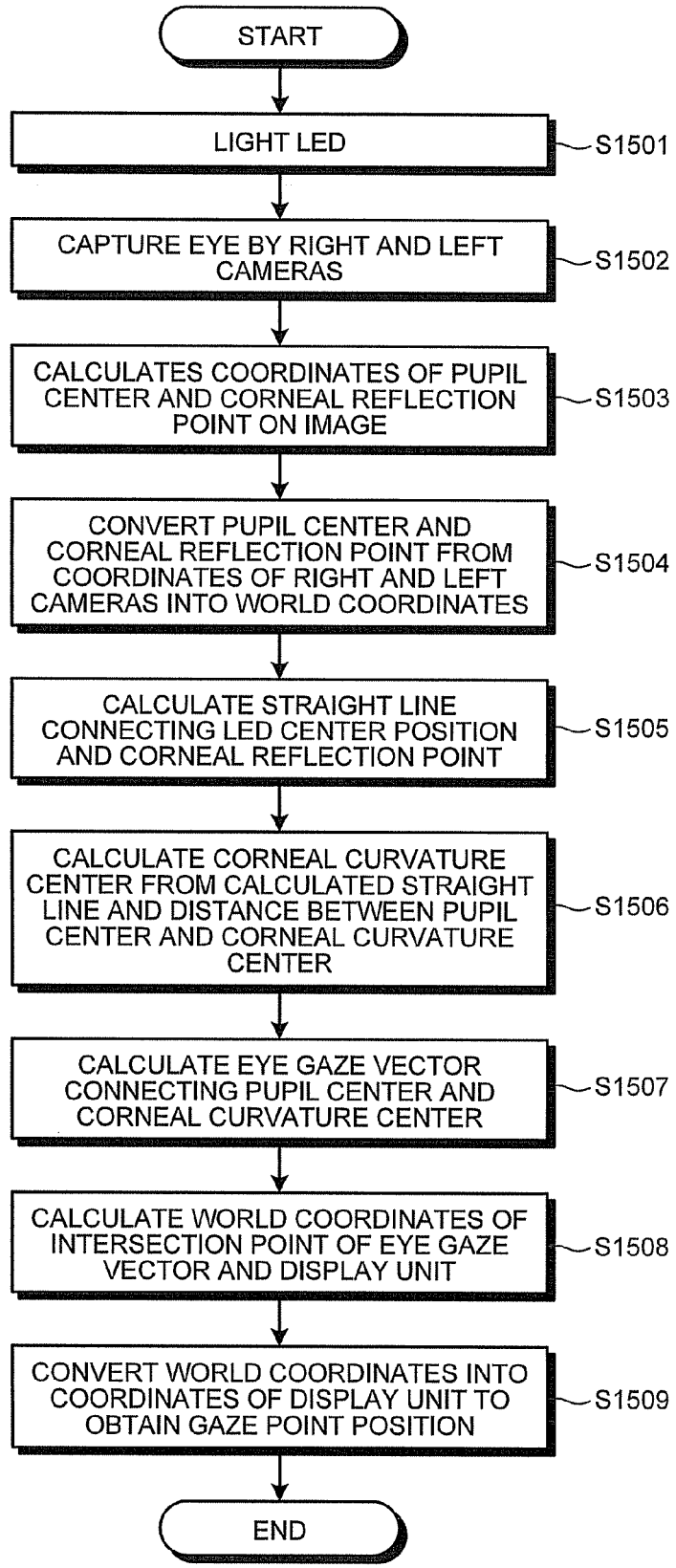
FIG. 50 is a flowchart illustrating an example of eye gaze detection processing of the second embodiment.

FIG. 50 is a flowchart illustrating an example of eye gaze detection processing of the present embodiment. For example, as processing of detecting an eye gaze in diagnosis processing using a diagnosis image, the line of sight detection processing of FIG. 50 can be executed. In the diagnosis processing, processing of displaying a diagnosis image, evaluation processing by the evaluator 2357 using the detection result of the gaze point, and the like are executed, in addition to the steps of FIG. 50.

Steps S1501 to S1505 are similar to steps S1402 to S1406 of FIG. 48, and thus description is omitted.

The third calculator 2353 calculates a position where the distance from the pupil center is equal to the distance obtained in the previous calculation processing, on the straight line calculated at step S1505, as the corneal curvature center (step S1506).

The eye gaze detector 2354 obtains a vector (eye gaze vector) that connects the pupil center and the corneal curvature center (step S1507). This vector indicates the eye gaze direction that the subject is looking at. The gaze point detector 2355 calculates three-dimensional world coordinate values of the intersection point of the eye gaze direction and the display screen 101 (step S1508). The values are coordinate values that express the one point on the display 210 that the subject gazes at, in the world coordinates. The gaze point detector 2355 converts the obtained three-dimensional world coordinate values into coordinate values (x, y) expressed in a two-dimensional coordinate system of the display 210 (step S1509). Accordingly, the gaze point on the display 210 that the subject gazes at can be calculated.

The calculating processing of calculating the distance between the pupil center position and the corneal curvature center position is not limited to the method described in FIGS. 47 and 48. Hereinafter, another example of calculation processing will be described using FIGS. 51 and 52.

Figure 51:
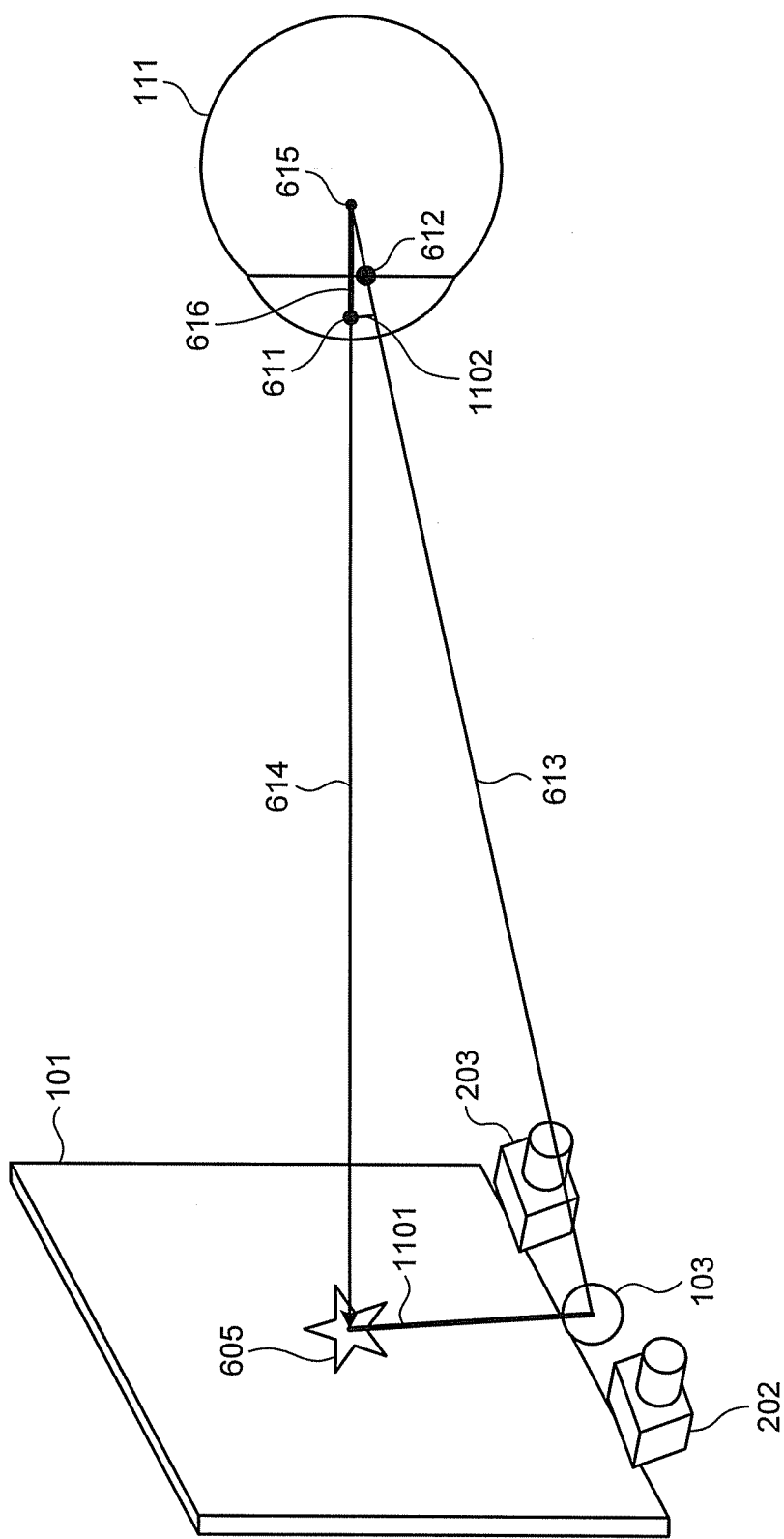
FIG. 51 is a diagram for describing calculation processing of a modification.

FIG. 51 is a diagram for describing calculation processing of the present modification. Elements described in FIGS. 41 to 44, and 47 are denoted with the same reference signs, and description is omitted.

A line segment 1101 is a line segment (first line segment) that connects a target position 605 and an LED light source 103. A line segment 1102 is a line segment (second line segment) that is parallel to the line segment 1101, and connects a pupil center 611 and a straight line 613. In the present modification, a distance 616 between the pupil center 611 and a corneal curvature center 615 is calculated using the line segment 1101 and the line segment 1102, and stored.

FIG. 52 is a flowchart illustrating an example of calculation processing of the present modification.

Steps S1601 to S1607 are similar to steps S1401 to S1407 of FIG. 48, and thus description is omitted.

A third calculator 2353 calculates a line segment (the line segment 1101 in FIG. 51) that connects a center of a target image displayed in one point on a display screen 101, and a center of the LED light source 103, and calculates a length (L1101) of the calculated line segment (step S1608).

The third calculator 2353 calculates a line segment (the line segment 1102 in FIG. 51) passing through the pupil center 611, and parallel to the line segment calculated at step S1608, and calculates the length of the calculated line segment (the length is L1102) (step S1609).

The third calculator 2353 calculates the distance 616 between the pupil center 611 and the corneal curvature center 615, based on the fact that a triangle having the corneal curvature center 615 as a vertex, and the line segment calculated at step S1608 as a base, and a triangle having the corneal curvature center 615 as a vertex, and the line segment calculated at step S1609 as a base have a similarity relationship (step S1610). For example, the third calculator 2353 calculates the distance 616 such that a ratio of the length of the line segment 1102 to the length of the line segment 1101, and a ratio of the distance 616 to the distance between the target position 605 and the corneal curvature center 615 become equal.

The distance 616 can be calculated by the following formula (11). Note that a distance L614 is the distance from the target position 605 to the pupil center 611.

$$\text{Distance } 616 = (L614 \times L1102)/(L1101 - L1102) \quad (11)$$

The third calculator 2353 stores the calculated distance 616 in a storage 150 or the like (step S1611). The stored distance is used to calculate the corneal curvature center at a subsequent time of detection of a gaze point (eye gaze).

As described above, according to the present embodiment, effects as follows can obtained, for example.
(1) It is not necessary to arrange the light source (illuminator) in two places, and detection of an eye gaze can be performed with the light source arranged in one place.
(2) Because the light source is arranged in one place, the device can be made compact, and a decrease in cost can be realized.

As described above, the present embodiments include following forms.
(Form 1)
A control device that displays, on a display, a diagnosis image that is a combination of a natural image and a pattern image, the control device including an output controller that displays, on the display, a first diagnosis image, and displays a second diagnosis image in which a portion of the natural image and the pattern image are similar, compared with the first diagnosis image, after displaying the first diagnosis image.
(Form 2)
The control device according to form 1, wherein
the output controller
displays, on the display, a third diagnosis image different from the first diagnosis image in at a position of the pattern image, and in which the portion of the natural image and the pattern image are not similar, compared with the second diagnosis image, after displaying the second diagnosis image, and displays a fourth diagnosis image different from the second diagnosis image in at least the position of the pattern image, and in which the natural image and the pattern image are similar, compared with the third diagnosis image, after displaying the third diagnosis image.
(Form 3)
The control device according to form 1 or 2, wherein,
in the second diagnosis image, at least one of hue, luminance, and chroma of the portion of the natural image and the pattern image is similar, compared with the first diagnosis image.
(Form 4)
A diagnosis device including:
the output controller according to any one of forms 1 to 3;
an imaging unit that captures a subject;
an eye gaze detector that detects an eye gaze direction of the subject, from a captured image captured by the imaging unit; and
a gaze point detector that detects a gaze point of the subject in a display region of the display, based on the eye gaze direction.
(Form 5)
The diagnosis device according to form 4, wherein
the gaze point detector detects the gaze point when the second diagnosis'image is displayed.
(Form 6)
The diagnosis supporting device according to form 4 or 5, further including an evaluator that determines whether the subject gazes at either the natural image or the pattern image.
(Form 7)
A control method that controls display of a diagnosis image that is a combination of a natural image and a pattern image, the control method including:

a step of displaying, on a display, a first diagnosis image, and then displaying a second diagnosis image in which a portion of the natural image and the pattern image are similar, compared with the first diagnosis image.

(Form 8)

A control program for causing a computer including a control device that controls display of a diagnosis image that is a combination of a natural image and a pattern image, to execute:

a step of displaying, on a display, a first diagnosis image, and then displaying a second diagnosis image in which a portion of the natural image and the pattern image are similar, compared with the first diagnosis image.

(Form 9)

A diagnosis supporting device including:

a display;

an imaging unit that captures a subject;

an eye gaze detector that detects an eye gaze direction of the subject, from a captured image captured by the imaging unit;

a gaze point detector that detects a gaze point of the subject in a plurality of divided regions that is divided display regions of the display, based on the eye gaze direction;

an output controller that displays at least two of a person image, a pattern image, and a character image, in the divided regions that are different from each other, of the plurality of divided regions, as diagnosis images, respectively; and an evaluator that calculates an evaluation value of the subject, based on the gaze point detected by the gaze point detector, when the diagnosis images are displayed.

(Form 10)

The diagnosis supporting device according to form 9, wherein the evaluator calculates the evaluation value based on at least one of a moved distance of the gaze point in a predetermined period, a moving speed of the gaze point in the predetermined period, the number of the gaze points detected in the divided region in the predetermined period, and the number of times of movement of the gaze point among the plurality of divided regions in the predetermined period.

(Form 11)

The diagnosis supporting device according to form 9, wherein the divided region includes a plurality of partial regions, and the evaluator calculates the evaluation value based on at least one of the number of the gaze points detected in the partial region in the predetermined period, and the number of times of movement of the gaze point among the plurality of partial regions in the predetermined period.

(Form 12)

The diagnosis supporting device according to form 9, wherein the evaluator calculates the evaluation value based on a time when the gaze point has been detected in the divided region including the pattern image, and a time when the gaze point has been detected in a region other than the divided region including the pattern image.

(Form 13)

The diagnosis supporting device according to form 9, wherein the output controller changes the divided region in which the diagnosis image is displayed, between a first period and a second period, and the evaluator calculates the evaluation value, based on a first evaluation value calculated in the first period, and a second evaluation value calculated in the second period.

(Form 14)

A diagnosis supporting method including:

an eye gaze detection step of detecting, from a captured image captured by an imaging unit that captures a subject, an eye gaze direction of the subject;

a gaze point detection step of detecting a gaze point of the subject in a plurality of divided regions that a display region of a display is divided, based on the eye gaze direction;

an output control step of displaying at least two of a person image, a pattern image, and a character image, in the divided regions that are different from each other, of the plurality of divided regions, as diagnosis images; and an evaluation step of calculating an evaluation value of the subject, based on the gaze point detected in the gaze point detection step, when the diagnosis image is displayed.

(Form 15)

A diagnosis supporting device including:

a display;

an imaging unit that captures a subject;

an eye gaze detector that detects an eye gaze direction of the subject, from a captured image captured by the imaging unit;

a gaze point detector that detects a gaze point of the subject in a display region of the display, based on the eye gaze direction;

an output controller that displays, on the display, a diagnosis image including an object image and a person image indicating a direction of the object; and an evaluator that calculates an evaluation value of the subject, based on the gaze point detected by the gaze point detector of when the diagnosis image is displayed.

(Form 16)

The diagnosis supporting device according to form 15, wherein the person image is an image of a person who points a finger at the direction of the object.

(Form 17)

The diagnosis supporting device according to form 15 or 16, wherein the person image is an image of a person who points at the direction of the object with a face or a direction of an eye.

(Form 18)

The diagnosis supporting device according to any one of forms 15 to 17, wherein the evaluator calculates the evaluation value, based on at least one of a first dwell time that indicates a time when the gaze point is detected in a region including the object image, and a second dwell time that indicates a time when the gaze point is detected in a region including the person image.

(Form 19)

The diagnosis supporting device according to any one of forms 15 to 18, wherein the evaluator further calculates the evaluation value, based on a third dwell time that indicates a time when the gaze point is detected in a region other than the region including the object image and the region including the person image.

(Form 20)

The diagnosis supporting device according to any one of forms 15 to 19, wherein the evaluator further calculates the evaluation value, based on a fourth dwell time that indicates a time when the gaze point is detected in a region including a pointing object image that indicates the direction of the object.

(Form 21)

The diagnosis supporting device according to any one of forms 15 to 20, wherein the output controller displays, on the display, a first diagnosis image, and then displays a second diagnosis image different from the first diagnosis image in a position of the object image and a position of the person image, and the evaluator calculates the evaluation value, based on the gaze point detected by the gaze point detector when the first diagnosis image is displayed, and the gaze point detected by the gaze point detector when the second diagnosis image is displayed.

(Form 22)

The diagnosis supporting device according to any one of forms 15 to 21, wherein the output controller displays, on the display, the diagnosis image in which an image of the person pointing at the direction of the object is displayed, after elapse of a predetermined time from start of display, and the evaluator calculates the evaluation value of the subject, based on the gaze point detected by the gaze point detector, after elapse of the predetermined time from start of display of the diagnosis image.

(Form 23)

The diagnosis supporting device according to any one of forms 15 to 22, further including:

an illuminator including a light source that performs irradiation of light;

a plurality of imaging units;

a position detector that calculates a first position that indicates a center of a pupil, and a second position of a center of a corneal reflection, from an image of an eye ball of the subject irradiated with the light by the illuminator, and captured by the imaging unit; and a calculator that calculates a fourth position that indicates a curvature center of a cornea, based on a position of the light source, a third position on the display, the first position, and the second position, wherein the eye gaze detector detects an eye gaze of the subject, based on the first position and the fourth position.

(Form 24)

A diagnosis supporting method including:

an eye gaze detection step of detecting, from a captured image captured by an imaging unit that captures a subject, an eye gaze direction of the subject;

a gaze point detection step of detecting a gaze point of the subject in a display region of a display, based on the eye gaze direction;

an output control step of displaying, on the display, a diagnosis image including an object image and a person image that indicates a direction of the object; and an evaluation step of calculating an evaluation value of the subject, based on the gaze point detected in the gaze point detection step when the diagnosis image is displayed.

According to the present invention, an effect to improve accuracy of diagnosis is exerted.

Although the invention has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

What is claimed is:

1. A diagnosis supporting device comprising:
a display;
an imaging unit configured to capture a subject;
an eye gaze detector configured to detect an eye gaze direction of the subject from a captured image captured by the imaging unit;
a gaze point detector configured to detect a gaze point of the subject in a display region of the display, based on the eye gaze direction;
an output controller configured to display, on the display, a diagnosis image that includes a person image and a geometric pattern image, and in which at least one of contrast, color density, and a degree of transmittance of the person image or the geometric pattern image is changed over time; and
an evaluator configured to calculate an evaluation value of the subject, based on the gaze point detected by the gaze point detector when the diagnosis image is displayed.

2. The diagnosis supporting device according to claim 1, wherein
the output controller displays, on the display the diagnosis image in which at least one of the contrast, the color density, and the degree of transmittance of the geometric pattern image are changed in a contradictory manner over time.

3. The diagnosis supporting device according to claim 1, wherein
the output controller displays, on the display, the diagnosis image in which a ratio of change of at least one of the contrast, the color density, and the degree of transmittance becomes a fixed value or less.

4. The diagnosis supporting device according to claim 1, wherein
the gaze point detector detects the gaze point, based on the eye gaze direction, after elapse of a predetermined time from start of display of the diagnosis image.

5. The diagnosis supporting device according to claim 1, wherein
the output controller displays a first diagnosis image on the display, and then displays a second display image which is different from the first diagnosis image in a position of the person image and a position of the geometric pattern image, and
the evaluator calculates the evaluation value, based on the gaze point detected by the gaze point detector when the first diagnosis image is displayed, and the gaze point detected by the gaze point detector when the second diagnosis image is displayed.

6. The diagnosis supporting device according to claim 1, wherein
the evaluator calculates the evaluation value, based on at least one of a first dwell time that indicates a time when the gaze point is detected in a region including the person image, and a second dwell time that indicates a time when the gaze point is detected in a region including the geometric pattern image.

7. The diagnosis supporting device according to claim 1, further comprising:
an illuminator including a light source configured to perform irradiation of light;
a plurality of imaging units;
a position detector configured to calculate a first position that indicates a center of a pupil, and a second position that indicates a center of a corneal reflection, from an image of an eye ball of a subject irradiated with the light by the illuminator and captured by the imaging units; and
a calculator configured to calculate a fourth position that indicates a curvature center of a cornea, based on a position of the light source, a third position on the display, the first position, and the second position, wherein
the eye gaze detector detects an eye gaze of the subject, based on the first position and the fourth position.

8. A diagnosis supporting method comprising:
an eye gaze detection step of detecting, from a captured image captured by an imaging unit that captures a subject, an eye gaze direction of the subject;
a gaze point detection step of detecting a gaze point of the subject in a display region on a display, based on the eye gaze direction;
an output control step of displaying, on the display, a diagnosis image including a person image and a geometric pattern image, and in which at least one of contrast, color density, a degree of transmittance of the person image or the geometric pattern image is changed over time; and
an evaluation step of calculating an evaluation value of the subject, based on the gaze point detected in the gaze point detection step when the diagnosis image is displayed.

* * * * *